(12) United States Patent
Porat et al.

(10) Patent No.: US 6,237,398 B1
(45) Date of Patent: May 29, 2001

(54) SYSTEM AND METHOD FOR MONITORING PRESSURE, FLOW AND CONSTRICTION PARAMETERS OF PLUMBING AND BLOOD VESSELS

(75) Inventors: Yariv Porat, Haifa; Yosef Tsaliah, Kiryat Bialik; Eyal Doron, Kiryat Yam, all of (IL)

(73) Assignee: Remon Medical Technologies, Ltd., Caeseria (IL)

( * ) Notice: Subject to any disclaimer, the term of this patent is extended or adjusted under 35 U.S.C. 154(b) by 0 days.

(21) Appl. No.: 09/161,658

(22) Filed: Sep. 29, 1998

Related U.S. Application Data

(63) Continuation-in-part of application No. 09/000,553, filed on Dec. 30, 1997.

(51) Int. Cl.[7] .............................. G01N 11/08; A61B 8/00
(52) U.S. Cl. .......................... 73/54.09; 73/54.06; 600/16
(58) Field of Search .............................. 73/54.06, 54.07, 73/54.09, 54.14, 597, 861.23, 861.25, 861.26, 861.27, 861.28, 861.18; 137/2, 3, 92; 600/16, 17

(56) References Cited

U.S. PATENT DOCUMENTS

| | | | |
|---|---|---|---|
| 4,480,483 | * 11/1984 | McShane | 73/861.05 |
| 4,680,957 | * 7/1987 | Dodd | 73/55 |
| 5,619,997 | 4/1997 | Kaplan | 73/54.41 |
| 5,626,630 | 5/1997 | Markowitz et al. | 607/60 |
| 5,705,753 | * 1/1998 | Hastings et al. | 73/861.28 |
| 5,728,281 | 3/1998 | Holstrom et al. | 204/403 |
| 5,776,324 | 7/1998 | Usala | 204/403 |
| 5,807,258 | 9/1998 | Cimochowski et al. | 600/454 |
| 5,833,603 | 11/1998 | Kovacs et al. | 600/317 |
| 5,855,609 | 1/1999 | Knapp | 623/11 |
| 5,873,835 | * 2/1999 | Hastings et al. | 600/488 |
| 5,886,267 | * 3/1999 | Ortiz | 73/861.61 |
| 5,891,180 | 4/1999 | Greeninger et al. | 607/32 |
| 5,911,685 | * 6/1999 | Siess et al. | 600/16 |
| 5,967,986 | * 10/1999 | Cimochowski et al. | 600/454 |

FOREIGN PATENT DOCUMENTS

98/29030    12/1997   (WO) .
99/17095     9/1998   (WO) .

OTHER PUBLICATIONS

Gupta et al, "Use of a Piezoelectric Film Sensor for Monitoring Vascular Grafts", *Am J Surg*, 160(2):182 (abstract).

* cited by examiner

*Primary Examiner*—Helen Kwok

(57) ABSTRACT

The present invention provides a system and method of quantifying flow, detecting a location of an obstruction and quantifying a degree of the obstruction in a pipe characterized in pulsatile flow. The method includes the steps of (a) attaching at least two spaced pressure sensors onto inner walls of the pipe; (b) using the at least two spaced pressure sensors for recording pressure records associated with each of the at least two pressure sensors within the pipe; and (c) using the pressure records for quantifying the pulsatile flow in the pipe, for detecting the location of the obstruction in the pipe and for quantifying the degree of the obstruction in the pipe.

28 Claims, 33 Drawing Sheets

FIG. 7a
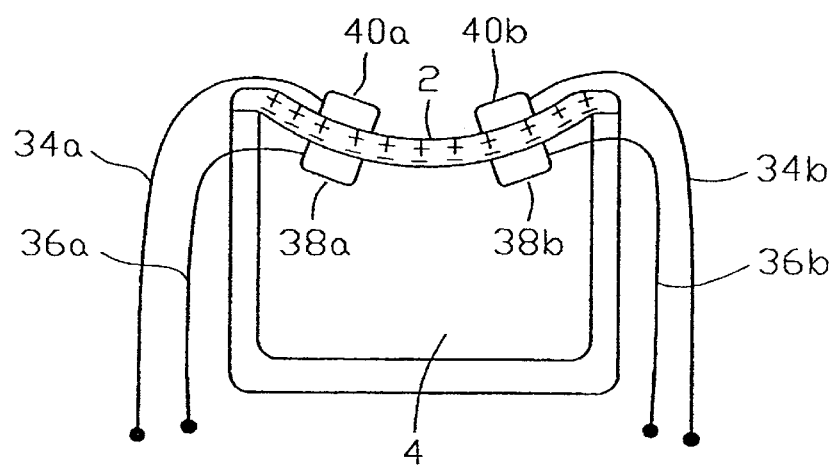
FIG. 7b
FIG. 7c
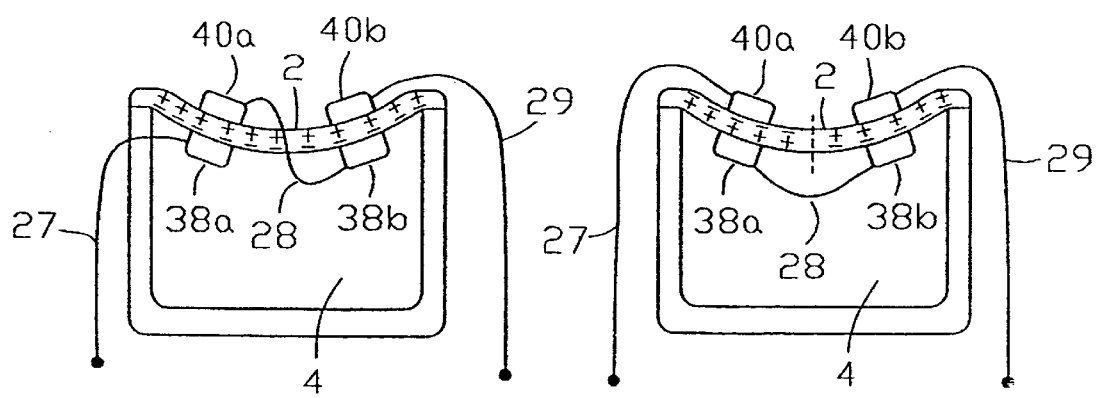

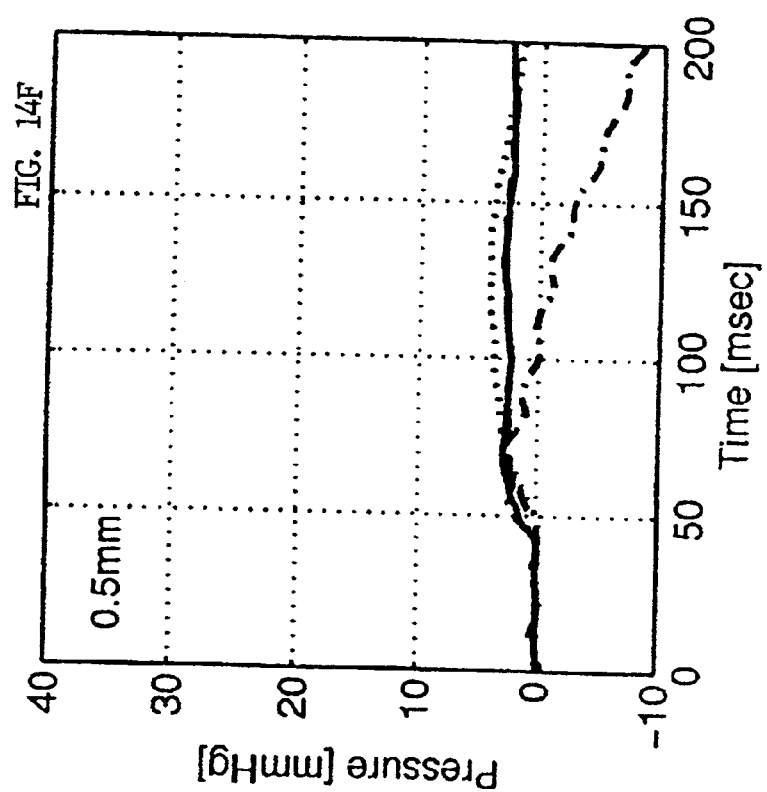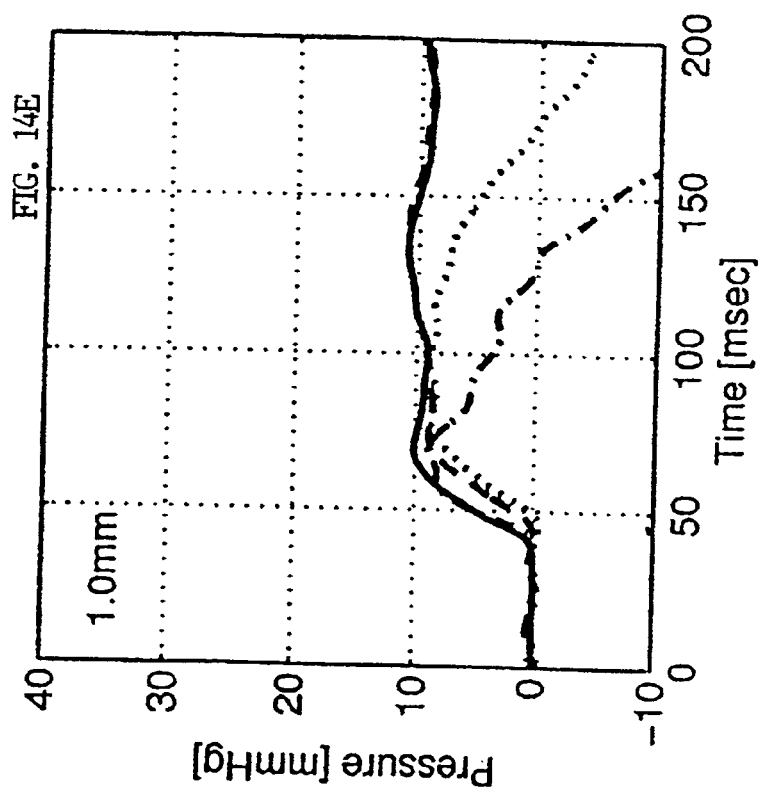

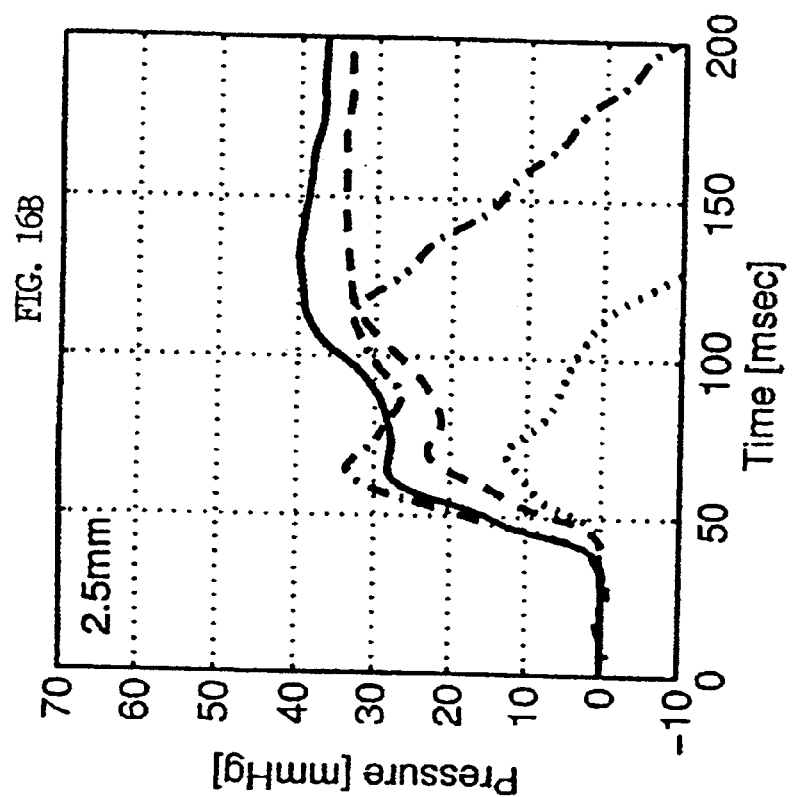
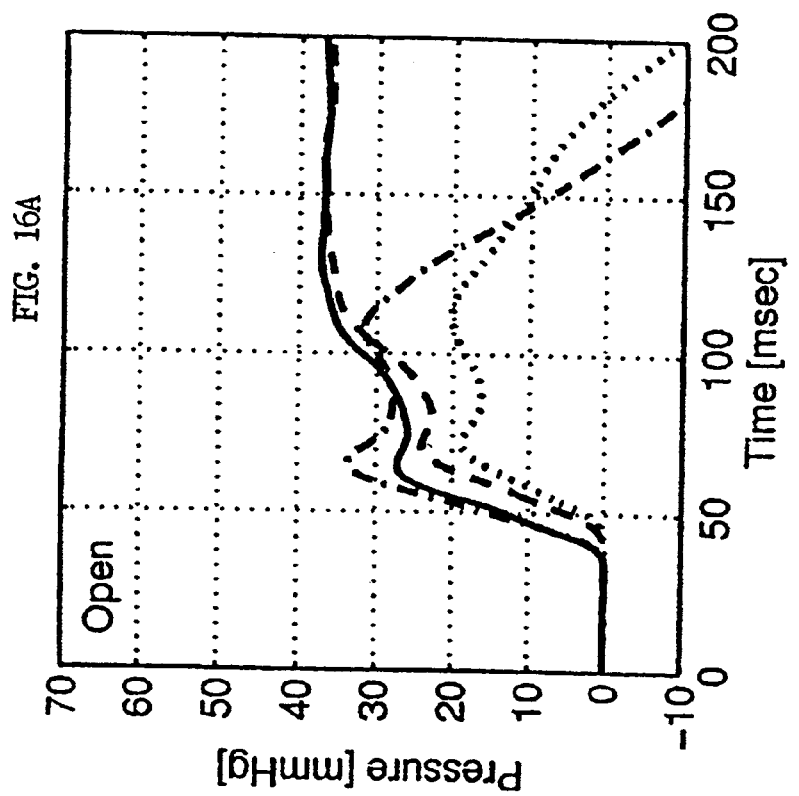

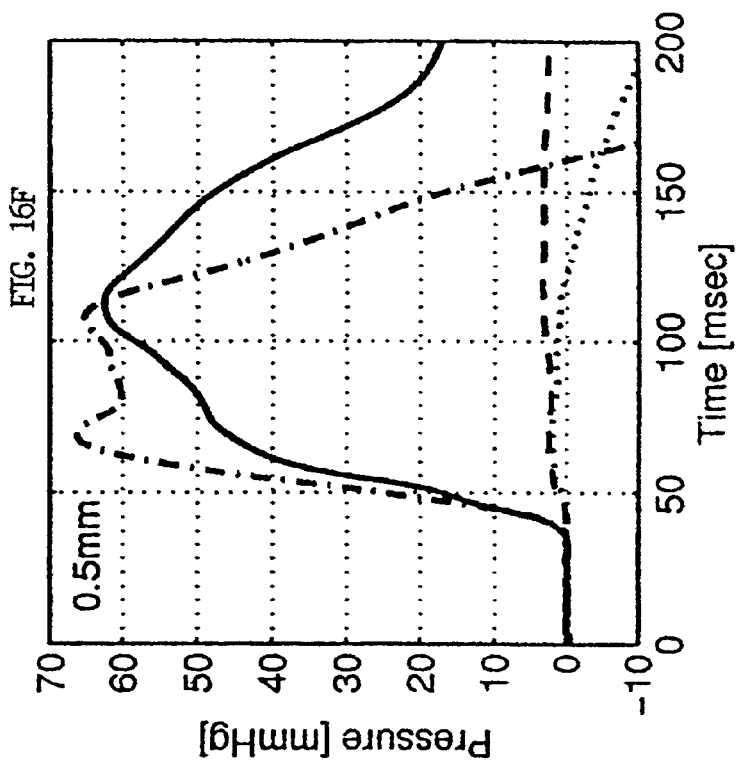
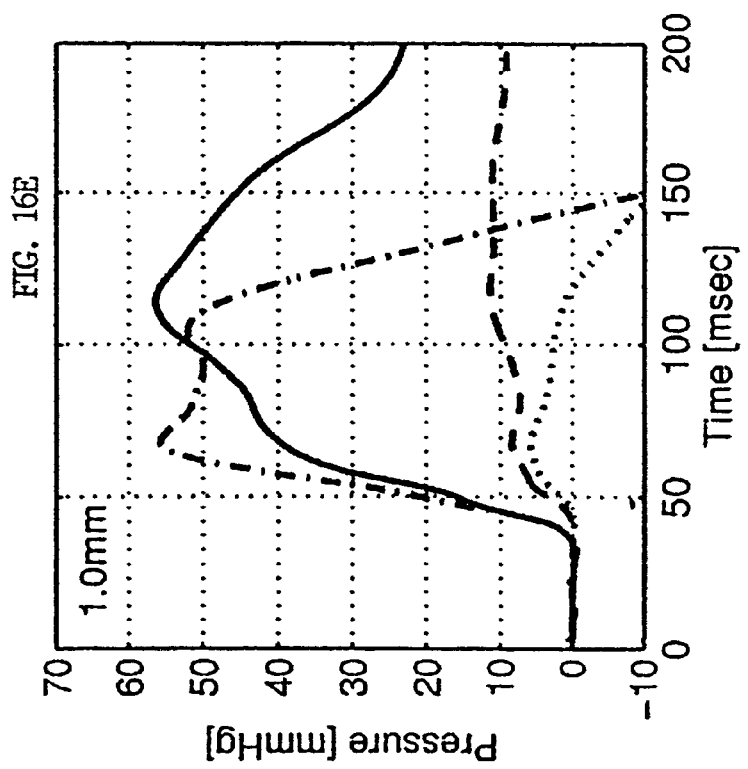

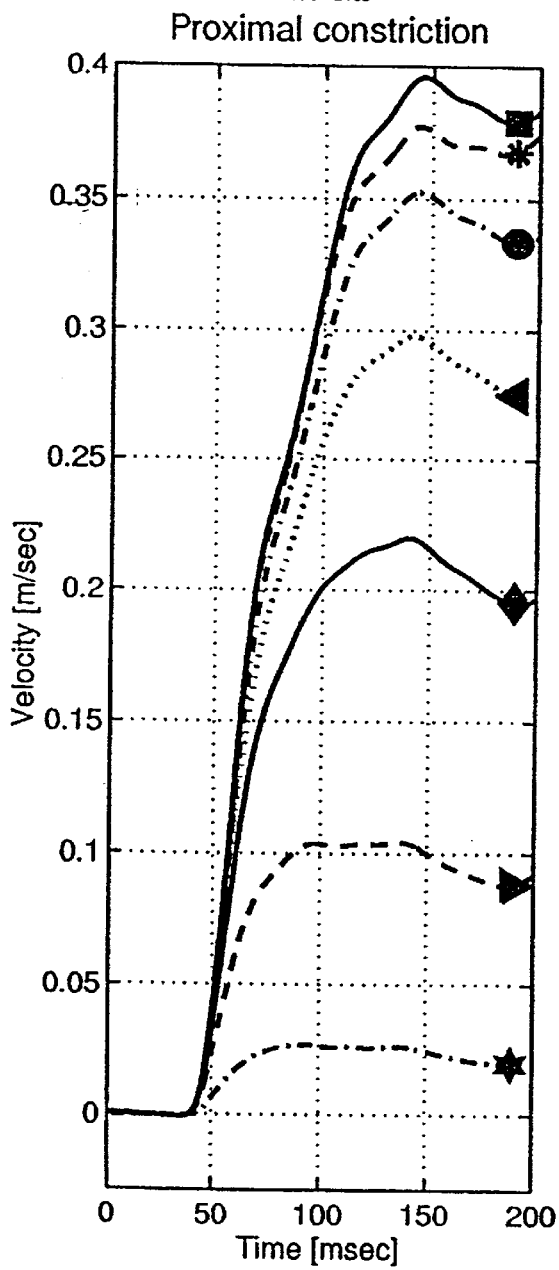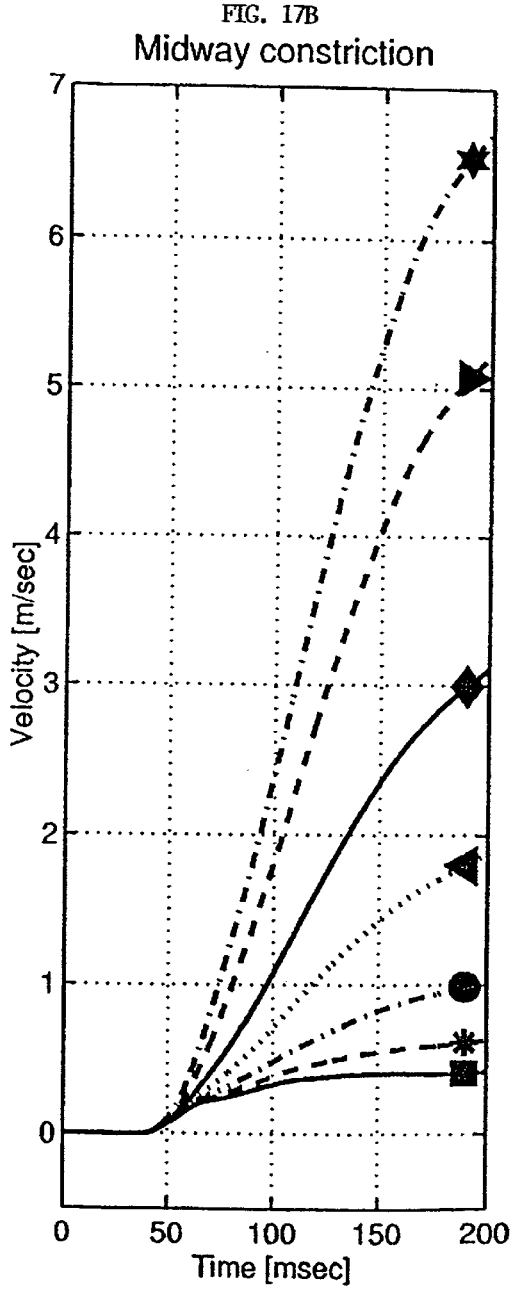
FIG. 17A Proximal constriction
FIG. 17B Midway constriction Distal constriction

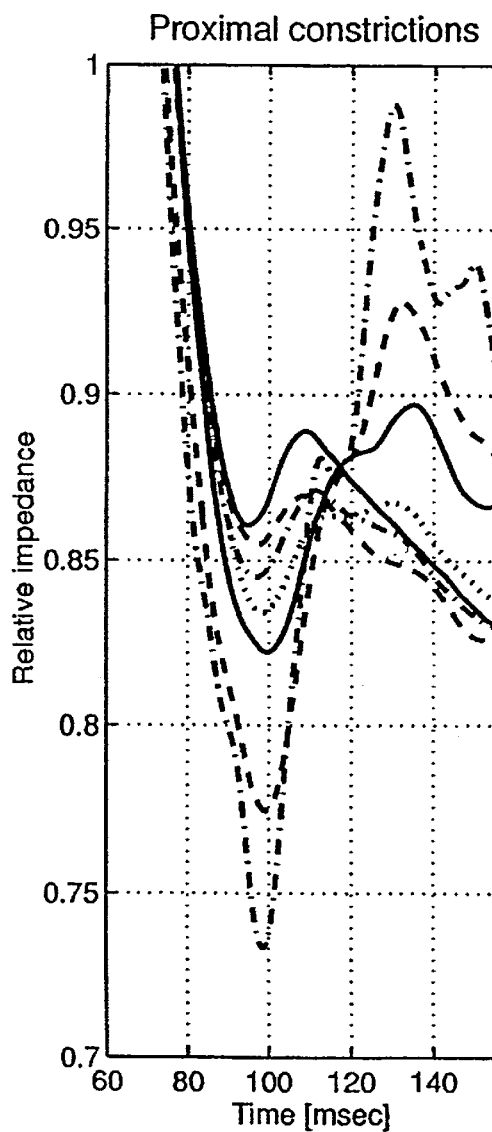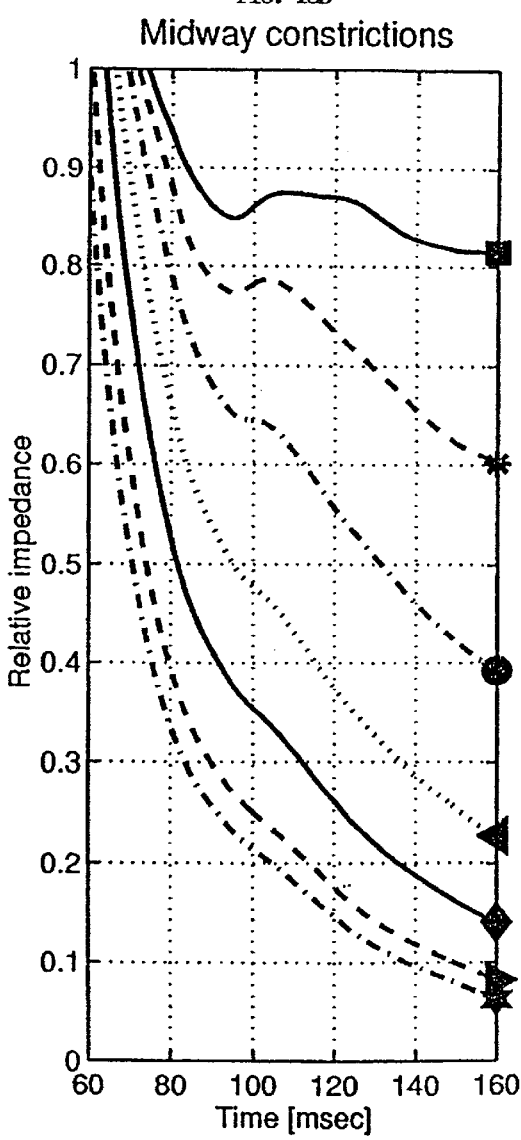
FIG. 18A Proximal constrictions
FIG. 18B Midway constrictions

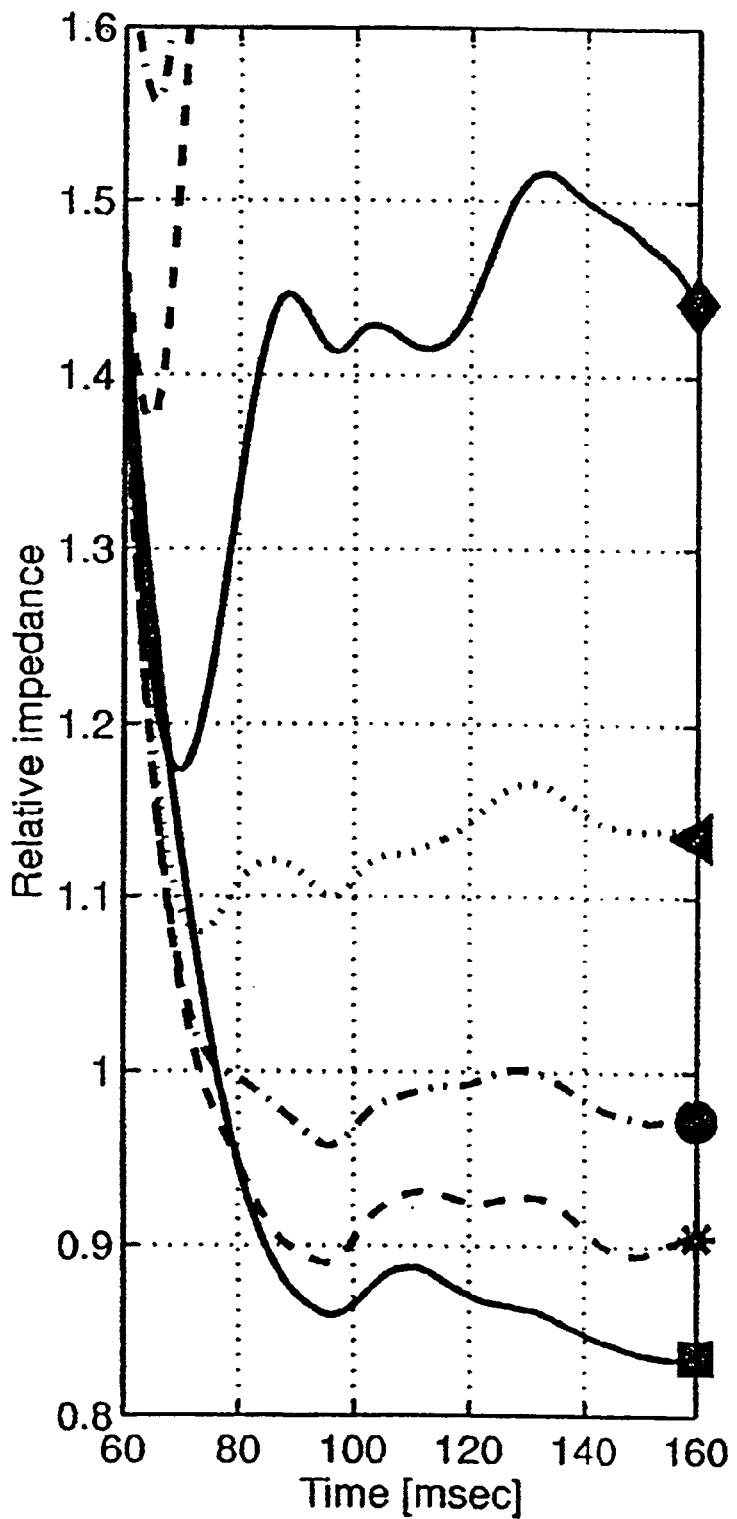

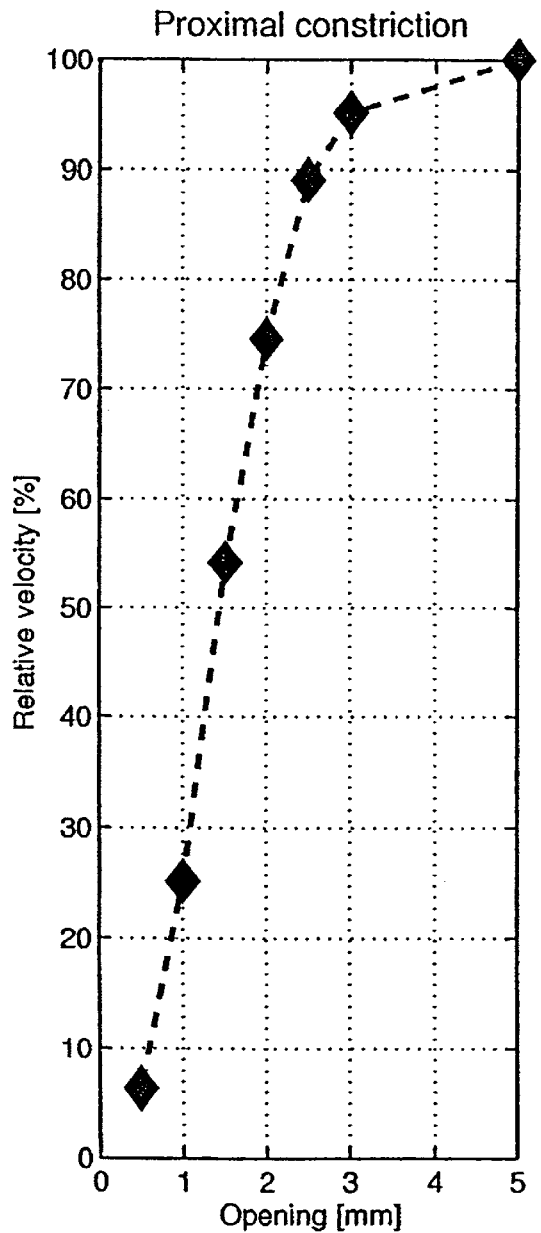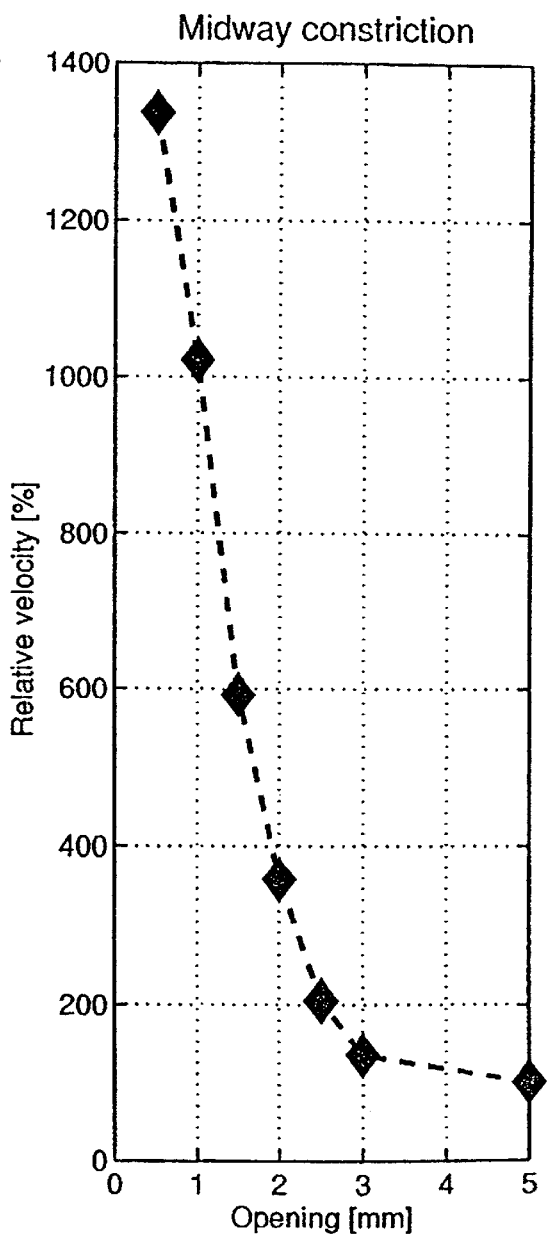
FIG. 22A Proximal constriction
FIG. 22B Midway constriction

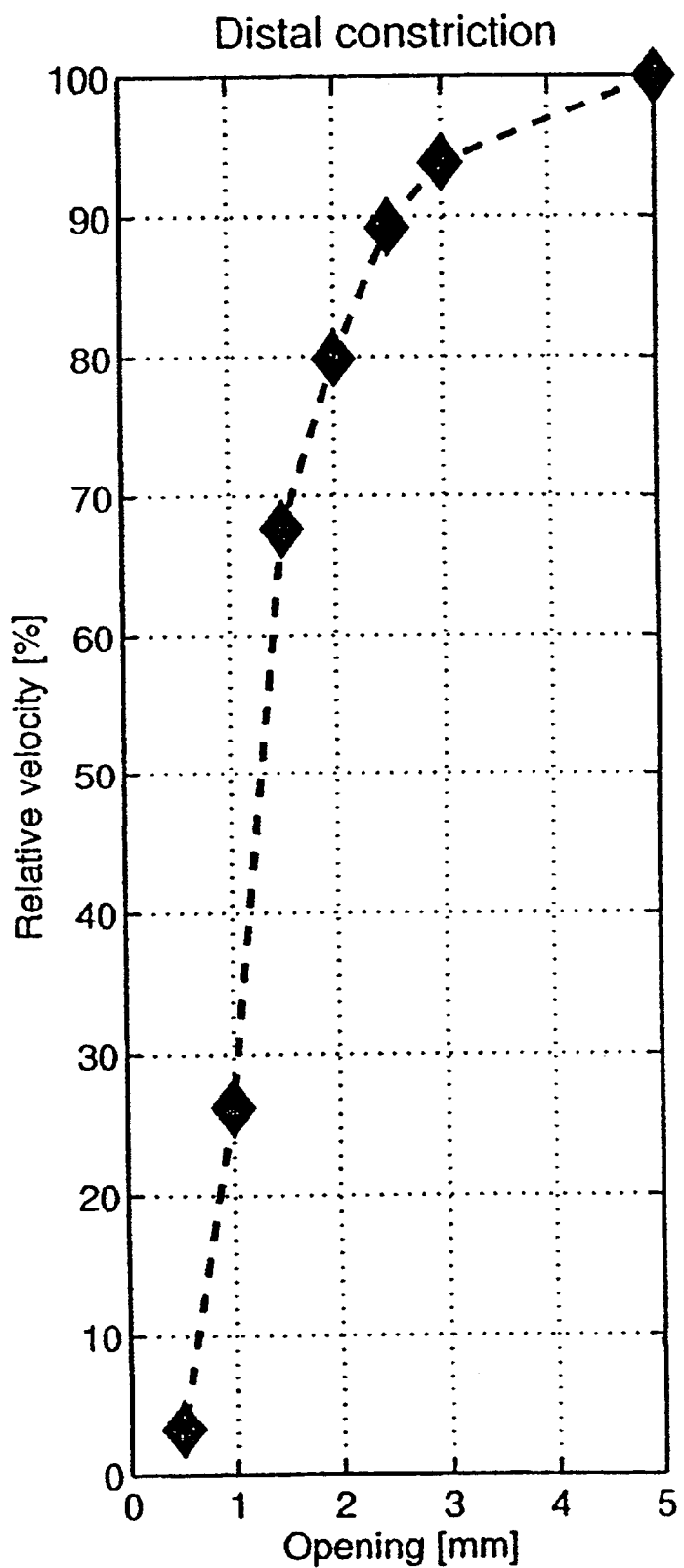

SYSTEM AND METHOD FOR MONITORING PRESSURE, FLOW AND CONSTRICTION PARAMETERS OF PLUMBING AND BLOOD VESSELS

This is a continuation-in-part of U.S. patent application Ser. No. 09/000,553, filed Dec. 30, 1997.

FIELD AND BACKGROUND OF THE INVENTION

The present invention relates to the field of monitoring pressure, flow and constriction parameters of plumbing and/or blood vessels. More particularly, the present invention relates to a system and method for monitoring pressure, flow rate and constriction degree and location within plumbing and blood vessels using an acoustical approach. Most particularly, the present invention relates to a system having a device transplantable within a plumbing installation or a blood vessel, which device collects data related to the above parameters and transmits that data to a second device of the system, external to the installation or body, so as to enable real-time non-invasive monitoring of such parameters.

Availability of real-time quantitative information regarding, for example, coronary flow may be of great value for the cardiac physician. For example, following a stent insertion or graft implantation, such data may be exploited for monitoring new constrictions formed in the grafted area. Similarly, real-time information regarding, for example plumbing flow may be of great value in hard-to-reach plumbing installations, such as in nuclear installations.

Prior art methods aimed at flow rate measurements may be divided into two major groups. The first group includes methods in which a detection probe is made in direct contact with the flowing substance. Therefore, methods associated with this group are generally referred to as invasive methods. An example of an invasive method is the thermodilution method, in which an invasive temperature detection probe is made in direct contact with the flowing substance.

The invasive methods suffer two major drawbacks for application in human diagnostics and plumbing installations. The first is their invasiveness. The second is related to the fact that an in-pipe flow rate is a function of location with respect to the pipe walls, wherein flow is substantially zero close to the walls and reaches a maximum in the central region of the pipe (also known as lumen). As a result, without positional information, or alternatively prolonged probing, the measurement is inaccurate.

The second group of methods aimed at flow rates measurements include non-invasive methods, therefore, methods associated with this group are generally termed imaging methods.

Various non-invasive imaging methods were developed for different applications in human diagnostics as well as in other fields. A common feature characterizing these methods is the use of a contrast agent, which agent is being traced. Imaging methods used primarily in human diagnostics include, for example, (i) X-ray based imaging methods in which X-rays are used to detect an administrated radiopaque contrast agent (e.g., iodine) used in X-ray real-time imaging methods; and (ii) Ultrasound based imaging methods in which ultrasonic waves are used to detect an administrated contrast agent, such as micro-bubbles, used in contrast-echo. Yet, in other imaging methods employed both in medicine and in other fields, radioactive materials are employed as detectable agents, which materials may be detected, for example, by various kinds of radioactivity counters.

Thus, while using imaging methods for flow rate determinations, the flow rate of an external contrast agent provided in an upstream region is measured.

The methods described hereinabove, in which external contrast agents are traced, suffer a major drawback when employed for medical purposes, since in the course of their application, an external contrast agent, some times poisonous or with yet undetermined accumulative effects is administrated to the human body.

Another imaging method aimed at flow rate determinations is the thermoimaging method in which the flow of a thermocontrast agent is monitored using an infrared camera. When applied to human diagnostics during by-pass surgeries, this method is known as thermal coronary angiography (TCA). See for example U.S. Pat. Nos. 4,995,398 and 5,375,603. However, TCA is applicable only during open chest surgeries.

As further detailed hereinunder, in a preferred embodiment the present invention takes a particular advantage of an acoustic transducer which is described in U.S. patent application Ser. No. 09/000,553, which is incorporated by reference as if fully set forth herein, which transducer serves for receiving acoustic energy transmitted from a remote source and converting such energy into electrical power for activating an electronic circuit and for transmitting acoustic information by modulating the reflection of an external impinging acoustic wave. Thus, U.S. patent application Ser. No. 09/000,553 teaches a miniature piezoelectric transducer element comprising (a) a cell element having a cavity; (b) a flexible piezoelectric layer attached to the cell member, the piezoelectric layer having an external surface and an internal surface, the piezoelectric layer featuring such dimensions so as to enable fluctuations thereof at its resonance frequency upon impinging of an external acoustic wave; and (c) a first electrode attached to the external surface and a second electrode attached to the internal surface of the piezoelectric layer. At least one of the electrodes may be specifically shaped so as to provide a maximal electrical output, wherein the electrical output may be current, voltage or power. A preferred shape of the electrodes includes two cores interconnected by a connecting member. The transducer element may function as a transmitter. When used as a transmitter, the electrodes are electrically connected to an electrical circuit including a switching element for modulating the reflected acoustic wave by controllably changing the mechanical impedance of the piezoelectric layer according to the frequency of an electrical message signal arriving from an electronic member, such as a sensor. Third and fourth electrodes may be attached to the piezoelectric layer and the electrical circuit, such that the switching element alternately connects the electrodes in parallel and anti-parallel electrical connections so as to controllably change the mechanical impedance of the piezoelectric layer.

WO 9829030 teaches a qualitative (rather then a quantitative) approach for flow determinations employing two adjacent pressure sensors.

The present invention successfully addresses the shortcomings of the presently known configurations by providing a device method and system for non-invasively and quantitatively monitoring pressure, flow and constriction parameters, which can find uses, in for example, monitoring the functionality of blood vessels in patients and of pipes in plumbing installations

SUMMARY OF THE INVENTION

According to the present invention there is provided a method of quantifying pulsatile flow in a pipe, the method comprising the steps of (a) attaching at least two spaced pressure sensors onto inner walls of the pipe; (b) using the at least two spaced pressure sensors for recording pressure records associated with each of the at least two pressure sensors within the pipe; and (c) using the pressure records for quantifying the pulsatile flow in the pipe.

According to the present invention there is further provided a method of detecting a location of an obstruction in a pipe characterized in pulsatile flow, the method comprising the steps of (a) attaching at least two spaced pressure sensors onto inner walls of the pipe; (b) using the at least two spaced pressure sensors for recording pressure records associated with each of the at least two pressure sensors within the pipe; and (c) using the pressure records for detecting the location of the obstruction in the pipe.

According to the present invention there is further provided a method of quantifying a degree of an obstruction in a pipe characterized in pulsatile flow, the method comprising the steps of (a) attaching at least two spaced pressure sensors onto inner walls of the pipe; (b) using the at least two spaced pressure sensors for recording pressure records associated with each of the at least two pressure sensors within the pipe; and (c) using the pressure records for quantifying the degree of the obstruction in the pipe.

According to the present invention there is further provided a method of quantifying flow, detecting a location of an obstruction and quantifying a degree of the obstruction in a pipe characterized in pulsatile flow, the method comprising the steps of (a) attaching at least two spaced pressure sensors onto inner walls of the pipe; (b) using the at least two spaced pressure sensors for recording pressure records associated with each of the at least two pressure sensors within the pipe; and (c) using the pressure records for quantifying the pulsatile flow in the pipe, for detecting the location of the obstruction in the pipe and for quantifying the degree of the obstruction in the pipe.

According to further features in preferred embodiments of the invention described below, any of the methods further comprising the step of using a non-invasive activatable transducer element for communicating data from within the pipe to a receptive transducer outside thereof.

According to still further features in the described preferred embodiments the non-invasive activatable transducer is an acoustic activatable transducer element.

According to still further features in the described preferred embodiments the step of attaching the at least two spaced pressure sensors onto inner walls of the pipe is effected by attaching the at least two spaced pressure sensors onto a platform, the platform being insertable into the pipe.

According to still further features in the described preferred embodiments the pipe is selected from the group consisting of a portion of a plumbing installation and a blood vessel.

According to still further features in the described preferred embodiments the platform is a stent insertable into a blood vessel.

According to the present invention there is further provided a system for quantifying pulsatile flow in a pipe, the system comprising (a) at least two pressure sensors; (b) a mechanism for attaching the at least two pressure sensors onto inner walls of the pipe in a spaced configuration; (c) a processing module for receiving pressure records from each of the at least two pressure sensors and for quantifying the pulsatile flow in the pipe.

According to the present invention there is further provided a system for detecting a location of an obstruction in a pipe characterized in pulsatile flow, the system comprising (a) at least two pressure sensors; (b) a mechanism for attaching the at least two pressure sensors onto inner walls of the pipe in a spaced configuration; (c) a processing module for receiving pressure records from each of the at least two pressure sensors and for detecting the location of the obstruction in the pipe.

According to the present invention there is further provided a system for quantifying a degree of an obstruction in a pipe characterized in pulsatile flow, the system comprising the steps of (a) at least two pressure sensors; (b) a mechanism for attaching the at least two pressure sensors onto inner walls of the pipe in a spaced configuration; and (c) a processing module for receiving pressure records from each of the at least two pressure sensors and for quantifying the degree of the obstruction in the pipe.

According to the present invention there is further provided a system for quantifying flow, detecting a location of an obstruction and quantifying a degree of the obstruction in a pipe characterized in pulsatile flow, the system comprising (a) at least two pressure sensors; (b) a mechanism for attaching the at least two pressure sensors onto inner walls of the pipe in a spaced configuration; (c) a processing module for receiving pressure records from each of the at least two pressure sensors and for quantifying the pulsatile flow in the pipe, for detecting the location of the obstruction in the pipe and for quantifying the degree of the obstruction in the pipe.

According to further features in preferred embodiments of the invention described below, any of the systems further comprising a non-invasive activatable transducer element for communicating data from within the pipe to a receptive transducer outside thereof.

According to still further features in the described preferred embodiments the non-invasive activatable transducer is an acoustic activatable transducer element.

According to still further features in the described preferred embodiments the a mechanism for attaching the at least two pressure sensors onto the inner walls of the pipe in the spaced configuration is a platform which serves for holding the at least two pressure sensors and is itself insertable into the pipe.

According to still further features in the described preferred embodiments the pipe is selected from the group consisting of a portion of a plumbing installation and a blood vessel.

According to still further features in the described preferred embodiments the platform is a stent insertable into a blood vessel.

According to the present invention there is further provided a method of non-invasively quantifying pressure in a pipe comprising the steps of (a) attaching at least one pressure sensor onto inner walls of the pipe; (b) attaching at least one non-invasively activatable transducer element onto inner walls of the pipe; (c) providing for communication between the at least one pressure sensor and the at least one transducer element; (d) using the at least one pressure sensor for recording pressure records; (e) using the at least one non-invasively activatable transducer element for retrieving the pressure records and for communicating the records to an outside receptive transducer.

According to the present invention there is further provided a system for non-invasively quantifying pressure in a pipe comprising the steps of (a) at least one pressure sensor for recording pressure records in the pipe; (b) a first mechanism for attaching the at least one pressure sensor onto inner walls of the pipe; (c) at least one non-invasively activatable transducer element; (d) a second mechanism for attaching the at least one non-invasively activatable transducer element onto inner walls of the pipe; and (e) a communication medium for communicating between the at least one pressure sensor and the at least one transducer element for retrieving the pressure records, and for communicating the pressure records to an outside receptive transducer.

According to further features in preferred embodiments of the invention described below, the at least one non-invasively activatable transducer element is an acousto activatable transducer element.

According to still further features in the described preferred embodiments the acousto activatable transducer element includes (i) a cell member having a cavity; (ii) a substantially flexible piezoelectric layer attached to the cell member, the piezoelectric layer having an external surface and an internal surface, the piezoelectric layer featuring such dimensions so as to enable fluctuations thereof at its resonance frequency upon impinging of an external acoustic wave; and (iii) a first electrode attached to the external surface and a second electrode attached to the internal surface.

The present invention successfully addresses the shortcomings of the presently known configurations by providing a miniaturized, sensitive and non-invasively activatable system useful in monitoring pressure, flow and constriction parameters in a pipe such as a blood vessel.

BRIEF DESCRIPTION OF THE DRAWINGS

The invention is herein described, by way of example only, with reference to the accompanying drawings, wherein:

FIG. 2a is a cross section of a transducer element according to the present invention taken along line C—C in FIG. 1a;

FIG. 2b is a cross section of a transducer element according to the present invention taken along line D—D in FIG. 1a;

FIG. 2c is a cross section of a transducer element according to the present invention taken along line E—E in FIG. 1a;

FIG. 2d is a cross section of a transducer element according to the present invention taken along line F—F in FIG. 1a;

FIG. 2e is a cross section of a transducer element according to the present invention taken along line G—G in FIG. 1a;

FIGS. 7a–7f are schematic views of possible configurations of transmitters according to the present invention including parallel and anti-parallel electrical connections for controllably changing the mechanical impedance of the piezoelectric layer;

FIGS. 14a–f show pressure for proximal constrictions measured by the first (solid) and second (dash) Biometrix sensors, and by the first (dot) and second (dash-dot) PVDF sensors;

FIGS. 16a–f show pressure for midway constrictions measured by the first (solid) and second (dash) Biometrix sensors, and by the first (dot) and second (dash-dot) PVDF sensors;

FIGS. 17a–c show velocity of open pipe (squak), and 3 mm (osterisk), 2.5 mm (circle), 2 mm (left triangle), 1.5 mm (rhombus), 1 mm (right triangle) and 0.5 mm (star of David) constrictions;

FIGS. 18a–c show impedence of open pipe (squak), and 3 mm (osterisk), 2.5 mm (circle), 2 mm (left triangle), 1.5 mm (rhombus), 1 mm (right triangle) and 0.5 mm (star of David) constrictions;

FIGS. 22a–c show velocity at the 100 msec mark relative to the open case for distal, midway and proximal constrictions, respectively;

DESCRIPTION OF THE PREFERRED EMBODIMENTS

Figure 1A:
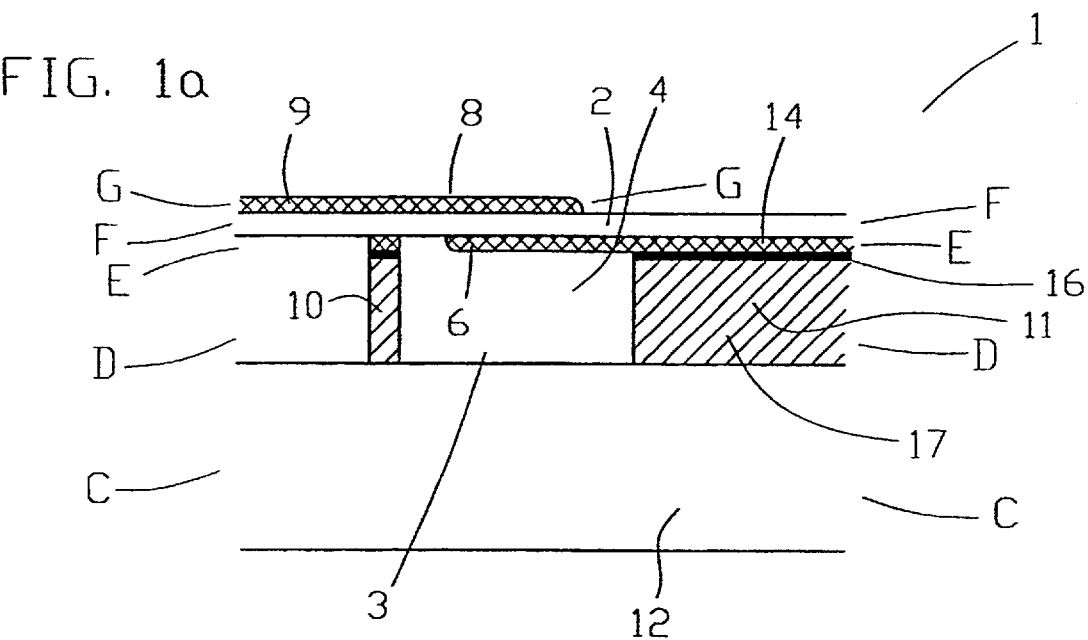
FIG. 1a is a longitudinal section of a transducer element according to the present invention taken along lines A—A in FIGS. 2a–2e.

The present invention is of a system and method which can be used for quantitative monitoring of pressure, flow and constriction parameters in a pipe. Specifically, the present invention can be used to quantitatively monitor pressure, flow rate and constriction degree and location within plumbing and blood vessels using an acoustical approach.

The principles and operation of a system and method according to the present invention may be better understood with reference to the drawings and accompanying descriptions.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

For purposes of better understanding the system and method according to the present invention, as illustrated in FIGS. 10a–24 of the drawings, reference is first made to the construction and operation of a transducer as described in U.S. patent application Ser. No. 09/000,553.

Referring now to the drawings, FIGS. 1a, 1b and 2a–2e illustrate a preferred embodiment of a transducer element according to the present invention. As shown in the figures, the transducer element 1 includes at least one cell member 3 including a cavity 4 etched into a substrate and covered by a substantially flexible piezoelectric layer 2. Attached to piezoelectric layer 2 are an upper electrode 8 and a lower electrode 6, the electrodes for connection to an electronic circuit.

The substrate is preferably made of an electrical conducting layer 11 disposed on an electrically insulating layer 12, such that cavity 4 is etched substantially through the thickness of electrically conducting layer 11.

Electrically conducting layer 11 is preferably made of copper and insulating layer 12 is preferably made of a polymer such as polyimide. Conventional copper-plated polymer laminate such as KAPTON™ sheets may be used for the production of transducer element 1. Commercially available laminates such as NOVACLAD™ may be used. Alternatively, the substrate may include a silicon layer, or any other suitable material. Alternatively, layer 11 is made of a non-conductive material such as PYRALIN™.

Preferably, cavity 4 is etched into the substrate by using conventional printed-circuit photolithography methods. Alternatively, cavity 4 may be etched into the substrate by using VLSI/micro-machining technology or any other suitable technology.

Piezoelectric layer 2 may be made of PVDF or a copolymer thereof. Alternatively, piezoelectric layer 2 is made of a substantially flexible piezoceramic. Preferably, piezoelectric layer 2 is a poled PVDF sheet having a thickness of about 9–28 $\mu$m. Preferably, the thickness and radius of flexible layer 2, as well as the pressure within cavity 4, are specifically selected so as to provide a predetermined resonant frequency. When using the embodiment of FIGS. 1a and 1b, the radius of layer 2 is defined by the radius of cavity 4.

By using a substantially flexible piezoelectric layer 2, the invention described in U.S. patent application Ser. No. 09/000,553 allows to provide a miniature transducer element whose resonant frequency is such that the acoustic wavelength is much larger than the extent of the transducer. This enables the transducer to be omnidirectional even at resonance, and further allows the use of relatively low frequency acoustic signals which do not suffer from significant attenuation in the surrounding medium.

Prior art designs of miniature transducers, however, rely on rigid piezoceramic usually operating in thickness mode. In such cases the resonant frequency relates to the size of the element and speed of sound in the piezoceramic, and is higher by several orders of magnitude.

The invention described in U.S. patent application Ser. No. 09/000,553 provides a transducer which is omnidirectional, i.e., insensitive to the direction of the impinging acoustic rays, thereby substantially simplifying the transducer's operation relative to other resonant devices. Such a transducer element is thus suitable for application in confined or hidden locations, where the orientation of the transducer element cannot be ascertained in advance.

According to a specific embodiment, cavity 4 features a circular or hexagonal shape with radius of about 200 $\mu$m. Electrically conducting layer 11 preferably has a thickness of about 15 $\mu$m. Cell member 3 is preferably etched completely through the thickness of electrically conducting layer 11. Electrically insulating layer 12 preferably features a thickness of about 50 $\mu$m. The precise dimensions of the various elements of a transducer element according to the invention described in U.S. patent application Ser. No. 09/000,553 may be specifically tailored according to the requirements of the specific application.

Cavity 4 preferably includes a gas such as air. The pressure of gas within cavity 4 may be specifically selected so as to predetermine the sensitivity and ruggedness of the transducer as well as the resonant frequency of layer 2.

Figure 2A:
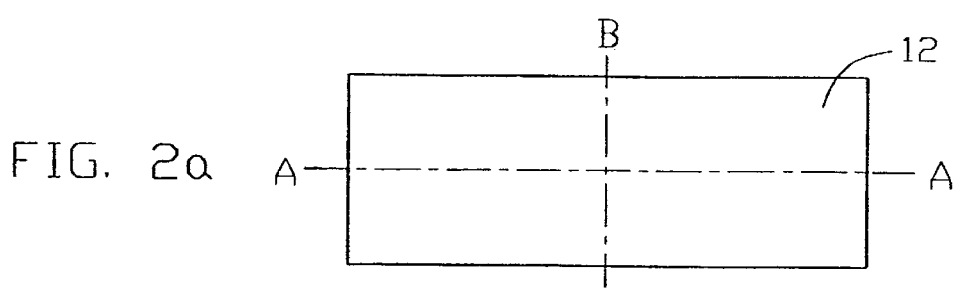
Figure 2B:
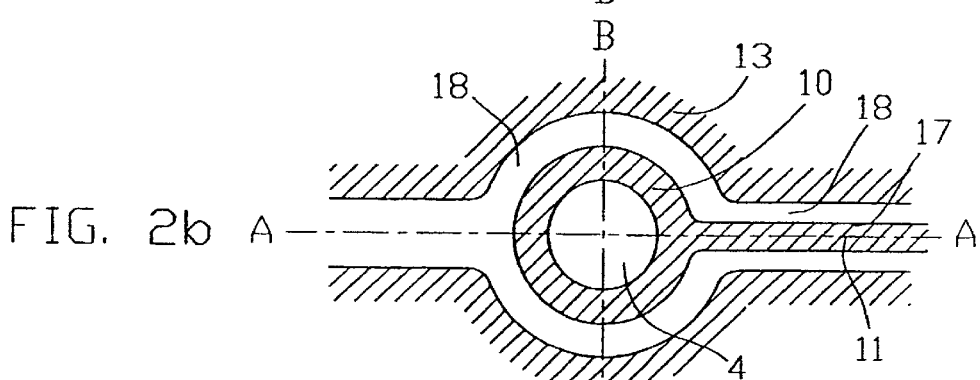

As shown in FIG. 2b, an insulating chamber 18 is etched into the substrate, preferably through the thickness of conducting layer 11, so as to insulate the transducer element from other portions of the substrate which may include other electrical components such as other transducer elements etched into the substrate. According to a specific embodiment, the width of insulating chamber 18 is about 100 $\mu$m. As shown, insulating chamber 18 is etched into the substrate so as to form a wall 10 of a predetermined thickness enclosing cavity 4, and a conducting line 17 integrally made with wall 10 for connecting the transducer element to another electronic component preferably etched into the same substrate, or to an external electronic circuit.

Figure 1B:
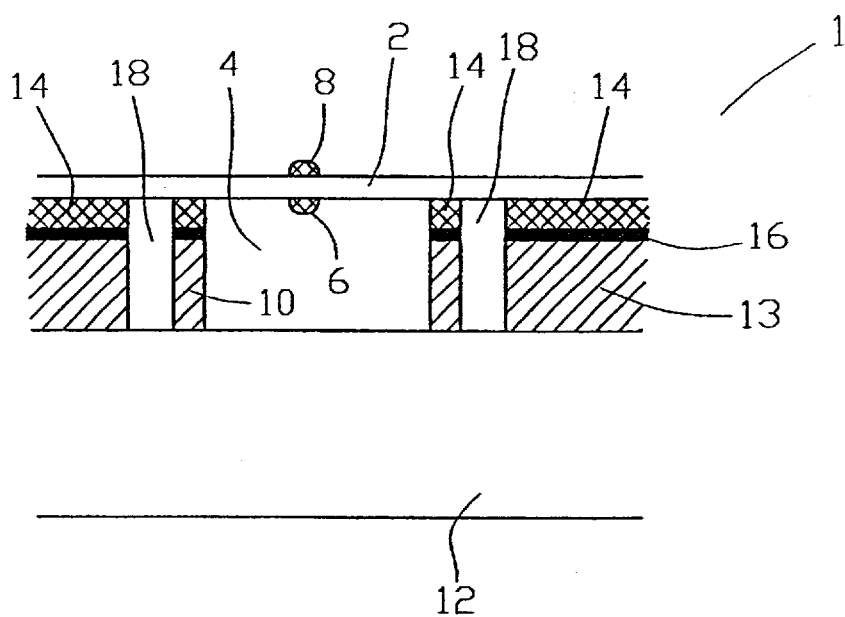
FIG. 1b is a longitudinal section of a transducer element according to the present invention taken along lines B—B in FIGS. 2a–2e.
Figure 2C:
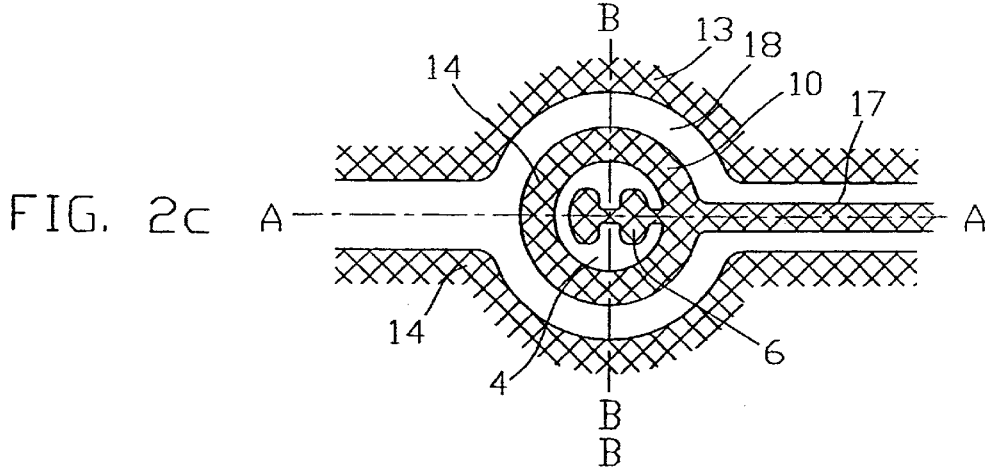
Figure 2D:
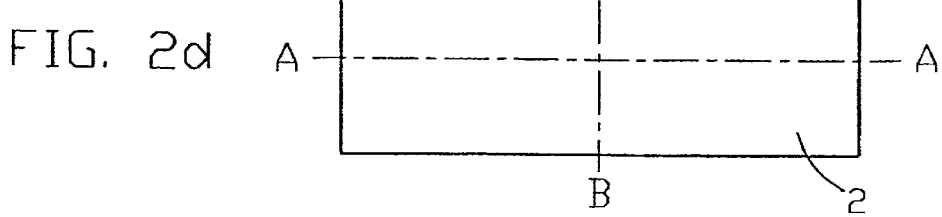
Figure 2E:
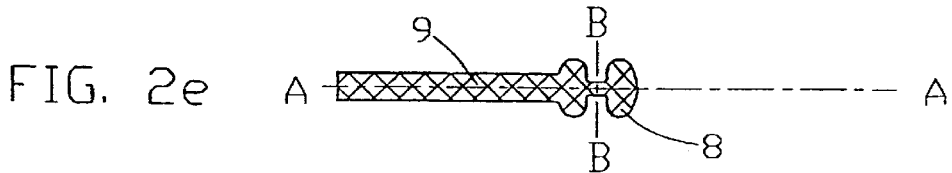

As shown in FIGS. 1*a* and 1*b*, attached to piezoelectric layer 2 are upper electrode 8 and lower electrode 6. As shown in FIGS. 2*c* and 2*e*, upper electrode 8 and lower electrode 6 are preferably precisely shaped, so as to cover a predetermined area of piezoelectric layer 2. Electrodes 6 and 8 may be deposited on the upper and lower surfaces of piezoelectric membrane 2, respectively, by using various methods such as vacuum deposition, mask etching, painting, and the like.

As shown in FIG. 1*a*, lower electrode 6 is preferably made as an integral part of a substantially thin electrically conducting layer 14 disposed on electrically conducting layer 11. Preferably, electrically conducting layer 14 is made of a Nickel-Copper alloy and is attached to electrically conducting layer 11 by means of a sealing connection 16. Sealing connection 16 may be made of indium. According to a preferred configuration, sealing connection 16 may feature a thickness of about 10 $\mu$m, such that the overall height of wall 10 of cavity 4 is about 20–25 $\mu$m.

As shown in FIG. 2*c*, electrically conducting layer 14 covers the various portions of conducting layer 11, including wall 10 and conducting line 17. The portion of conducting layer 14 covering conducting line 17 is for connection to an electronic component, as further detailed hereinunder.

According to a preferred embodiment, electrodes 6 and 8 are specifically shaped to include the most energy-productive region of piezoelectric layer 2, so as to provide maximal response of the transducer while optimizing the electrode area, and therefore the cell capacitance, thereby maximizing a selected parameter such as voltage sensitivity, current sensitivity, or power sensitivity of the transducer element.

The vertical displacement of piezoelectric layer 2, $\Psi$, resulting from a monochromatic excitation at angular frequency $\omega$ is modeled using the standard equation for thin plates:

$$(\nabla^2 - \gamma^2)(\nabla^2 + \gamma^2)\Psi - \frac{3(1-v^2)}{2Qh^3}P + \frac{3iZ\omega(1-v^2)}{2Qh^3}\Psi = 0$$

wherein Q is the Young's modulus representing the elasticity of layer 2; h the half-thickness of layer 2; v is the Poisson ratio for layer 2; $\gamma$ is the effective wavenumber in the layer given by: $\gamma^4 = 3\rho(1-v^2)\omega^2/Qh^2$, wherein $\rho$ is the density of layer 2 and $\omega$ is the angular frequency of the applied pressure (wherein the applied pressure may include the acoustic pressure, the static pressure differential across layer 2 and any other pressure the transducer comes across); Z is the mechanical impedance resulting from the coupling of layer 2 to both external and internal media of cavity 4, wherein the internal medium is preferably air and the external medium is preferably fluid; P is the acoustic pressure applied to layer 2, and $\overline{\Psi}$ represents the average vertical displacement of layer 2.

When chamber 4 is circular, the solution (given for a single frequency component $\omega$) representing the dynamic displacement of a circular layer 2 having a predetermined radius $\alpha$, expressed in polar coordinates, is:

$$\Psi(r,\varphi) = \frac{I_1(\gamma a)[J_0(\gamma r) - J_0(\gamma a)] + J_1(\gamma a)[I_0(\gamma r) - I_0(\gamma a)]}{2h\rho\omega^2 L_0(\gamma a) + i\omega ZL_2(\gamma a)} P$$

$$L_0(z) = I_0(z)J_1(z) + J_0(z)I_1(z), \quad L_2(z) = J_2(z)I_1(z) - I_2(z)J_1(z)$$

$$Z = \frac{P_A}{i\omega H_A} + i\left[\frac{4}{3\pi} + \frac{1}{6}\right]\omega\rho_W a$$

wherein $\Psi(r,\phi)$ is time-dependent and represents the displacement of a selected point located on circular layer 2, the specific location of which is given by radius r and angle $\phi$; J and I are the normal and modified Bessel functions of the first kind, respectively; $P_A$, $H_A$ are the air pressure within cavity 4 and the height of chamber 4, respectively; and $\rho_W$ is the density of the fluid external to cavity 4.

The first term of the impedance Z relates to the stiffness resulting from compression of air within cavity 4, and the second term of Z relates to the mass added by the fluid boundary layer. An additional term of the impedance Z relating to the radiated acoustic energy is substantially negligible in this example.

The charge collected between electrodes 6 and 8 per unit area is obtained by evaluating the strains in layer 2 resulting from the displacements, and multiplying by the pertinent off-diagonal elements of the piezoelectric strain coefficient tensor, $e_{31}$, $e_{32}$, as follows:

$$Q(r,\varphi,t) = e_{31}\left(\frac{\partial \Psi}{\partial x}\right)^2 + e_{32}\left(\frac{\partial \Psi}{\partial y}\right)^2$$

wherein $Q(r,\phi,t)$ represents the charge density at a selected point located on circular layer 2, the specific location of which is given by radius r and angle $\phi$; x is the stretch direction of piezoelectric layer 2; y is the transverse direction (the direction perpendicular to the stretch direction) of layer 2; $e_{31}$, $e_{32}$ are off-diagonal elements of the piezoelectric strain coefficient tensor representing the charge accumulated at a selected point on layer 2 due to a given strain along the x and y directions, respectively, which coefficients being substantially dissimilar when using a PVDF layer. T is the displacement of layer 2, taken as the sum of the displacement for a given acoustic pressure P at frequency $f$, and the static displacement resulting from the pressure differential between the interior and exterior of cavity 4, which displacements being extractable from the equations given above.

The total charge accumulated between electrodes 6 and 8 is obtained by integrating $Q(r,\phi,t)$ over the entire area S of the electrode:

$$Q = \int_S Q(r,\varphi,t)\overrightarrow{dx}$$

The capacitance C of piezoelectric layer 2 is given by:

$$C = \frac{\varepsilon}{2h}\int_S \overrightarrow{dx},$$

wherein $\epsilon$ is the dielectric constant of piezoelectric layer 2; and 2h is the thickness of piezoelectric layer 2.

Accordingly, the voltage, current and power responses of piezoelectric layer 2 are evaluated as follows:

$$V = \frac{2h \int_S Q(r, \varphi, t)\overrightarrow{dx}}{\varepsilon \int_S \overrightarrow{dx}}, \quad I = 2i\omega \int_S Q(r, \varphi, t)\overrightarrow{dx},$$

$$W = \frac{4ih\left[\int_S Q(r, \varphi, t)\overrightarrow{dx}\right]^2}{\varepsilon \int_S \overrightarrow{dx}}$$

The DC components of Q are usually removed prior to the evaluation, since the DC currents are usually filtered out. The values of Q given above represent peak values of the AC components of Q, and should be modified accordingly, so as to obtain other required values such as RMS values.

According to the above, the electrical output of the transducer expressed in terms of voltage, current and power responses depend on the AC components of Q, and on the shape S of the electrodes. Further, as can be seen from the above equations, the voltage response of the transducer may be substantially maximized by minimizing the area of the electrode. The current response, however, may be substantially maximized by maximizing the area of the electrode.

Figure 3:
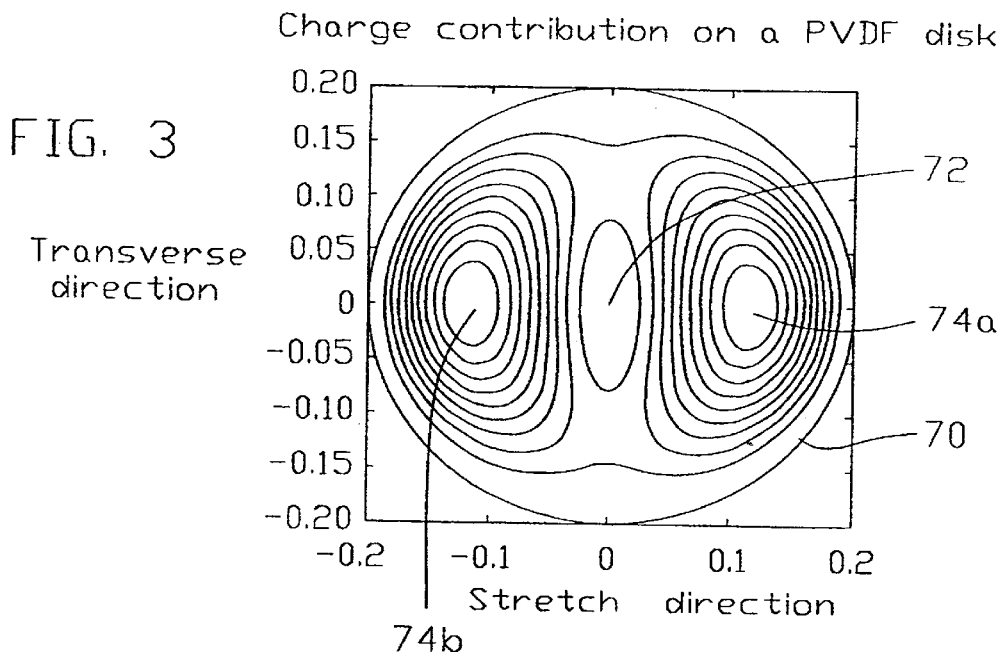
FIG. 3 shows the distribution of charge density across a piezoelectric layer of a transducer element resulting from the application of a constant pressure over the entire surface of the layer.
Figure 4A:
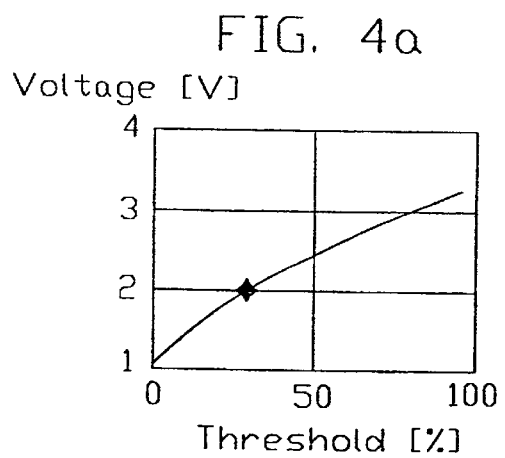
FIG. 4 shows the results of optimization performed for the power response of a transducer according to the present invention.
Figure 4C:
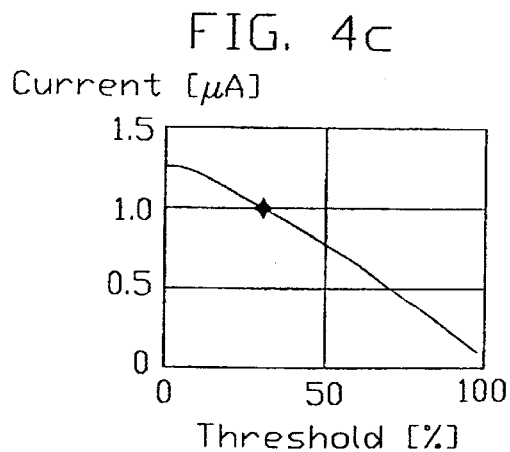
Figure 4B:
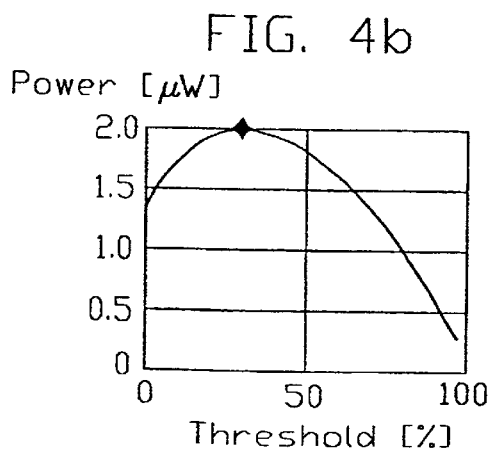
Figure 4D:
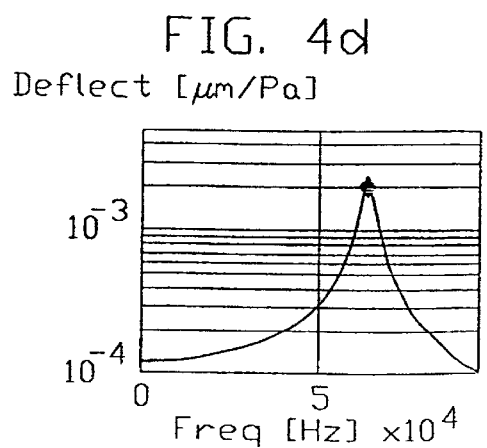

FIG. 3 shows the distribution of charge density on a circular piezoelectric layer 2 obtained as a result of pressure (acoustic and hydrostatic) applied uniformly over the entire area of layer 2, wherein specific locations on layer 2 are herein defined by using Cartesian coordinates including the stretch direction (x direction) and the transverse direction (y direction) of layer 2. It can be seen that distinct locations on layer 2 contribute differently to the charge density. The charge density vanishes at the external periphery 70 and at the center 72 of layer 2 due to minimal deformation of these portions. The charge density is maximal at two cores 74a and 74b located symmetrically on each side of center 72 due to maximal strains (in the stretch direction) of these portions.

A preferred strategy for optimizing the electrical responses of the transducer is to shape the electrode by selecting the areas contributing at least a selected threshold percentage of the maximal charge density, wherein the threshold value is the parameter to be optimized. A threshold value of 0% relates to an electrode covering the entire area of layer 2.

FIG. 4 shows the results of an optimization performed for the power response of a transducer having a layer 2 of a predetermined area. As shown in the Figure, the threshold value which provides an optimal power response is about 30% (graph b). Accordingly, an electrode which covers only the portions of layer 2 contributing at least 30% of the maximal charge density yields a maximal power response. The pertinent voltage response obtained by such an electrode is higher by a factor of 2 relative to an electrode completely covering layer 2 (graph a). The current response obtained by such electrode is slightly lower relative to an electrode completely covering layer 2 (graph c). Further as shown in the Figure, the deflection of layer 2 is maximal when applying an acoustic signal at the resonant frequency of layer 2 (graph d).

Figure 5:
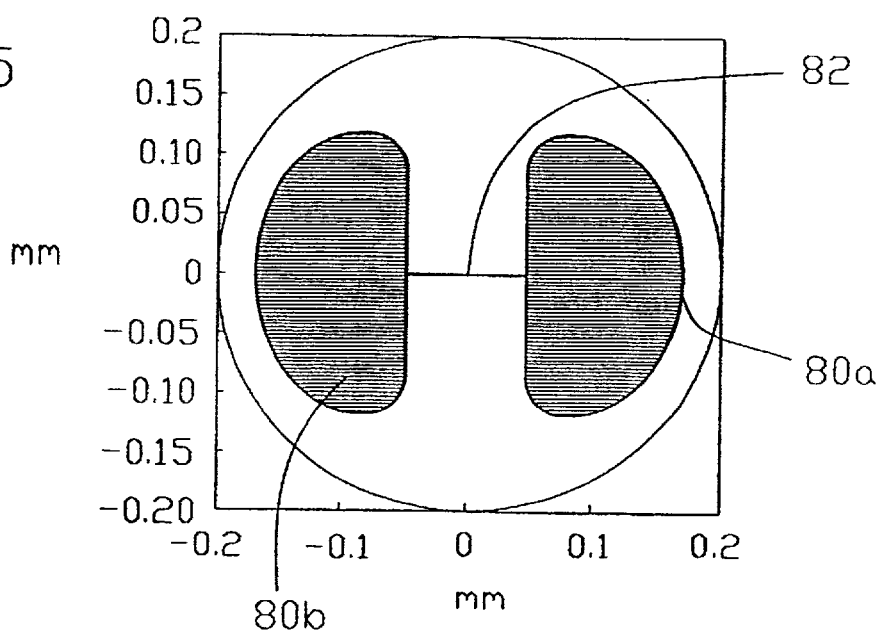
FIG. 5 shows a preferred electrode shape for maximizing the power response of a transducer according to the present invention.

A preferred electrode shape for maximizing the power response of the transducer is shown in FIG. 5, wherein the electrode includes two electrode portions 80a and 80b substantially covering the maximal charge density portions of layer 2, the electrode portions being interconnected by means of a connecting member 82 having a minimal area. Preferably, portions 80a and 80b cover the portions of layer 2 which yield at least a selected threshold (e.g. 30%) of the maximal charge density.

According to the present invention any other parameter may be optimized so as to determine the shape of electrodes 6 and 8. According to further features of the invention described in U.S. patent application Ser. No. 09/000,553, only one electrode (upper electrode 8 or lower electrode 6) may be shaped so as to provide maximal electrical response of the transducer, with the other electrode covering the entire area of layer 2. Since the charge is collected only at the portions of layer 2 received between upper electrode 8 and lower electrode 6, such configuration is operatively equivalent to a configuration including two shaped electrodes having identical shapes.

Figure 6:
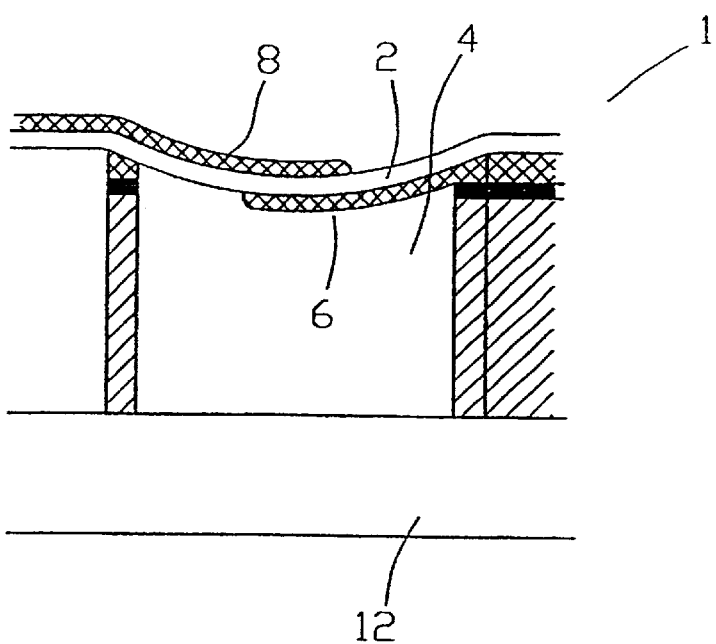
FIG. 6 is a longitudinal section of another embodiment of a transducer element according to the present invention capable of functioning as a transmitter.

Referring now to FIG. 6, according to another embodiment chamber 4 of transducer element 1 may contain gas of substantially low pressure, thereby conferring a substantially concave shape to piezoelectric membrane 2 at equilibrium. Such configuration enables to further increase the electrical response of the transducer by increasing the total charge obtained for a given displacement of layer 2. The total displacement in such an embodiment is given by: $\Psi = P_0 \Psi_{DC} + P \Psi_{AC} \cos \omega t$, wherein $P_0$ is the static pressure differential between the exterior and the interior of cavity 4; $\omega_{DC}$ is the displacement resulting from $P_0$; P is the amplitude of the acoustic pressure; and $\Psi_{AC}$ is the displacement resulting from P.

Accordingly, the strain along the x direction includes three terms as follows:

$$S_{xx} = \left(\frac{\partial \Psi}{\partial x}\right)^2 = P_0^2 \left(\frac{\partial \Psi_{DC}}{\partial x}\right)^2 + P^2 \left(\frac{\partial \Psi_{AC}}{\partial x}\right)^2 \cos^2 \omega t + 2P_0 P \frac{\partial \Psi_{DC}}{\partial x} \frac{\partial \Psi_{AC}}{\partial x} \cos \omega t$$

wherein the DC component is usually filtered out.

Thus, by decreasing the pressure of the medium (preferably air) within cavity 4 relative to the pressure of the external medium (preferably fluid), the value of $P_0$ is increased, thereby increasing the value of the third term of the above equation.

Such embodiment makes it possible to increase the charge output of layer 2 for a given displacement, thereby increasing the voltage, current and power responses of the transducer without having to increase the acoustic pressure P. Furthermore, such embodiment enables to further miniaturize the transducer since the same electrical response may be obtained for smaller acoustic deflections. Such embodiment is substantially more robust mechanically and therefore more durable than the embodiment shown in FIGS. 1a and 1b. Such further miniaturization of the transducer enables to use higher resonance frequencies relative to the embodiment shown in FIGS. 1a and 1b.

Preferably, a transducer element 1 according to the invention described in U.S. patent application Ser. No. 09/000,553 is fabricated by using technologies which are in wide use in the microelectronics industry, so as to allow integration thereof with other conventional electronic components as further detailed hereinunder. When the transducer element includes a substrate such as Copper-polymer laminate or silicon, a variety of conventional electronic components may be fabricated onto the same substrate.

According to a preferred embodiment, a plurality of cavities 4 may be etched into a single substrate 12 and covered by a single piezoelectric layer 2, so as to provide a transducer element including a matrix of transducing cell members 3, thereby providing a larger energy collecting area of predetermined dimensions, while still retaining the advantage of miniature individual transducing cell members 3. When using such configuration, the transducing cell members 3 may be electrically interconnected in parallel or serial connections, or combinations thereof, so as to tailor the voltage and current response of the transducer. Parallel connections are preferably used so as to increase the current output while serial connections are preferably used so as to increase the voltage output of the transducer.

Furthermore, piezoelectric layer 2 may be completely depolarized and then repolarized at specific regions thereof, so as to provide a predetermined polarity to each of the transducing cell members 3. Such configuration enables to reduce the complexity of interconnections between cell members 3.

A transducer element according to the invention described in U.S. patent application Ser. No. 09/000,553 may be further used as a transmitter for transmitting information to a remote receiver by modulating the reflection of an external impinging acoustic wave arrived from a remote transmitter.

Referring to FIG. 6, the transducer element shown may function as a transmitter element due to the asymmetric fluctuations of piezoelectric layer 2 with respect to positive and negative transient acoustic pressures obtained as a result of the pressure differential between the interior and exterior of cavity 4.

A transmitter element according to the present invention preferably modulates the reflection of an external impinging acoustic wave by means of a switching element connected thereto. The switching element encodes the information that is to be transmitted, such as the output of a sensor, thereby frequency modulating a reflected acoustic wave.

Such configuration requires very little expenditure of energy from the transmitting module itself, since the acoustic wave that is received is externally generated, such that the only energy required for transmission is the energy of modulation.

Specifically, the reflected acoustic signal is modulated by switching the switching element according to the frequency of a message electric signal arriving from another electronic component such as a sensor, so as to controllably change the mechanical impedance of layer 2 according to the frequency of the message signal.

Preferably, a specific array of electrodes connected to a single cell member or alternatively to a plurality of cell members are used, so as to control the mechanical impedance of layer 2.

Figure 7D:
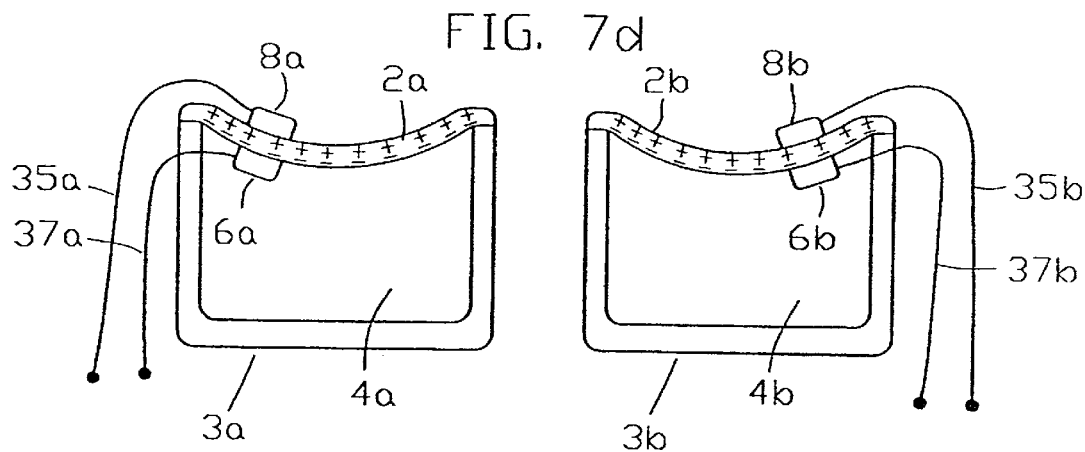

FIGS. 7a–7g illustrate possible configurations for controllably change the impedance of layer 2 of a transmitter element. Referring to FIG. 7a, a transmitter element according to the invention described in U.S. patent application Ser. No. 09/000,553 may include a first and second pairs of electrodes, the first pair including an upper electrode 40a and a lower electrode 38a, and the second pair including an upper electrode 40b and a lower electrode 38b. Electrodes 38a, 38b, 40a and 40b are electrically connected to an electrical circuit by means of conducting lines 36a, 36b, 34a and 34b, respectively, the electrical circuit including a switching element (not shown), so as to alternately change the electrical connections of conducting lines 36a, 36b, 34a and 34b.

Preferably, the switching element switches between a parallel connection and an anti-parallel connection of the electrodes. A parallel connection decreases the mechanical impedance of layer 2, wherein an anti-parallel connection increases the mechanical impedance of layer 2. An anti-parallel connection may be obtained by interconnecting line 34a to 36b and line 34b to 36a. A parallel connection may be obtained by connecting line 34a to 34b and line 36a to 36b. Preferably, the switching frequency equals the frequency of a message signal arriving from an electrical component such as a sensor as further detailed hereinunder.

According to another embodiment shown in FIG. 7b, upper electrode 40a is connected to lower electrode 38b by means of a conducting line 28, and electrodes 38a and 40b are connected to an electrical circuit by means of conducting lines 27 and 29, respectively, wherein the electrical circuit further includes a switching element. Such configuration provides an anti-parallel connection of the electrodes, wherein the switching element functions as an on/off switch, thereby alternately increasing the mechanical impedance of layer 2.

In order to reduce the complexity of the electrical connections, layer 2 may be depolarized and then repolarized at specific regions thereof. As shown in FIG. 7c, the polarity of the portion of layer 2 received between electrodes 40a and 38a is opposite to the polarity of the portion of layer 2 received between electrodes 40b and 38b. An anti-parallel connection is thus achieved by interconnecting electrodes 38a and 38b by means of a conducting line 28, and providing conducting lines 27 and 29 connected to electrodes 40a and 40b, respectively, the conducting lines for connection to an electrical circuit including a switching element.

According to another embodiment, the transmitting element includes a plurality of transducing cell members, such that the mechanical impedance of layer 2 controllably changed by appropriately interconnecting the cell members.

As shown in FIG. 7d, a first transducing cell member 3a including a layer 2a and a cavity 4a, and a second transducing cell member 3b including a layer 2b and a cavity 4b are preferably contained within the same substrate; and layers 2a and 2b are preferably integrally made. A first pair of electrodes including electrodes 6a and 8a is attached to layer 2, and a second pair of electrode including electrodes 6b and 8b is attached to layer 2b. Electrodes 6a, 8a, 6b and 8b are electrically connected to an electrical circuit by means of conducting lines 37a, 35a, 37b and 35b, respectively, the electrical circuit including a switching element, so as to alternately switch the electrical connections of conducting lines 37a, 35a, 37b and 35b, so as to alternately provide parallel and anti-parallel connections, substantially as described for FIG. 7a, thereby alternately decreasing and increasing the mechanical impedance of layers 2a and 2b.

Figure 7E:
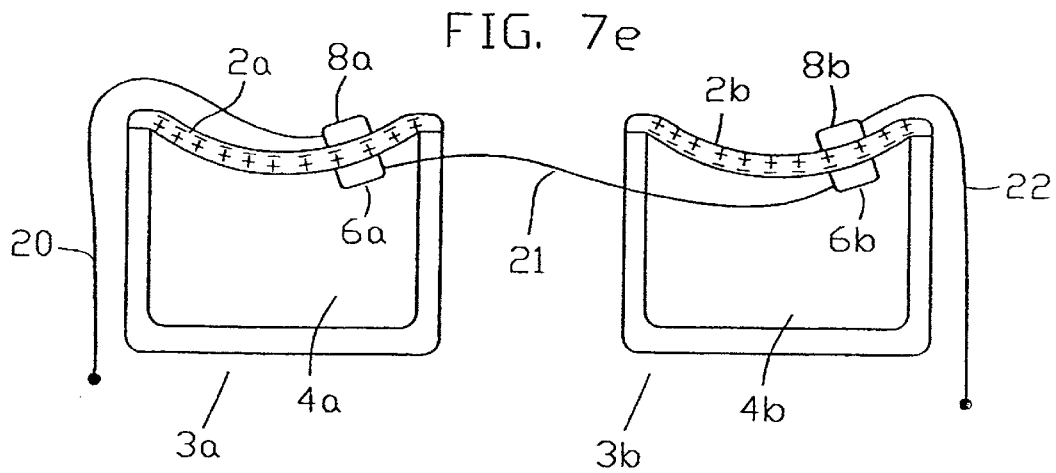

FIG. 7e illustrates another embodiment, wherein the first and second transducing cell members are interconnected by means of an anti-parallel connection. As shown in the Figure, the polarity of layer 2a is opposite to the polarity of layer 2b, so as to reduce the complexity of the electrical connections between cell members 3a and 3b. Thus, electrode 6a is connected to electrode 6b by means of a conducting line 21, and electrodes 8a and 8b are provided with conducting lines 20 and 22, respectively, for connection to an electrical circuit which includes a switching element, wherein the switching element preferably functions as an on/off switch, so as to alternately increase the mechanical impedance of layers 2a and 2b.

Figure 7F:
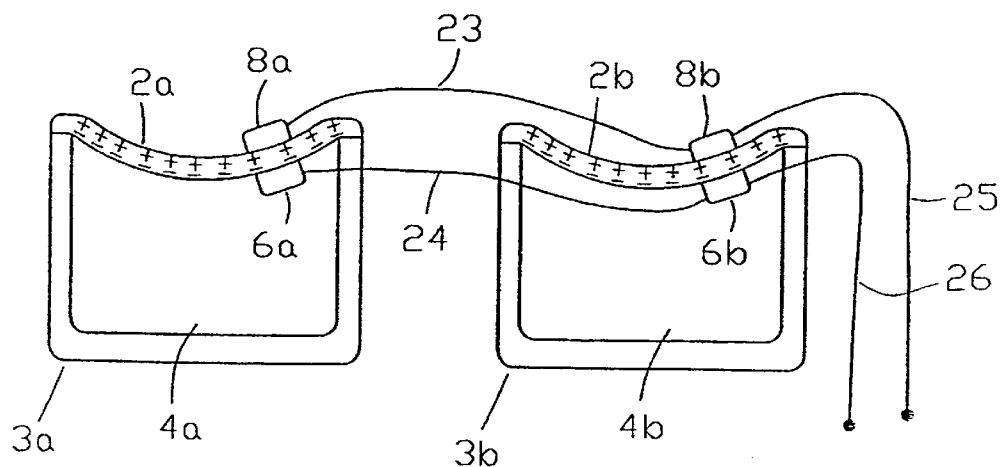

FIG. 7f shows another embodiment, wherein the first and second transducing cell members are interconnected by means of a parallel connection. As shown, electrodes 6a and 6b are interconnected by means of conducting line 24, electrodes 8a and 8b are interconnected by means of conducting line 23, and electrodes 6b and 8b are provided with conducting lines 26 and 25, respectively, the conducting lines for connection to an electrical circuit including a switching element. The switching element preferably functions as an on/off switch for alternately decreasing and increasing the mechanical impedance of layers 2a and 2b.

Figure 8:
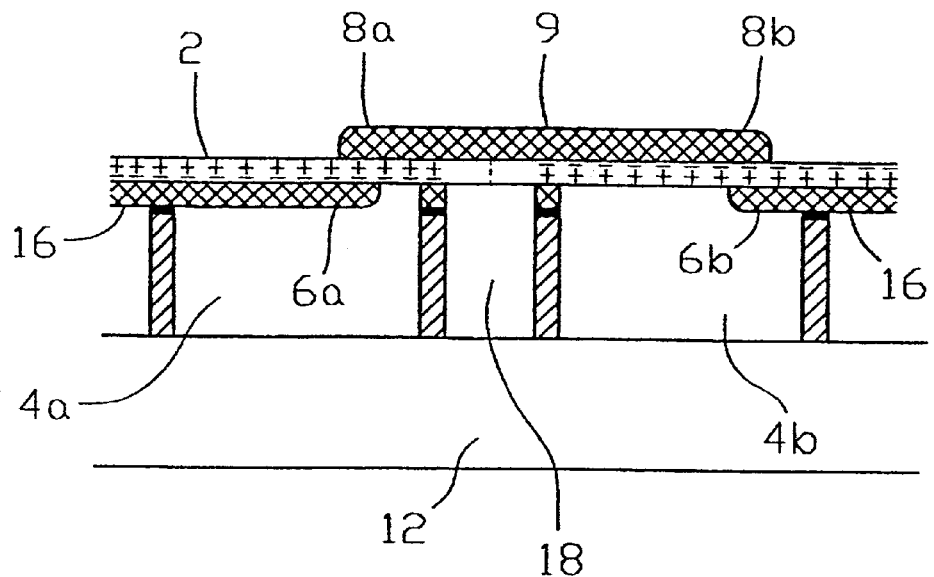
FIG. 8 is a longitudinal section of a transmitter element according to the present invention including an anti-parallel electrical connection.

FIG. 8 shows a possible configuration of two transducing cell members etched onto the same substrate and interconnected by means of an anti-parallel connection. As shown in the Figure, the transducing cell members are covered by a common piezoelectric layer 2, wherein the polarity of the portion of layer 2 received between electrodes 6a and 8a is opposite to the polarity of the portion of layer 2 received between electrodes 6b and 8b. Electrodes 8a and 8b are bonded by means of a conducting line 9, and electrodes 6a and 6b are provided with conducting lines 16 for connection to an electrical circuit.

Figure 9:
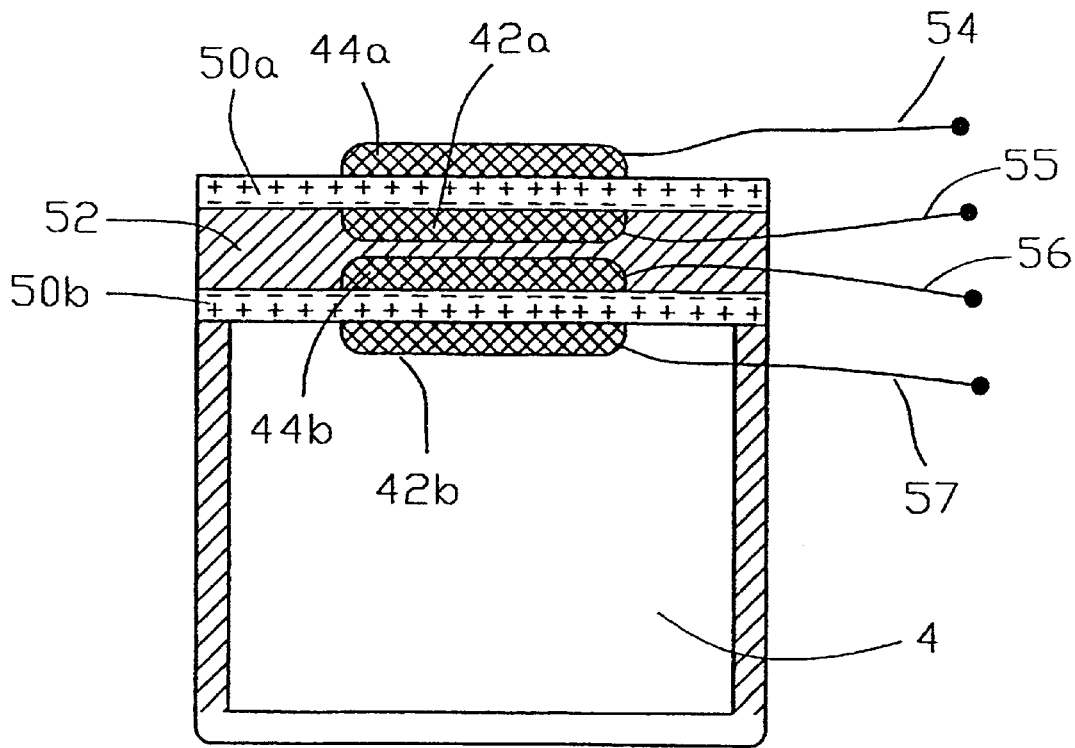
FIG. 9 is a longitudinal section of another embodiment of a transmitter element according to the present invention.

Another embodiment of a transmitter element according to the present invention is shown in FIG. 9. The transmitter element includes a transducing cell member having a cavity 4 covered by a first and second piezoelectric layers, 50a and 50b, preferably having opposite polarities. Preferably, layers 50a and 50b are interconnected by means of an insulating layer 52. Attached to layer 50a are upper and lower electrodes 44a and 42a, and attached to layer 50b are upper and lower electrodes 44b and 42b. Electrodes 44a, 42a, 44b and 42b are provided with conducting lines 54, 55, 56 and 57, respectively, for connection to an electrical circuit.

It will be appreciated that the above descriptions are intended only to serve as examples, and that many other embodiments are possible within the spirit and the scope of invention described in U.S. patent application Ser. No. 09/000,553.

As is detailed hereinunder, in a preferred embodiment, the present invention exploits the advantages of the transducer described hereinabove and in U.S. patent application Ser. No. 09/000,553.

According to the present invention there is thus provided a method of quantifying pulsatile flow in a pipe. The method is effected by executing the following method steps, in which in a first step at least two spaced pressure sensors are directly or indirectly attached onto inner walls of the pipe. In a second step of the method, the spaced pressure sensors are used for recording pressure records associated with each of which. Whereas, in a third step of the method, the pressure records are used for quantifying the pulsatile flow in the pipe.

According to the present invention there is further provided a method of detecting a location of an obstruction in a pipe characterized in pulsatile flow. The method is effected by executing the following method steps, in which in a first step at least two spaced pressure sensors are directly or indirectly attached onto inner walls of the pipe. In a second step of the method, the spaced pressure sensors are used for recording pressure records associated with each of which. Whereas, in a third step of the method, the pressure records are used for detecting the location of the obstruction in the pipe.

According to the present invention there is further provided a method of quantifying a degree of an obstruction in a pipe characterized in pulsatile flow. The method is effected by executing the following method steps, in which in a first step at least two spaced pressure sensors are directly or indirectly attached onto inner walls of the pipe. In a second step of the method, the spaced pressure sensors are used for recording pressure records associated with each of which. Whereas, in a third step of the method, the pressure records are used for quantifying the degree of the obstruction in the pipe.

According to the present invention there is further provided a method which combines at least two of the methods delineated hereinabove. In a triple configuration this method is of quantifying flow, detecting a location of an obstruction and quantifying a degree of the obstruction in a pipe characterized in pulsatile flow. The method is effected by executing the following method steps, in which in a first step at least two spaced pressure sensors are directly or indirectly attached onto inner walls of the pipe. In a second step of the method, the spaced pressure sensors are used for recording pressure records associated with each of which. Whereas, in a third step of the method, the pressure records are used for quantifying the pulsatile flow in the pipe, for detecting the location of the obstruction in the pipe and for quantifying the degree of the obstruction in the pipe.

Further according to the present invention there is provided a system for quantifying pulsatile flow in a pipe. The system includes at least two pressure sensors which serve for recording pressure records from within the pipe. The system further includes a mechanism for attaching the pressure sensors onto inner walls of the pipe in a spaced configuration and a processing module for receiving pressure records from each of the pressure sensors and for quantifying the pulsatile flow in the pipe.

Further according to the present invention there is provided a system for detecting a location of an obstruction in a pipe characterized in pulsatile flow. The system includes at least two pressure sensors which serve for recording pressure records from within the pipe. The system further includes a mechanism for attaching the pressure sensors onto inner walls of the pipe in a spaced configuration and a processing module for receiving pressure records from each of the pressure sensors and for detecting the location of the obstruction in the pipe.

Further according to the present invention there is provided a system for quantifying a degree of an obstruction in a pipe characterized in pulsatile flow. The system includes at least two pressure sensors which serve for recording pressure records from within the pipe. The system further includes a mechanism for attaching the pressure sensors onto inner walls of the pipe in a spaced configuration and a processing module for receiving pressure records from each of the pressure sensors and for quantifying the degree of the obstruction in the pipe.

According to the present invention there is further provided a system which combines at least two of the systems delineated hereinabove. In a triple configuration this system is for quantifying flow, detecting a location of an obstruction and quantifying a degree of the obstruction in a pipe characterized in pulsatile flow. The system includes at least two pressure sensors which serve for recording pressure records from within the pipe. The system further includes a mechanism for attaching the pressure sensors onto inner walls of the pipe in a spaced configuration and a processing module for receiving pressure records from each of the pressure sensors and for quantifying the pulsatile flow in the pipe, for detecting the location of the obstruction in the pipe and for quantifying the degree of the obstruction in the pipe.

According to a preferred embodiment of the present invention any of the above systems further includes a non-invasive activatable transducer element for communicating data from within the pipe to a receptive transducer located outside thereof. According to this preferred embodiment of the present invention, any of the above methods is further effected by using a non-invasive activatable transducer element for communicating data from within the pipe to a receptive transducer located on the outside thereof.

According to a preferred embodiment of the present invention the non-invasive activatable transducer is an acoustic activatable transducer element, such as, but not limited to, the above described transducer element, which is further described in U.S. patent application Ser. No. 09/000, 553. However, the scope of the present invention is not limited to acoustic transducers. Other activatable transducers are known in the art. For example, a radio frequency activatable transducer, a capacitance activatable transducer, etc. Such transducers are further described in, for example, in WO 9829030, which is incorporated by reference as if fully set forth herein. Active, battery operated, transducers are also within the scope of the present invention, although, at present less advantageous, because of the limited life span of a battery.

The mechanism for attaching the pressure sensors onto the inner walls of the pipe in a spaced configuration can involve direct attachment of each of the sensors in a predefined location along the pipe. However, according to a preferred embodiment of the present invention a platform which serves for holding the pressure sensors and which by itself is insertable into the pipe is employed. Depending on the application, such a platform can come in different configurations. For example, when any of the systems or methods according to the present invention is practiced in a pipe of a plumbing constriction characterized by pulsatile flow, such as cooling installations in nuclear reactors, in which pulsatile flow of a coolant is effected by a pulsative pump, then the platform can be a sleeve insertable into the installation. When, on the other hand, any of the systems or methods according to the present invention is practiced in a blood vessel characterized by pulsatile flow effected by a pulsating heart, then the platform can be a stent insertable into the blood vessel. The blood vessel can be a damaged vessel, a graft or an artificial blood vessel. In the latter case, the artificial vessel can serve also as the platform.

Figure 10A:
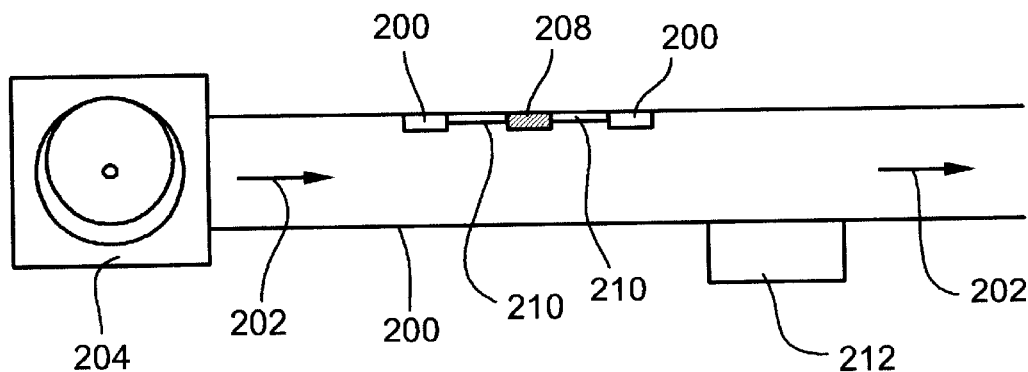
FIG. 10a presents a schematic cross sectional depiction of a preferred embodiment of the system according to the present invention when implemented in a pipe characterized by pulsatile flow.

A system according to any of the above configurations is schematically depicted in FIG. 10a. The system is implemented in a pipe 200. As indicated by arrows 202, pipe 200 is characterized by a pulsatile flow of a fluid therein, which is effected by a pulsative pump identified by 204. Two pressure sensors 206 are attached to the inner walls of pipe 200. Each of the sensors is designed to record pressure records if faces as a function of time. Further description of the pressure sensors is provided hereinunder. Sensors 206 communicate with an activatable transducer element 208. Communication is effected by wires 210. Element 208 serves for communicating data from within pipe 200 to a receptive transducer 212 located outside pipe 200. Transducer 212 serves two functions. Its first function is to activate element 208 to provide sensors 200 with power for their operation and to enable element 208 to transmit data. Its second function is to retrieve data from element 208. Therefore, according to the present invention element 208 and transducer 212 are selected functionally compatible. One example is described hereinabove, wherein element 208 is an acoustic transducer, namely it can transform acoustic energy into electric energy and vice versa. In this case, transducer 212 is also selected to include an acoustic transducer, such that, on one hand, by providing element 208 with acoustic energy transmitted thereto via pipe 200 and/or the fluid therein element 208 generates electric energy which serves for its own operation and the operation of pressure sensors 206, whereas, on the other hand, that electrical power enables element 208 to generate acoustic energy which is transmitted therefrom via pipe 200 and/or the fluid therein to transducer 212. The acoustic signals received by transducer 212 are then retransformed into electric signals which can be used for calculating the various parameters as further detailed in the Examples section below. However, other functionally compatible element 208/transducer 212 pairs are know in the art, as further delineated hereinabove.

As used herein in the specification and in the claims section below the term "pipe" refers to a hollow body used for the conveyance of a fluid, either liquid or gas. The term thus reads upon "biological pipes" such as blood vessels.

As used herein in the specification and in the claims section below the term "pulsatile flow" refers to a flow characterized in rhythmic change of pressure.

As used herein in the specification and in the claims section below the term "pulsative pump" refers to a pump capable of generating a pulsatile flow in a pipe. The heart is know to functions as a pulsative pump, resulting in diastolic and systolic flows and pressures in blood vessels.

As used herein in the specification and in the claims section below the term "constriction" also refers to blockage. It is measured, for example, in percents of blockage.

Figure 10B:
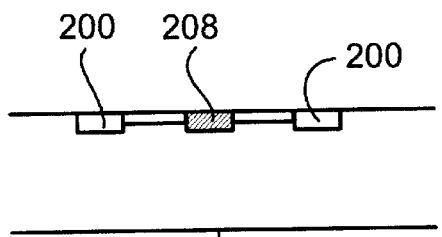
FIG. 10b presents a schematic cross sectional depiction of a preferred embodiment of the system according to the present invention when implemented on a platform insertable into a pipe characterized by pulsatile flow.

As used herein in the specification and in the claims section below the term "stent" refers to a tube or the like used for inserting in a blocked vessel or other part. FIG. 10b shows a portion of a platform (stent or sleeve) 214 onto which sensors 200 and element 208 are operationally attached. Platform 214 is insertable into a pipe, e.g., a blood vessel.

Further according to the present invention there is provided a method of non-invasively quantifying pressure in a pipe. The method is effected by executing the following method steps, in which, in a first step at least one pressure sensor is attached onto the inner walls of the pipe. At least one non-invasively activatable transducer element is also attached into the inner walls of the pipe. Communication is provided between the pressure sensor(s) and the transducer element(s). The pressure sensor(s) are used for recording pressure records within the pipe. The non-invasively activatable transducer element(s) are used for retrieving pressure records from the sensor(s) and for communicating these records to an outside receptive transducer, functionally compatible therewith. It will be appreciated that according to this configuration the flow within the pipe can be either pulsatile or non-pulsatile.

Figure 10C:
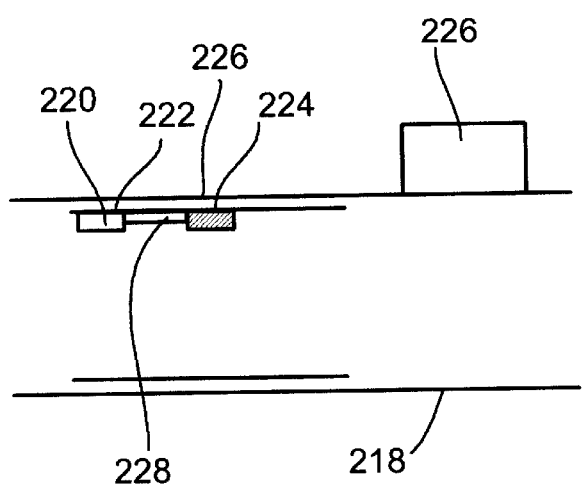
FIG. 10c presents a schematic cross sectional depiction of a preferred embodiment of the system according to the present invention when implemented in a pipe characterized by pulsatile or non-pulsatile flow.

Further according to the present invention there is provided a system for non-invasively quantifying pressure in a pipe 218. As shown in FIG. 10c, the system includes at least one pressure sensor 220 for recording pressure records in the pipe. The system further includes a first mechanism 222 for attaching pressure sensor(s) 220 onto the inner walls of pipe 218. The system further includes at least one non-invasively activatable transducer element 224 and a second mechanism 226 for attaching element(s) 224 onto the inner walls of pipe 218. The system further includes a communication medium 228, wires in this case, for communicating between pressure sensor(s) 220 and transducer element 224, for retrieving pressure records therefrom and for communicating the pressure records to an outside receptive transducer 226. Non-invasively activatable transducer element is preferably an acousto activatable transducer element as further detailed hereinabove.

Figure 10D:
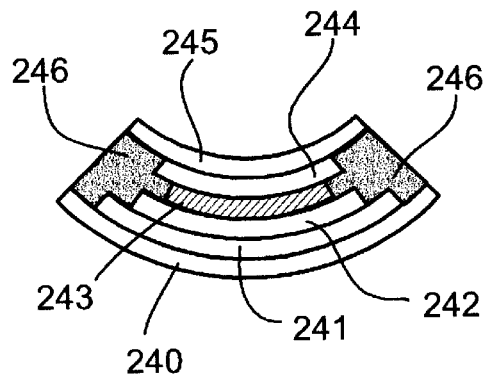
FIG. 10d presents a schematic cross sectional depiction of a preferred embodiment of a PVDF based pressure sensor according to the present invention.

FIG. 10d provides a schematic depiction of a preferred pressure sensor according to the present invention.

It includes a metalic substrate 240, e.g., steell, bent to fit the inner radius of a pipe. Substrate 240 has gold plated surfaces to prevent clotting and provide for better adhesion to additional layers of the sensor as further described below. It further includes a PVDF sensing element 243 supplemented with electrodes, e.g., CuNi electrodes. On both sides, element 243 is covered by insulating layers 242 and 244, each of which is covered with a conductive layer 241 and 245, respectively which provide for the required electrical decoupling from the conductive fluid in the pipe, according to Faraday. Epoxy glue may serve both to adhere the layer thus described to one another and to provide for insulation from the sides.

Each of the various embodiments and aspects of the present invention as delineated hereinabove and as claimed in the claims section below finds experimental support in the Examples section that follows.

EXAMPLES

Reference is now made to the following examples, which together with the above descriptions, illustrate the invention in a non limiting fashion.

Example 1

Effects of Constrictions on the Properties of Pulsatile Flow of Liquids in Elastic Vessels—Theoretical Considerations Blood flow in the arteries is pulsatile. Blood is ejected from the left ventricle of the heart into the aorta, and the entire vascular system, in sharp pulses. The pulsatile nature of the flow manifests as sharp, periodic fluctuations in the instantaneous blood pressure, as well as in the flow velocity along the arteries.

When a blood vessel is obstructed, the flow rate through the vessel decreases. When this occurs in a coronary artery, ischemia of the heart muscle can result.

The purpose of the following series of experiments is to determine whether and to what degree the degree of constriction of a blood vessel can be determined from instantaneous pressure measurements at various points along its length.

In these experiments a coronary artery was modeled by a flexible latex tube, and the properties of a pulsatile flow of water through constrictions formed in the tube were studied using the system according to the present invention.

The theory of pulsatile flow of a liquid or a gas through a pipe is essentially one of acoustics, with certain modifications.

Let the radius of the pipe be $\alpha$, and let the liquid be characterized by a density $\rho$ and a free-field sound velocity $c_0$. Using the cylindrical coordinate system (x,r,$\theta$), where x denotes the direction along the pipe length, and (r,$\theta$) lie in the pipe cross-section, the flow is characterized everywhere by a time-and-position dependent pressure P(r,$\theta$,x,t) and the particle velocity (not to be confused with sound velocity) is $\vec{v}$(r,$\theta$,x,t).

Interest is given herein almost exclusively to cases wherein the diameter of the pipe is much smaller than any acoustic wavelength possible in the medium. This means that, in all but a few cases, any pressure variations in the (r,$\theta$) plane will equilibrate very rapidly, so that the pressure can be considered to be constant in that plane. Consequently, in this approximation the pressure is a function of x only, and the velocity has only one significant component, $v_x$. In the following the x subscript is therefore dropped, and the particle velocity in the x direction is simply denoted by v.

A further approximation which may be made is that v is also constant along the (r,$\theta$) plane. This approximation is usually violated only very near the vessel boundaries, where viscous effects give rise to a dissipative boundary layer. This layer is however very thin, and so can be neglected when dealing with large (a few mm in diameter or more) vessels.

The propagation of a pressure pulse along a blood vessel is described by means of two equations. The first is the continuity, or preservation of mass, equation, while the second is Newton's second law of mechanics (equality of forces). In free space, and in a perfectly rigid pipe, the result is the acoustic wave equation, which describes propagation of sound waves with a constant velocity $c_0$, $$\frac{\partial^2 P(x,t)}{\partial x^2} - \frac{1}{c_0^2}\frac{\partial^2 P(x,t)}{\partial t^2} = 0$$

where P is the pressure, x is the displacement and t is the time.

In the present case, the propagation of pressure pulses is monitored in a pipe which is elastic (as opposed to rigid). In such a case, there are two additional effects which come into play. The first is the fact that an increase in fluid pressure causes an expansion of the pipe walls. This translates into an effective compressibility of the fluid which is much greater than the bulk value. The second effect is the inclusion of inertial forces resulting from the concomitant acceleration of the pipe walls, which are not massless, as they expand and contract. Both these effects taken together significantly modify the speed of sound inside the pipe. Thus the speed of sound inside a substantially flexible pipe is given by:.

$$c \approx \sqrt{\frac{Eh}{2a\rho}}\left[1 - \left(\frac{\omega}{\omega_c}\right)^2\right], \omega_c = \sqrt{\frac{E}{\rho_w a^2}}$$

where $\rho$, E, h are the density, elastic modulus and thickness of the pipe walls, respectively, and $\rho_w$ is the density of the liquid.

One can see that the speed of sound is frequency-dependent, i.e., the medium is dispersive. However, this is significant only around and above the cutoff frequency $\omega_c$, which is usually above the frequency range of interest here. For low frequencies, consequently, one has an almost non-dispersive medium with a sound speed much lower than that of the bulk liquid. For example, while the free-field sound velocity in water is approximately 1500 m/sec, the velocity in a typical latex rubber tube which was used for modeling the present invention is only 16 m/sec, and in the arterial system it is even lower, about 3–5 m/sec.

The purpose of this modeling experiment is to determine the effects of constrictions on the measured parameters: pressure and pressure gradients. When a traveling pressure pulse encounters a constriction, part of the pulse is reflected back, while the remainder travels on. An idea of the mechanism can be obtained by modeling the pipe as a one-dimensional acoustic transmission line. Parameters of the flow in the line are the pressure P and the flow rate V (which is the flow velocity v integrated over the pipe cross-section). The relation between the pressure and the flow rate is analogous to the relation between voltage and current in electrical systems, and is given in an unobstructed pipe by the impedance relation:

$$P = \frac{\rho c}{A}V$$

where A is the cross-section area of the pipe.

When a constriction is encountered, the cross-section of the vessel changes, sometimes along with the speed of sound c due to changes in the properties of the wall. Consequently, the acoustic impedance changes abruptly at the interface between the pipe and the constriction. This impedance change causes a partial reflection, the dimension of which depends on the degree of constriction, and to a lesser extent on its shape.

In the absence of a constriction, the traveling pressure pulse can be described by the generic form $f(x-ct)$, where ƒ(x) describes the shape of the pressure pulse. The presence of a constriction gives rise to a reflection. Let one define the origin of the reflection to be at the point of the constriction. Then, the pressure pulse at sensor position x becomes ƒ(x−ct)+Rƒ(−x−ct) for the case of negative x (distal constriction), and Tƒ(x−ct) for positive x, or proximal constriction (this formulation ignores possible shape distortions, which do exist but are not crucial for understanding the effect).

The result is the following. In the proximal case, a constriction's main effect will be to lower the amplitude of the transmitted wave, while the change in the wave's shape will be minimal. This is not the case for distal constrictions. There, a pressure sensor will pick up the superposition of the incident and the reflected waves. The amplitude of the received pulse will therefore increase as the constriction grows more severe, in contrast to the proximal case, where the pulse amplitude will decrease. Additionally, the pulse shape will be modified.

By including two closely spaced pressure sensors in the system it is possible to measure not only the pressure, but also the pressure gradient. This is a useful thing to do, for the following reason. Consider a section of length dx of liquid inside the pipe. The mass of this section is given by m=ρAdx, the mean acceleration is given by ∂(v)/∂t, and the longitudinal force operating on this section of pipe is F=A[P(x,t)−P(x+dx,t)]≈−A(∂P/dx)dx. These quantities are related via Newton's second law, F=m(v̇), or, $$\langle v(t) - v(t_0) \rangle \approx \frac{1}{\rho} \int_0^t [P(x, t') - P(x + dx, t')] dt'$$

wherein the left term in the equation is the mean velocity difference between time point t and time point $t_0$.

Consequently, by measuring the instantaneous pressure at two nearby points one can calculate the mean flow rate across these two sensors, since the density ρ is known.

To illustrate this, consider the case of a distal constriction, i.e., a sensor positioned at x<0 and a constriction at the origin. The pressure for such a case is, as described above, P(x,t)=ƒ(x−ct)+Rƒ(−x−ct). One assumes that at time $t_0$ prior to the pulse, the velocity vanishes, and for simplicity of notation drop the limits of the integration. In such a case, the velocity will be:

$$v(x, t) = -\frac{1}{\rho} \int \frac{\partial P(x, t')}{\partial x} dt' = \frac{1}{\rho c}[f(x - ct) - Rf(-x - ct)]$$

If R is positive, as is usually the case, one sees that even though the pressure near the constriction increases, still the velocity decreases, as physically it should. A point to note is that, if ƒ(x) describes a pulse with a well-defined beginning, it will take a time Δt=2|x|/c for the pressure and velocity to reach their equilibrium values, since for this to happen the leading edge of the pulse must travel at least from the sensor to the obstruction and back.

From the above derivation one learns that, once the velocity v is known, another quantity, the acoustic impedance, defined as the ratio between the pressure and the velocity, also become available.

Consider first an unobstructed pipe. There, the pressure, velocity and impedance are given by:

$$P(x, t) = f(x - ct); v(x, t) = \frac{1}{\rho c} f(x - ct);$$

$$Z(x, t) \equiv \frac{P(x, t)}{v(x, t)} = \rho c \equiv Z_0$$

The quantity $Z_0$ is known as the characteristic impedance of the medium, which includes both the liquid and the vessel properties (recall that c is determined by the elastic properties of the vessel walls).

One now defines the time-domain relative impedance by:

$$\zeta(x, t) \equiv \frac{1}{\rho c} \frac{P(x, t)}{v(x, t)}$$

The x parameter is can be dropped, as the place of measurement is obvious. From the above derivation this parameter should be roughly unity for an unobstructed pipe. For a distal constriction, however, one obtains:

$$\zeta(x, t) = \frac{f(x - ct) + Rf(-x - ct)}{f(x - ct) - Rf(-x - ct)} \geq 1$$

Thus, this parameter is sensitive to the presence of reflection arising from distal constrictions. Moreover, the point of departure from unity can in principle tell the value of x, i.e., the distance between the constriction and the sensor.

A point to be made is that such an impedance measurement characterizes the vessel from the measurement point onwards only. Thus, the impedance will change in the presence of a distal or midway constriction, but will be unaffected by proximal constrictions. Another point is that the impedance will not change of the original pulse height changes, since it is a normalized quantity which characterizes the vessel only. It is, in principle, sensitive to the pulse shape, but this sensitivity is not great for a wide variety of shapes.

Example 2

Experimental Protocol

Figure 11:
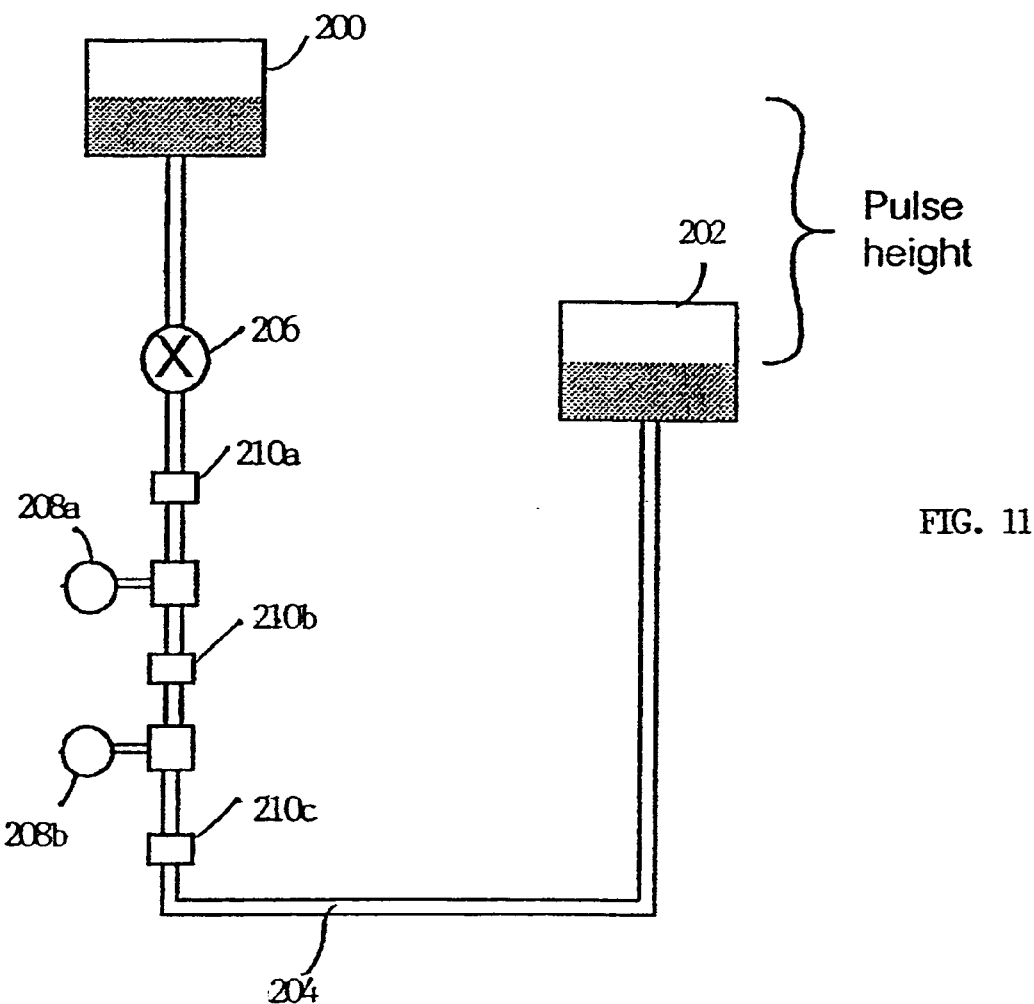
FIG. 11 is a schematic depiction of the experimental model employed to reduce the present invention to practice.

The experimental system used herein is described in FIG. 11. It is based on a computer-controlled electrical valve, which connects via a pipe a high water reservoir to a lower-pressure system. As depicted in FIG. 11, it thus includes two water tanks 200 and 202, connected therebetween via a pipe 204. A computer-controlled electrical valve 206 is implemented on pipe 204, as well as two proximate pressure sensors 208a and 208b. Locations of proximal, midpoint and distal constrictions are indicated by 210a, 210b and 210c.

The electric valve is an on-off, normally closed solenoid-operated valve. It requires a 12V 1A DC power source, which is supplied by a commercial power supply. It is controlled by a custom-build control box, which contains a relay operated from a TTL 5V external control signal, as well as various switches and indicators. The valve opens quite rapidly, taking no more than 10–15 msec to open completely. Closure is slower, and the valve takes roughly 50 msec to close after power has been cut off. Both opening and closing are accompanied by audible impact noises as the armature reaches the end of its free path at its respective end. These impact noises are picked up also by the various pressure sensors in the system.

The pipe used in the system is a flexible latex tube, with an inner diameter of 5.25 mm and a wall thickness of 1.25 mm. The speed of sound inside this pipe has been measured to be c≈16 m/sec. Following the sensor and constriction complex, the pipe continues for about 5 m before connecting to the lower water reservoir. This arrangement gives roughly 600 msec between the arrival of the pulse and the first reflection from the termination of the system, more than enough time to perform all the required measurements on an effectively reflection-free system.

The system includes two commercial Biometrix UTR-Disposable AS-0013 pressure transducers, based on a membrane-mounted strain gauge bridge technology. These sensors are customarily used to measure instantaneous blood pressure via a catheter, and are here connected to the system via custom-built, plastic "T" fittings. The sensors have a calibrated sensitivity of 5 $\mu$V/V. The amplifiers used with these sensors are custom-built differential two-stage amplifiers, with a flat frequency response between 0.2 Hz and 1 KHz, and a 3 dB/octave rolloff outside this range.

Additionally, the system can incorporate up to two Telesense custom-built piezoelectric pressure transducers, which are inserted directly into the pipe at desired locations. The sensors are based on a flat piezoelectric PVDF sheet, attached to a rigid gold-plated metal curved body and insulated from the surrounding water. Attached to the sensor from above is a gold-plated polymer sheet, which is electrically connected to the lower metal body and to an external wire, and together with the body forms an electromagnetic shield for the active PVDF sheet. The sensor is connected via a twisted pair of 0.1 mm enameled copper wires to a B&K 2661 charge preamplifier, and from there to a custom-built line amplifier.

The line amplifier is a standard two-stage constriction, with a flat frequency response between 0.2 Hz and 1 KHz, and a 3 dB/octave rolloff outside this range. However, the preamplifiers have a built-in highpass filter, with 3 dB falloff at 0.45 Hz and a 6 dB/octave rolloff below.

Figure 12:
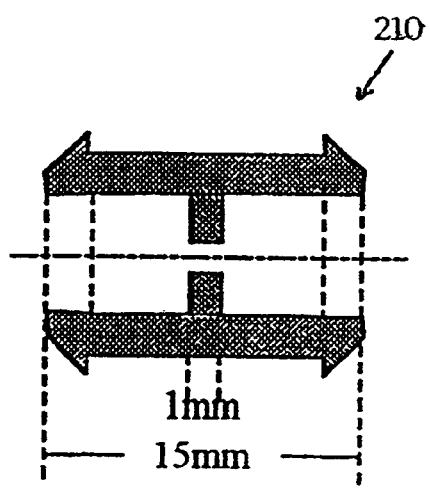
FIG. 12 is a cross section of a constriction employed with the model of FIG. 11.

Constrictions are constructed from plastic (Darylin) fittings of a shape as depicted in FIG. 12. The flexible latex hose fits elastically on the ends of the constrictions. The constrictions are available in the following diameters: 5 mm (completely open), and 4, 3.5, 3, 2.5, 2, 1.5, 1, and 0.5 mm.

The system has three prepared places for the inclusion of constrictions. The first is upstream from all the sensor assemblies, or proximal to the sensors, the second is midway between the two sensors, which emulates an intra-stent occlusion, and the third is downstream from the sensors (distal).

The entire system is controlled by hardware and software installed on a standard PC—a 166 MHz Pentium computer with 64 MB of memory and 2.1 GB hard disk, running the Windows95 operating system. The computer handles both the control and triggering operations and the data acquisition, processing, storage and display.

The interface between the experimental system and the controlling PC is via a Data Translation 3010 data acquisition card (DACC). This card plugs into one of the PCI slot of the PC, and supplies 32 single-ended (or 16 differential) 12-bit analog input channels, 2 differential analog output channels, 16 digital I/O lines and 4×16-bit (or 2×32-bit) counter-timers. The maximal throughput of the A/D channels is 1 Msamples/sec. Since in this experiment a maximum of 6 simultaneous input channels are used, this gives a maximal sampling frequency of 167 KHz, or a maximal Nyquist frequency of roughly 80 KHz at each channel, far higher than one requires. Additionally, in the configuration used in this experiment, the counter-timers are daisy chained to generate the pulses which trigger the electric valve.

The DACC can be controlled with the help of a set of DLLs supplied by the manufacturer. These DLLs are invoked by a program, named PULSER, written at Telesense. The program is written in 16-bit Turbo Pascal for Windows 1.5. It supplies an interactive dialog by which the various parameters of the DACC can be controlled. Additionally, it supplies a DDE interface via which the program (and consequently the DACC) can be controlled by any DDE-capable application.

In the present experiment, PULSER is used solely to provide a DDE link to the DACC. The actual control, processing, display and storage is performed via an interactive graphical program, written and implemented in MATLAB™ 5.1 (which has built-in DDE capabilities). As in most MATLAB GUI programs, it is divided into two main program files (M files in MATLAB jargon). The first, PULSE_GUI.M, builds the GUI and connects callback routines to the various controls, after which it terminates. It also restores the controls to their previous settings. The second program, PULSE_RUN.M, is invoked whenever a control is activated. This is the program which does the actual work, operating the DDE link, processing and displaying the sampling results, etc.

The program enables interactively setting the pulse length, sampling parameters, sampled channels and gains, and repetition parameters. It also determines the displayed traces, in a fairly flexible manner. Finally, it also internally stores the sampled raw data, which may later be accessed and placed in permanent storage for later analysis. During the program operation, all the data is available and accessible from the MATLAB interactive command window as well, so that quite intricate processing and display operations can be performed on-line at the discretion of the operator.

The MATLAB code also includes provisions for filtering out unwanted electromagnetic noise, without harming like frequency components of the desired signal. One feeds into one of the sampling channels a reference signal, obtained by connecting a short antenna to a charge amplifier. This reference signal is then subtracted from the other channels using an advanced adaptive LMS noise-canceling algorithm.

Example 3

Experimental Procedure The experiment itself is divided into 3 runs as follows:

Run A—Proximal constrictions.

In this run constrictions are placed proximal (upstream) to the sensor assembly.

Run B—Midway constrictions.

In this run constrictions are placed in the middle between the pairs of sensors.

Run C—Distal constrictions.

In this run constrictions are placed distal (downstream) from the sensor assembly.

The experimental procedure for each of the runs is as follows:

Perform a measurement for an open constriction. This is the baseline for comparison.

Perform a measurement for constriction diameters 3, 2.5, 2, 1.5, 1, 0.5 mm. Save the two narrowest openings for last, as they are the most difficult to perform.

A measurement consists of the following steps:

Fit the desired constriction at the proper place.

Open the taps to let water flow through the constriction. Make sure that all the air bubbles come out. This is rather difficult to do for the 0.5 mm constriction, and possibly for the 1 mm constriction, which is why those are left last.

Trigger a series of pulses to stabilize the system and get a feel for the quality of the data.

Record the sensors' response to one or more pulses.

Save the display as hard copy (if possible) and as a saved figure on the hard disk. Save the raw data on the hard disk as well.

In addition to the hard disk, data will be backed up onto a ZIP drive. Files will be labeled by the run (A,B,C) and constriction diameter in steps of 0.1 mm.

Example 4

Experimental Results

All runs in the experiment used the following parameters:

Electrical pulse width—400 msec.

Sampling frequency—2000 Hz.

Sampled interval—from −100 msec to +1000 msec relative to the beginning of the electrical pulse.

Smoothing—convolution with a 10 msec wide Hamming window.

Averaging—average over 5 pulses spaced 6 msec apart (to let the transients die out between the pulses).

Adaptive noise canceling—active for the PVDF sensor channels (no electrical noise was apparent on the Biometrix sensor channels).

Figure 13:
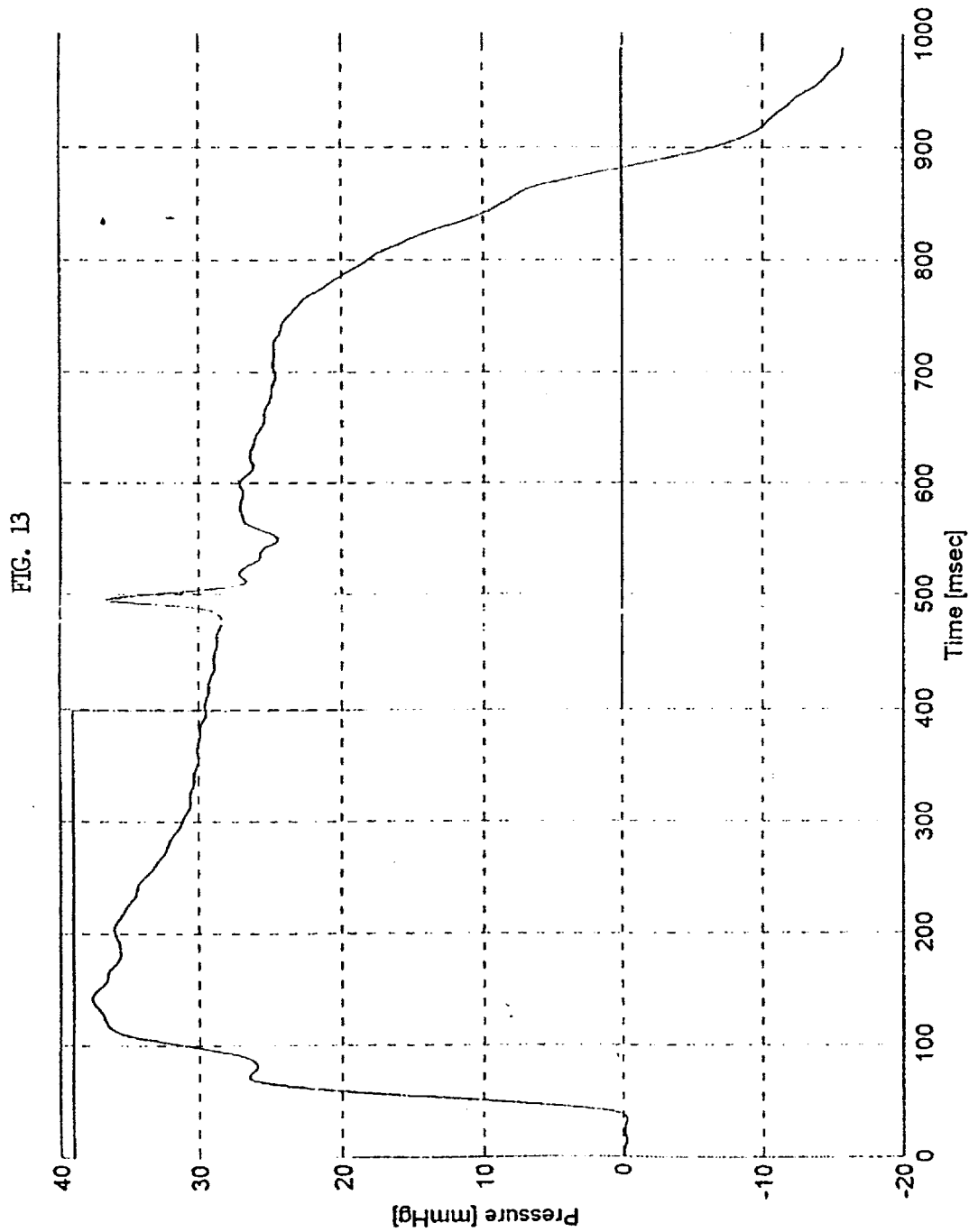
FIG. 13 shows a pressure pulse measured by a Biometrix sensor for an open pipe and a 400 msec valve control. Above, the control signal. Below, the pressure pulse.
Figure 14B:
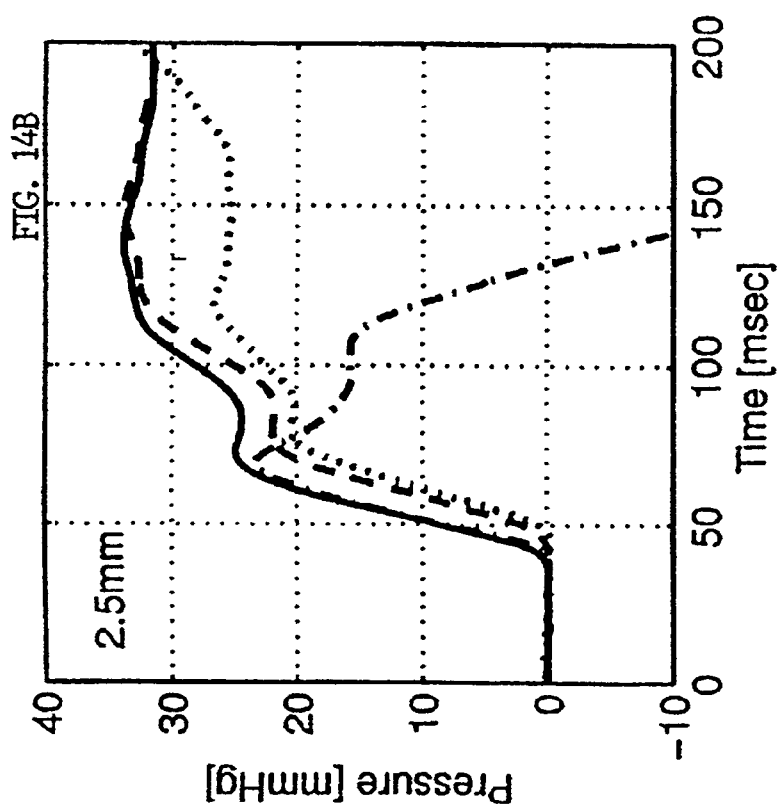
Figure 14A:
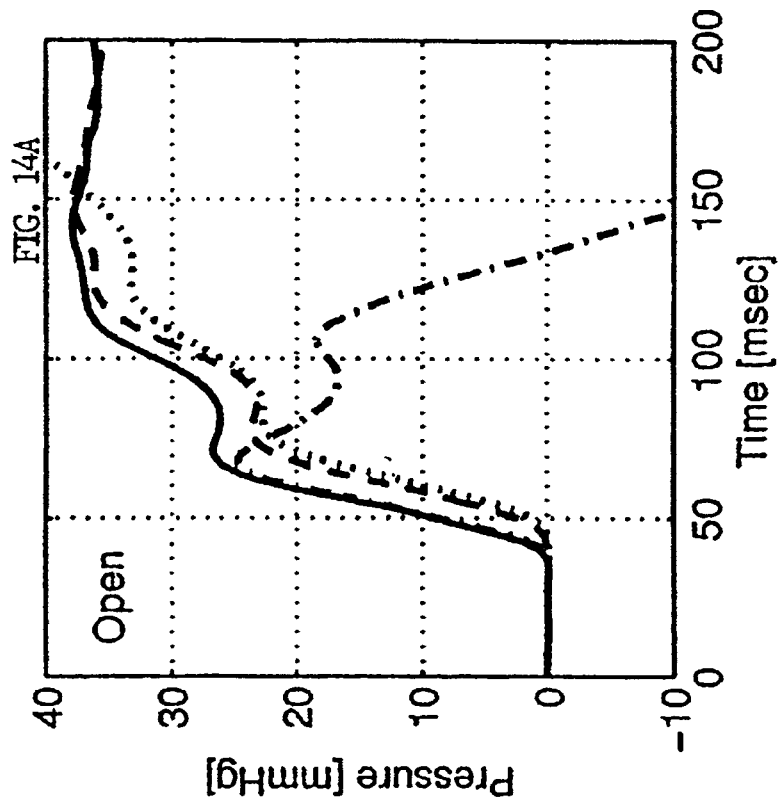
Figure 14D:
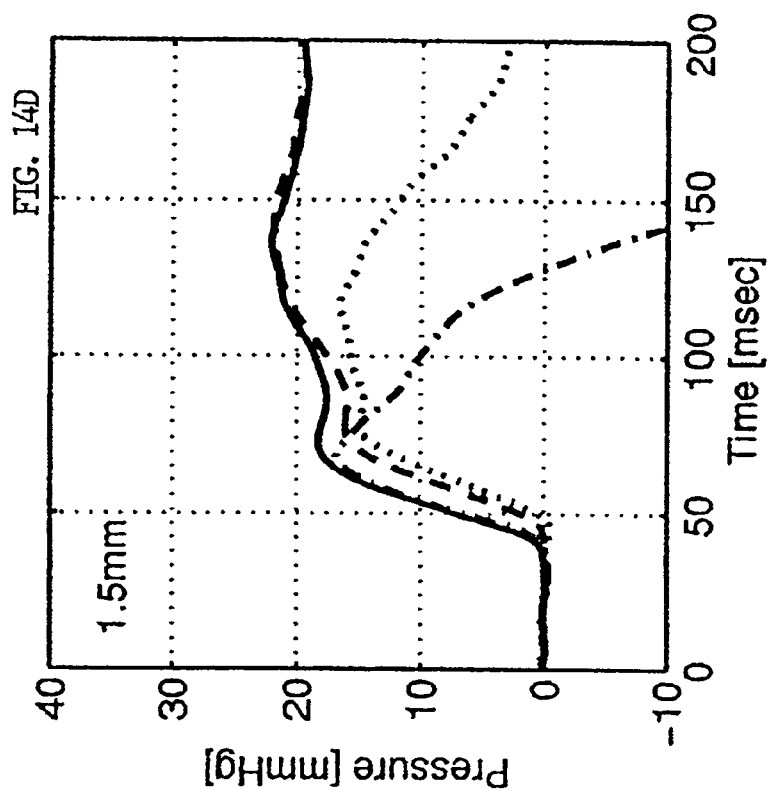
Figure 14C:
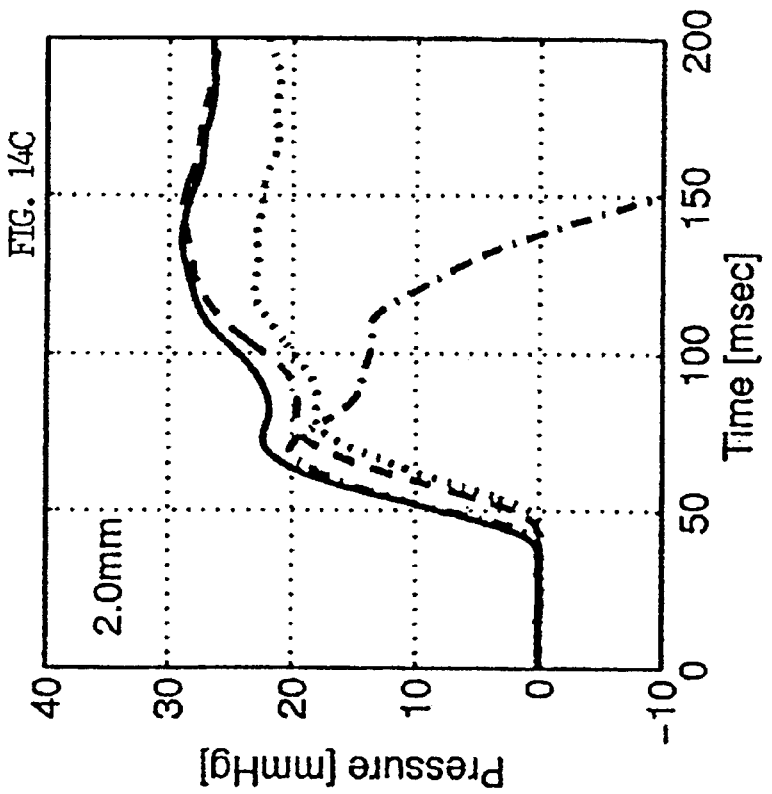
Figure 15B:
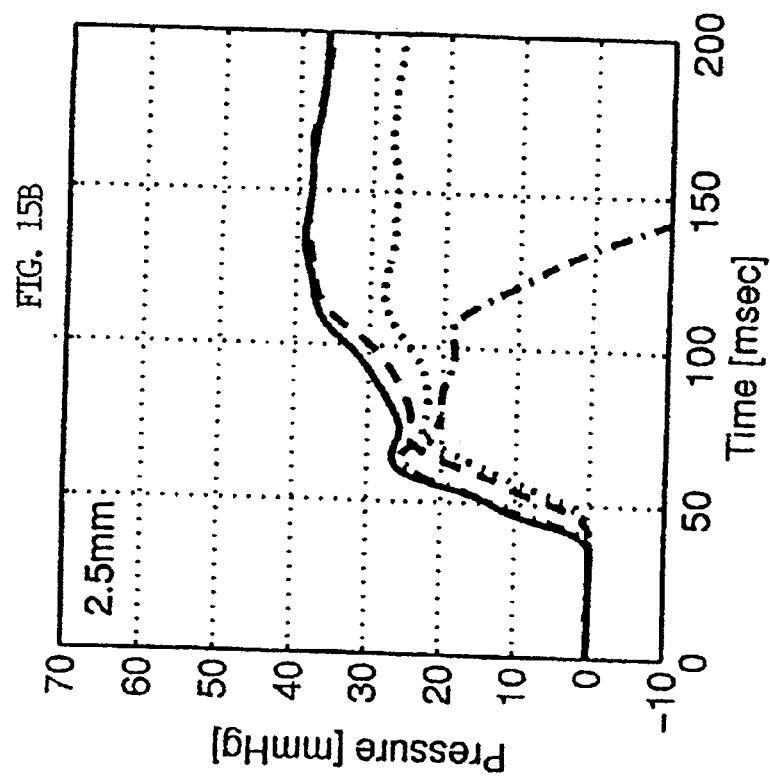
FIGS. 15a–f show pressure for distal constrictions measured by the first (solid) and second (dash) Biometrix sensors, and by the first (dot) and second (dash-dot) PVDF sensors.
Figure 15A:
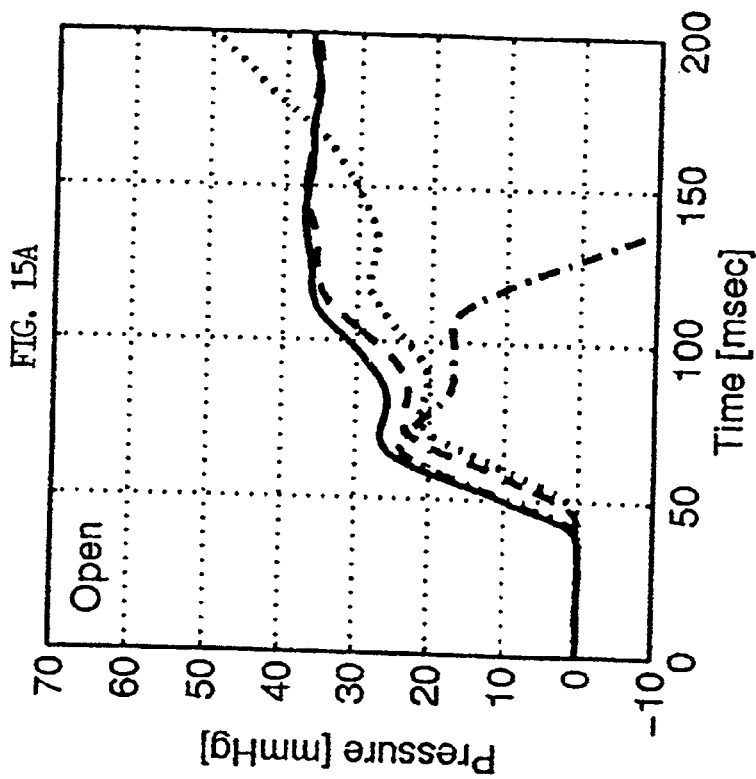
Figure 15C:
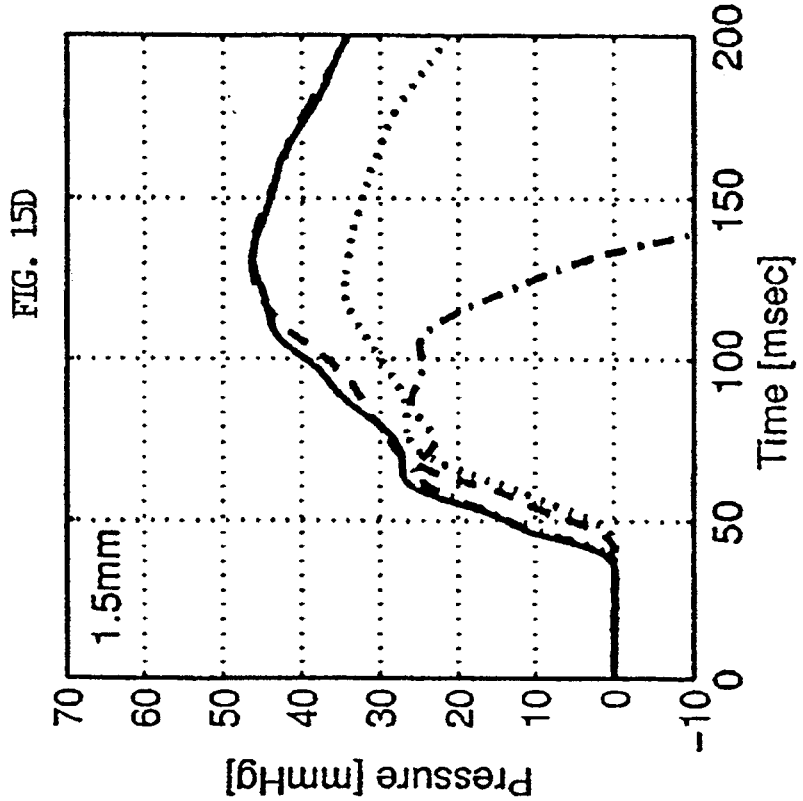
Figure 15D:
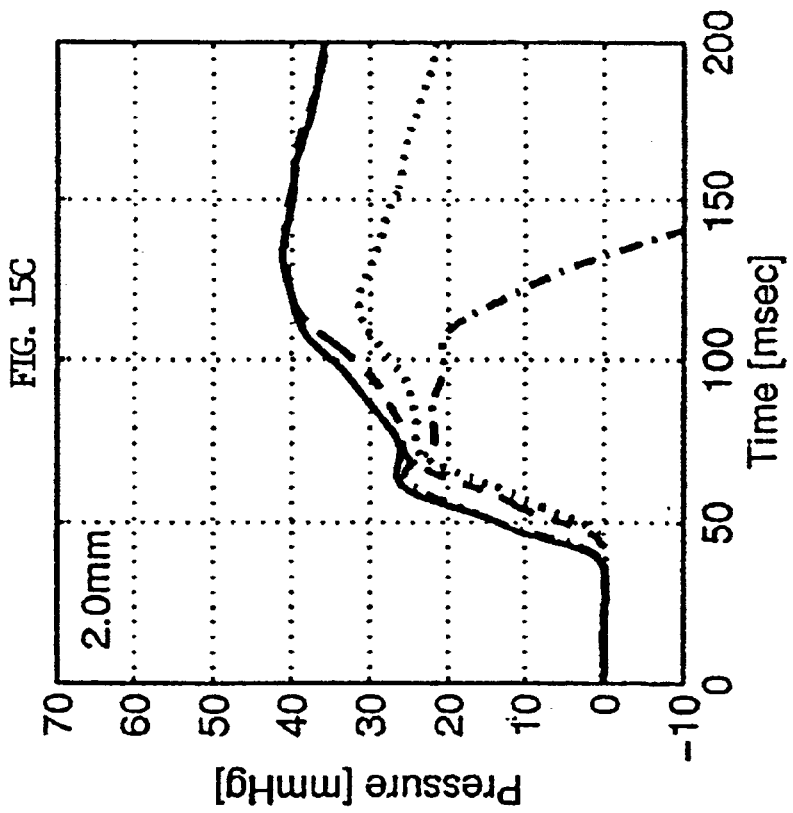
Figure 15F:
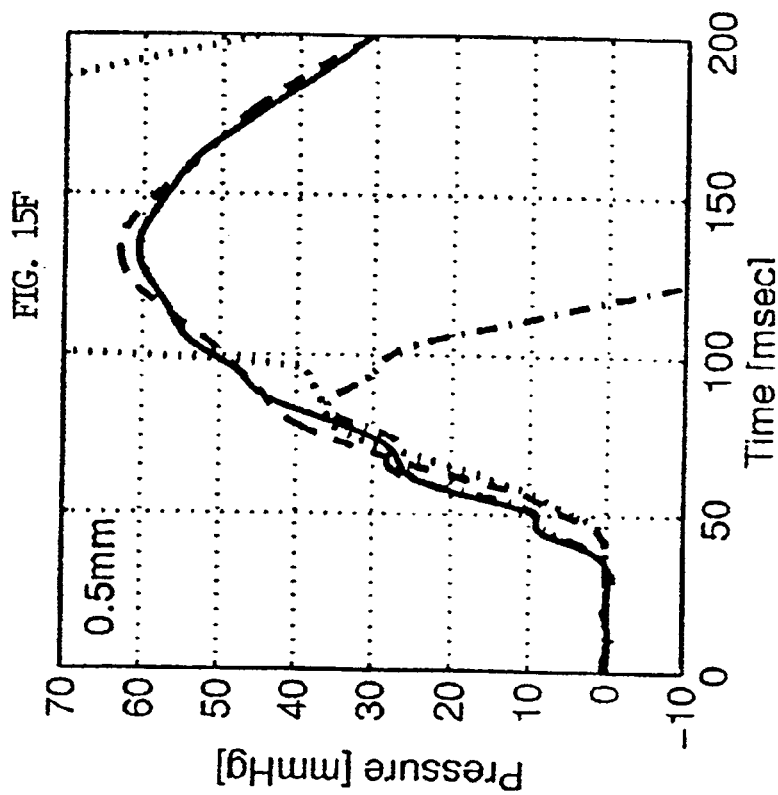
Figure 15E:
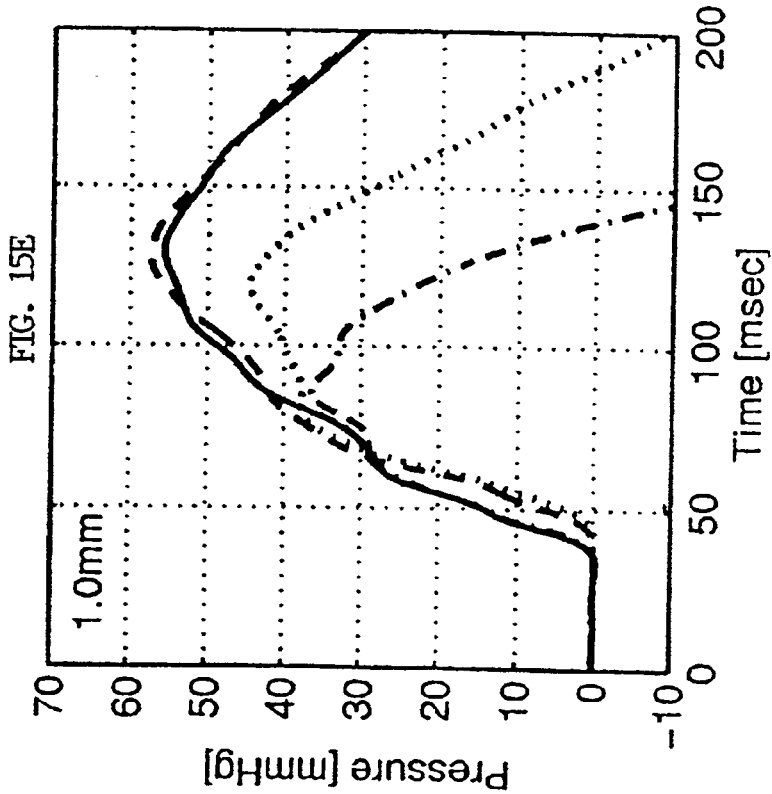
Figure 16D:
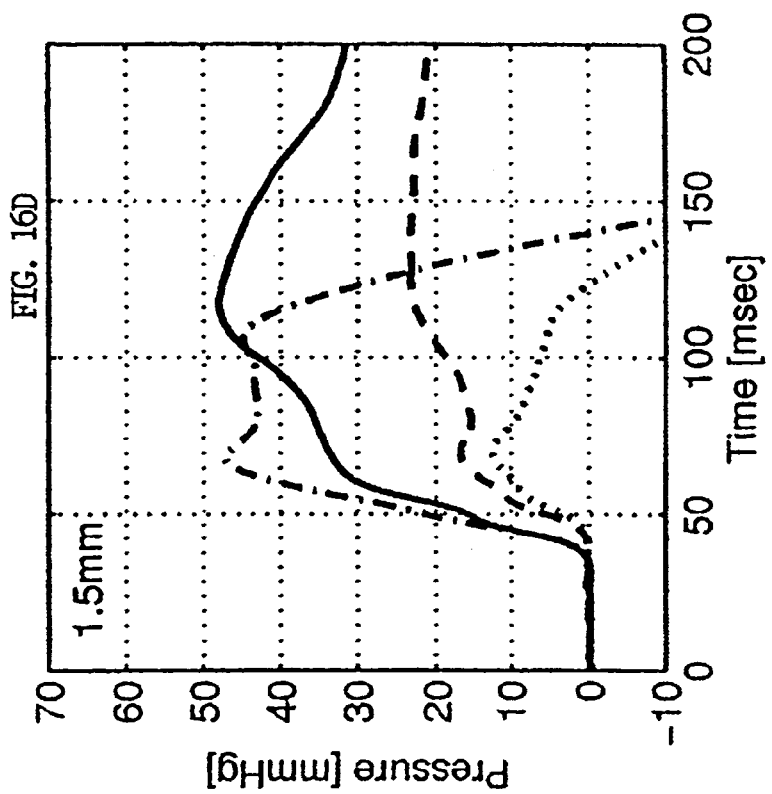
Figure 16C:
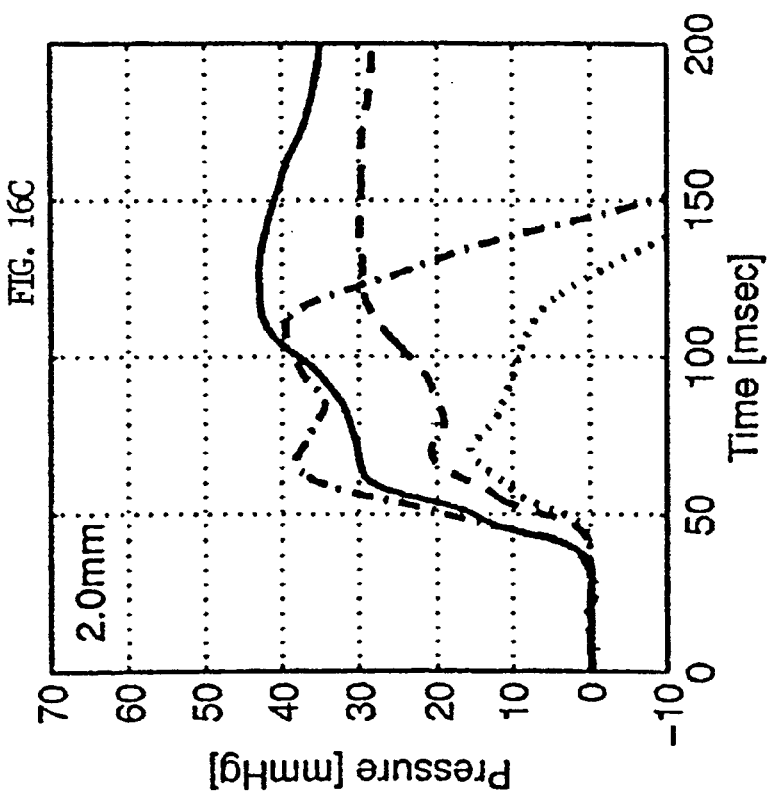
Figure 17C:
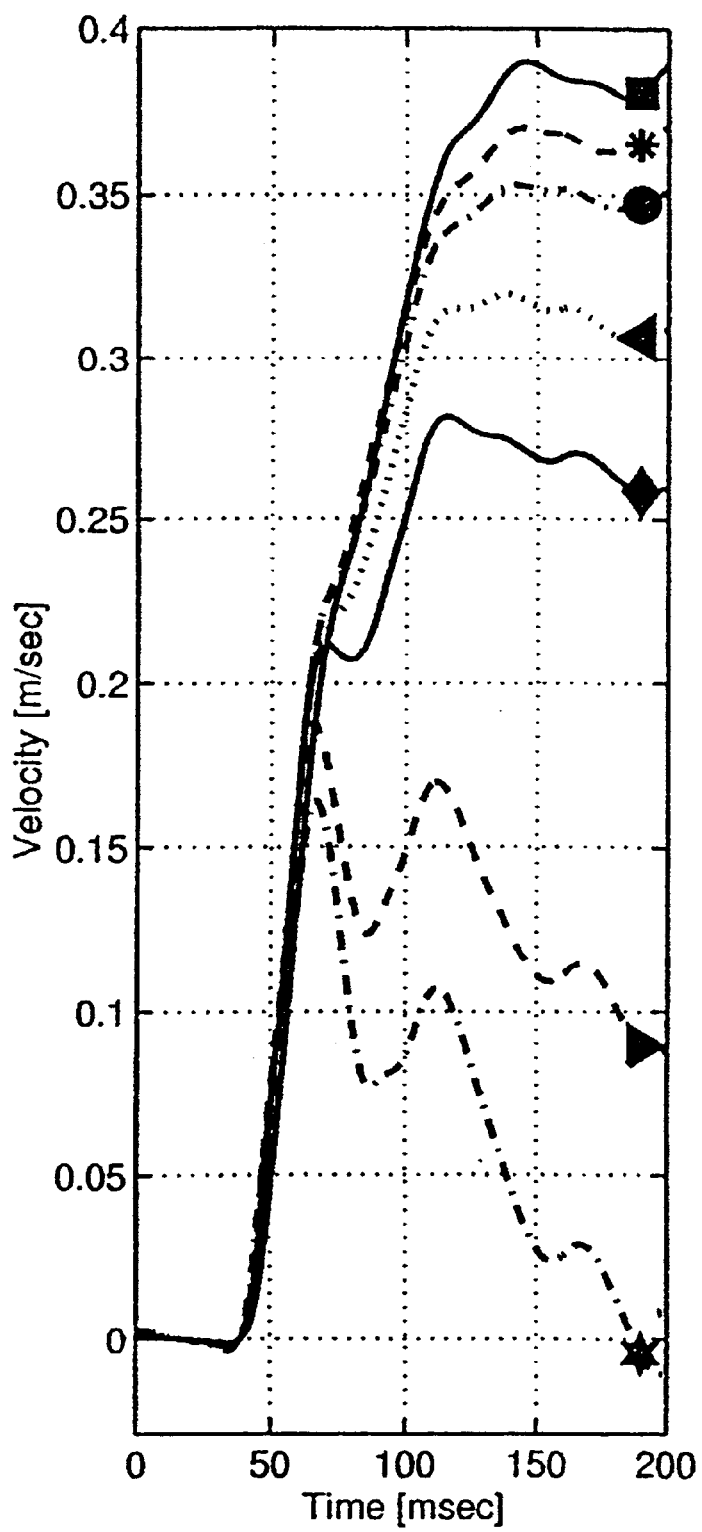

The resulting pressure pulse, as measured by the topmost Biometrix sensor, is plotted in FIG. 13. The pressure starts to increase about 40 msec after the electrical pulse. This time delay comprises a ~10 msec electromechanical opening time for the tap and its controlling relay, and a ~30 msec propagation delay. This translates into a propagation velocity of 14–18 m/sec, which is consistent with the previously measured figures for this latex pipe.

The typical rise time for the pulse is on the order of 80 msec. In addition to the gross shape, one can see a prominent peak in the pressure at 495 msec. This peak consistently lies 95 msec after the end of the pulse, even if the pulse width is varied. This is most probably caused by the (quite loud) impact of the valve armature at the end of its run, said 95 msec including both the closing delay and the acoustic propagation delay.

FIGS. 14a–f, 15a–f and 16a–f plot some of the raw data which was picked up in the three runs, displaying in each the first 200 msec of the received pulses, calibrated in mm of mercury (torr). The results are plotted for the three runs, each for an open system (no constrictions) and for constriction openings of 2.5, 2, 1.5, 1 and 0.5 mm, which translate to obstructions of 50%, 60%, 70%, 80% and 90% of the tube diameter, respectively. Each Figure displays superimposed the pressure picked up by the four sensors in the system: The first (solid) and second (dash) Biometrix sensors, and the first (dot) and second (dash-dot) Telesense PVDF sensors.

In general, one sees that the two Biometrix sensors yield pulse shapes which are very similar, except of course for the midway constriction case. The PVDF sensors mostly follow the Biometrix sensors for some time, but start to diverge after 70–120 msec, depending on the sensor. This divergence is unrelated to the pressure itself, as it varies in a consistent manner between successive pulses. It is most likely the result of static electricity, i.e., charges carried by the liquid as it flows through the (electrically insulating) pipe. Previous experiments have shown that this parasitic effect can be affected in a reproducible manner by grounding the pipe in the vicinity of the sensors, and is also affected by the purity (and therefore the conductivity) of the water in the system. Such free charges affect the high-impedance PVDF sensors much more than the low-impedance Biometrix sensors. In any case, in the present experiment this effect limits the usability of the PVDF data to the first 100 msec or so.

FIGS. 14a–f show pulses picked up for the various proximal constrictions. Note that, as the opening diameter decreases, so does the amplitude of the received pulse, consistently over all four sensors.

FIGS. 15a–f displays the pressure picked up for a variety of distal constrictions. As the constriction opening decreases, the amplitude of the pulse increases, and furthermore the pulse shape changes. This happens consistently for both the Biometrix sensors and the PVDF sensors. The quantitative match is also fairly good, although not as good as in the proximal case, as the delay before the extraneous signal is picked up by the PVDF sensors seems to have decreased somewhat.

FIGS. 16a–f provide data for midway constrictions. Both the Biometrix derived and the PVDF derived data show qualitatively the same effect: as the constriction diameter increases, the pulse picked up by the first sensor set, which are positioned upstream from the constrictions, increases in amplitude and changes its shape, while the pulse picked up by the downstream set decreases in amplitude. The PVDF sensors are less well behaved quantitatively in this run. One reason may be that, since the constriction lies quite close to sensors themselves, one did not quite got rid of all the air bubbles trapped close to the sensor body.

As mentioned hereinabove, if one measures the pressure at two nearby points one may also derive the mean instantaneous flow velocity. In the present experiment the data received by the Biometrix sensors was of sufficient quality to try this out. The equation used is the following:

$$\langle v(t) - v(t_0) \rangle = V_{t_0}(t) \equiv \frac{1}{\rho} \int_0^t \frac{P_1(t') - P_2(t')}{\Delta x} dt'$$

where $\rho$ is the liquid density (taken to be 1000 kg/m$^3$), $P_{1,2}(t)$ is the instantaneous pressure at the first and second sensing stations, respectively, measured in Pa, and $\Delta x$ is the distance between the sensing stations (0.12 m in this case). The resulting velocity is then given in m/sec.

The equation given above, and its application in the present experiment, is to some degree an approximation. One inaccuracy here is the implicit assumption that the velocity between the two sensors is constant along the longitudinal axis (the other directions are simply averaged over). This is more or less the case in the proximal and distal cases, except that an extraneous pressure drop caused by the presence of a PVDF sensor between them gives rise to a certain overestimate of the resulting velocity. This overestimate, however, manifests only as an overall scaling which is independent of any proximal or distal constriction. Another implicit assumption is that there are no other forces operating on the liquid. In the midway case, this last assumption is grossly violated, since the walls of the constriction which are present between the sensors operate with significant force to limit the flow. Thus, in the midway case there is no connection between $V_{t_0}(t)$ and the actual flow velocity. Nevertheless, one shall see that $V_{t_0}(t)$ remains a powerful and relevant diagnostic parameter in this case as well.

The actual results of the velocity measurements, as described above, are shown in FIGS. 17a–c. First consider the results for the proximal (17a) and distal (17c) cases. The velocity decreases with decreasing constriction diameter, as expected. The velocity takes some time to build up, and only seems to stabilize at the 150 msec mark. A further point which is apparent is that the velocity declines with decreasing constriction openings for both the proximal and the distal cases. Physically this is obvious, as the steady-state velocity should not depend on the position of the constriction. However, it is still gratifying to observe, especially since one recalls that the pressure pulse is completely different in the two cases—as the constriction closes, the pressure decreases in the proximal case and increases in the distal case. Nevertheless, the measured steady-state velocities in the two cases are very similar.

One further interesting point emerges from the distal case, when one compares the velocity curve for the open case and, e.g., for the 1 mm (80% closed) case. Up to the 65 msec mark the two curves coincide. At that point the open curve continues to rise, while the 1 mm constriction curve abruptly drops, and then saturates. This stands on contrast to the behavior of the equivalent curves in the proximal case. There the entire curve seems simply to scale down with increasing obstruction.

The physical interpretation for the observed phenomenon is the following. In the distal case, the sensors first pick up the pulse as it propagates upstream, before it has encountered the obstruction. At this stage the sensors do not yet "know" of the obstruction. This changes when the sensors pick up the leading edge of the wave which has been reflected from the constriction. This reflected wave also carries with it a backflow of liquid which causes the fluid velocity before the obstruction to match that which follows the obstruction. However, this takes time, time enough for the pressure pulse to travel from the sensor location to the constriction and back. During this time interval the sensors pick up the exact same pressure they are subject to in the absence of a constriction, and so the two curves coincide. It is only after this time, some 15–20 msec in the case studied, that the instantaneous velocity drops to its constriction-determined value. An interesting side-effect is that the temporal position of this leveling off gives us the distance between the sensor pair and the constriction itself, given a knowledge of the sound velocity. Moreover, if the sound velocity is not known, it can be read off on-line from the delay between the pulses in the two sensors.

Finally, turn one's attention to the midway case (17b). Here, the curves seem totally different. For one, the order is reversed—the smaller is the constriction diameter, the larger is the measured velocity. Also, the velocity seems to achieve the ridiculous value of 5 m/sec or more. However, as was mentioned before, in the midway case the displayed parameter, $V_{r_0}(t)$, does not in fact correspond to the flow velocity. The observed effect is then clear from the definition. As the constriction closes, the pressure increases in the first sensor and decreases in the second. The difference between the two pressures is then increasingly positive, and the integral yields larger and larger values. The shape of $V_{r_0}(t)$ is in this case distinctive, and serves as a clear signature of a midway obstruction.

The previous parameters discussed, the pressure and the velocity, both depend on having good calibration. For example, they are sensitive to the accuracy by which the systolic/diastolic blood pressure differential is known. In the following section an additional parameter, the acoustic impedance of the blood vessel, which is, at least in principle, independent of the blood pressure—it is purely a property of the vessel itself.

The experimental values obtained in the experiment for the relative impedance $\zeta(t)$ are now examined. In FIGS. 18a–c $\zeta(t)$ is plotted for all constrictions used, for the proximal, midway and distal cases. The first point to note is that the value obtained for $\zeta(t)$ in the open case lies around 0.87. This is remarkably close to 1, considering that the velocity measurements are only approximate. It confirms that the velocities obtained are slightly too high, as expected, but not by much. Another general point to note is that the impedance values stabilize around the 80 msec point (except for the midway case, where the physical meaning is lost anyway). This is in spite of the fact that the pressure and velocity themselves stabilize only around the 150 msec mark, and demonstrates the fact that $\zeta(t)$ measures properties of the pipe and not of the pulse.

Examining the proximal case, one sees that values of $\zeta(t)$ do not vary by much when the constriction closes, but fluctuates around 0.87 throughout. This is consistent with predictions given above. Thus $\zeta(t)$ is not a good indicator for proximal constrictions.

The picture changes when one examines the midway and distal results. A midway obstruction causes $\zeta(t)$ to decrease, and a distal obstruction causes $\zeta(t)$ to increase. Thus, for both midway and distal obstructions $\zeta(t)$ is a good indicator, and moreover one which is independent of both pulse shape and height and sensor sensitivity.

In order to summarize the results, a number of representative parameters have been devised, which can be used to compare the different cases and constrictions. These parameters may also be used as the diagnostic properties to be displayed to a future operator.

An obvious first parameter to look at is the pressure at a specific time mark, normalized to the pressure obtained in the absence of a constriction. This is what is displayed in FIGS. 19–21 and in Tables 1–6.

Figure 19A:
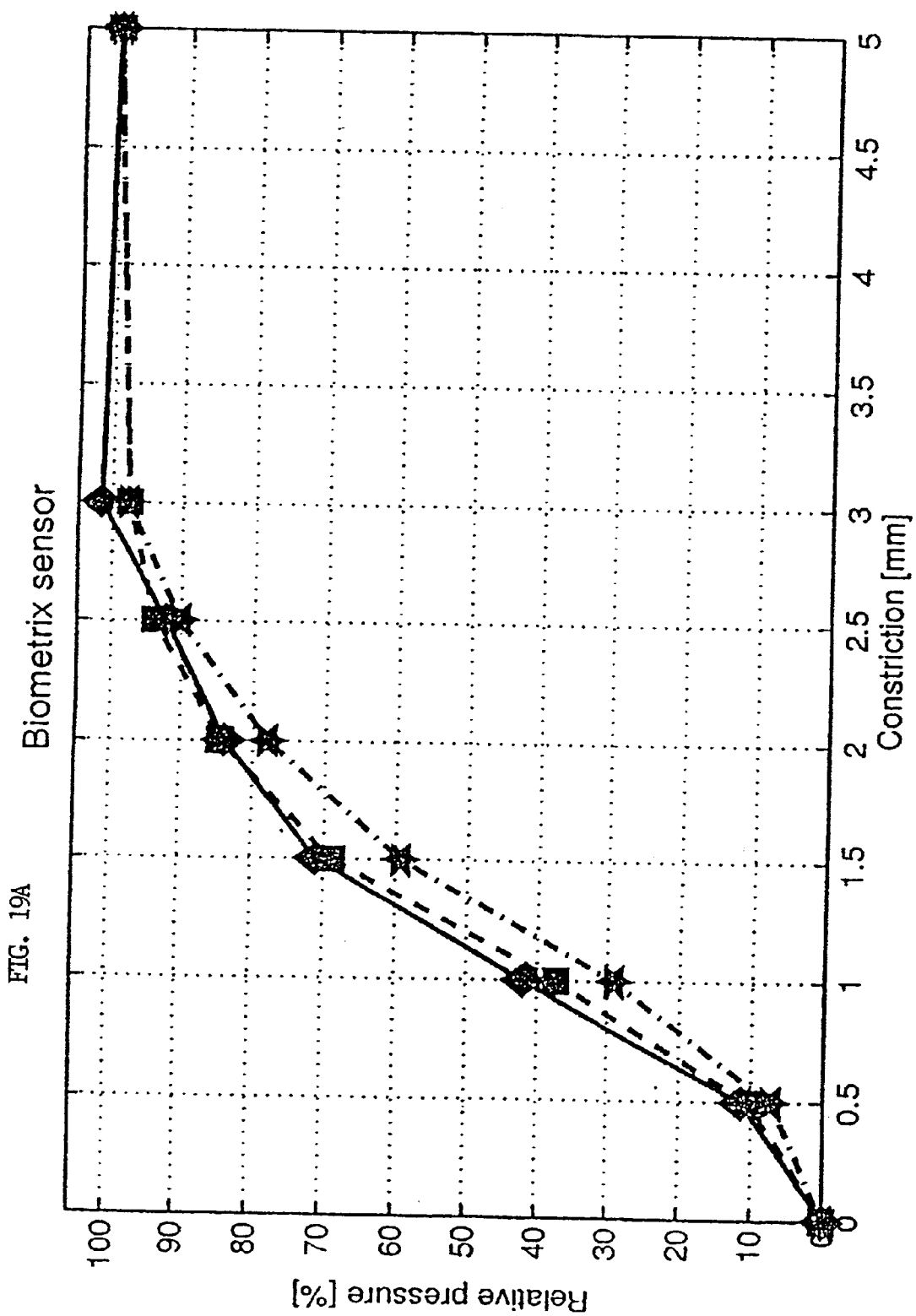
FIGS. 19a–b show pressure pulse in percent relative to the open case for proximal constrictions for both sensor types, the Biometrix sensor close to the constriction in FIG. 21a and the PVDF sensor close to the constriction in FIG. 21b, wherein solid indicates the 60 msec mark, dash—75 msec mark and dash-dot—100 msec mark.
Figure 19B:
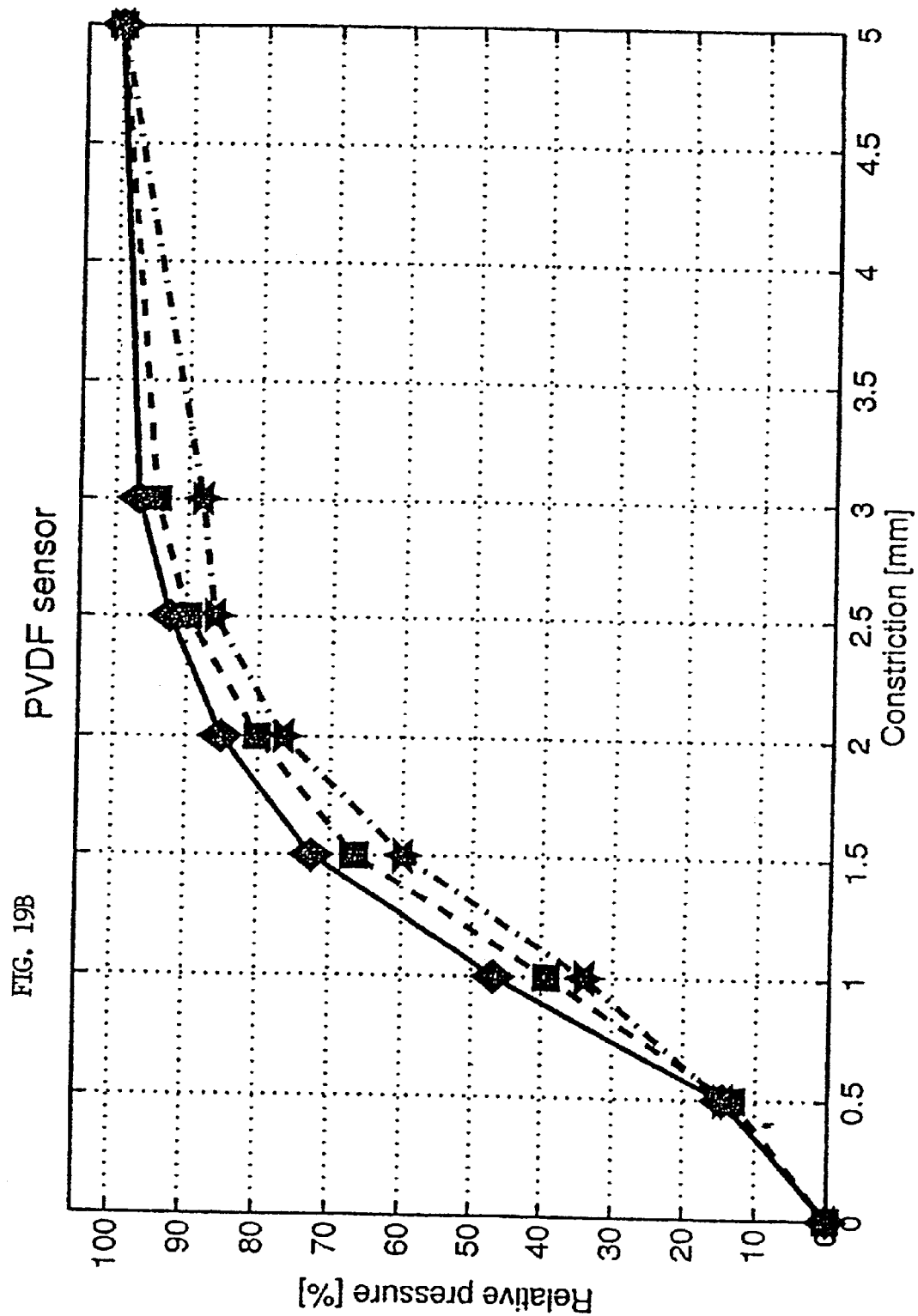

In FIGS. 19a–b and Tables 1 and 2 the relative pressure at the 60 msec, 75 msec and 100 msec marks are shown, as picked up by the first Biometrix sensor (upper graph) and PVDF sensor (lower graph), for the case of proximal constrictions. One sees there a well-defined curve on top of which the pressure drops more or less uniformly—there is no significant dependence on the time mark. It seems that detectable pressure drops start at about 50–60% obstruction, and are in any case unequivocal at 70% constriction. Also, the Biometrix and PVDF sensors yield very similar results.

TABLE 1

Relative pressure (%), proximal constriction, Biometrix sensor

| Delay | 5 mm | 3 mm | 2.5 mm | 2 mm | 1.5 mm | 1 mm | 0.5 mm |
|---|---|---|---|---|---|---|---|
| 60 msec | 100 | 102 | 92 | 84 | 71 | 42 | 11 |
| 75 msec | 100 | 98 | 94 | 84 | 69 | 37 | 10 |
| 100 msec | 100 | 98 | 90 | 78 | 59 | 29 | 7 |

TABLE 2

Relative pressure (%), proximal constriction, PVDF sensor

| Delay | 5 mm | 3 mm | 2.5 mm | 2 mm | 1.5 mm | 1 mm | 0.5 mm |
|---|---|---|---|---|---|---|---|
| 60 msec | 100 | 97 | 92 | 85 | 73 | 47 | 15 |
| 75 msec | 100 | 94 | 90 | 80 | 67 | 39 | 13 |
| 100 msec | 100 | 88 | 86 | 77 | 60 | 34 | 14 |

Figure 20A:
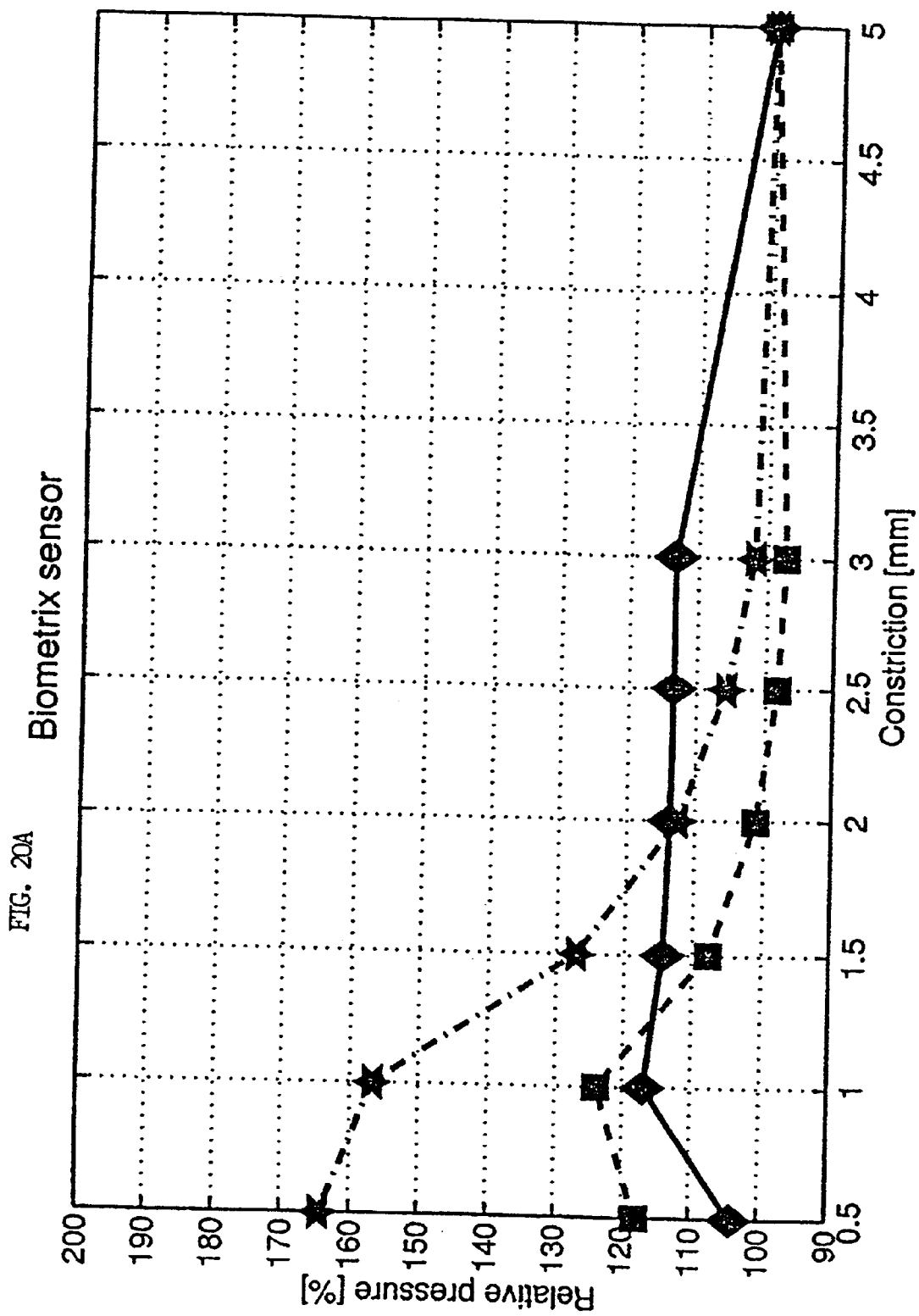
FIGS. 20a–b show pressure pulse in percent relative to the open case for distal constrictions for both sensor types, the Biometrix sensor close to the constriction in FIG. 21a and the PVDF sensor close to the constriction in FIG. 21b, wherein solid indicates the 60 msec mark, dash—75 msec mark and dash-dot—100 msec mark.
Figure 20B:
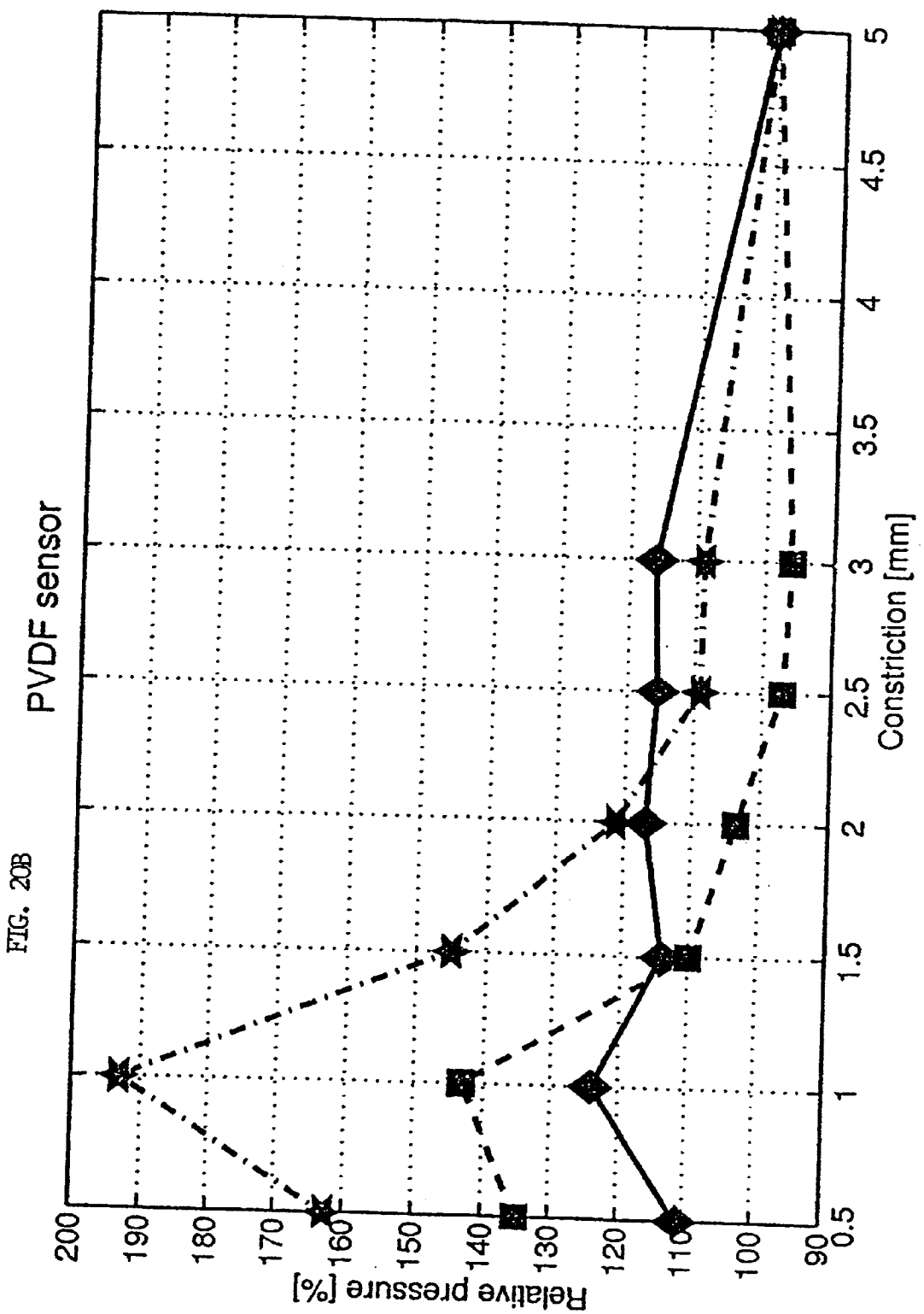

Next, in FIGS. 20a–b and Tables 3 and 4 the results for the distal constriction case are considered. Significant effects are seen only after at least 100 msec. Again, the detection threshold seems to be around 50–60% obstruction, depending on the sensitivity of the measurement and the quality of the normalization. The PVDF data is of lower quality in this case, since the correspondence between the two sensors is marginal at 100 msec. However, the qualitative effect is still there.

TABLE 3

Relative pressure (%), proximal constriction, Biometrix sensor

| Delay | 5 mm | 3 mm | 2.5 mm | 2 mm | 1.5 mm | 1 mm | 0.5 mm |
|---|---|---|---|---|---|---|---|
| 60 msec | 100 | 113 | 113 | 114 | 114 | 117 | 104 |
| 75 msec | 100 | 97 | 98 | 101 | 108 | 124 | 118 |
| 100 msec | 100 | 102 | 106 | 112 | 127 | 157 | 164 |

TABLE 4

Relative pressure (%), proximal constriction, PVDF sensor

| Delay | 5 mm | 3 mm | 2.5 mm | 2 mm | 1.5 mm | 1 mm | 0.5 mm |
|---|---|---|---|---|---|---|---|
| 60 msec | 100 | 116 | 115 | 117 | 114 | 124 | 111 |
| 75 msec | 100 | 96 | 97 | 103 | 110 | 143 | 135 |
| 100 msec | 100 | 109 | 109 | 121 | 145 | 193 | 163 |

Figure 21A:
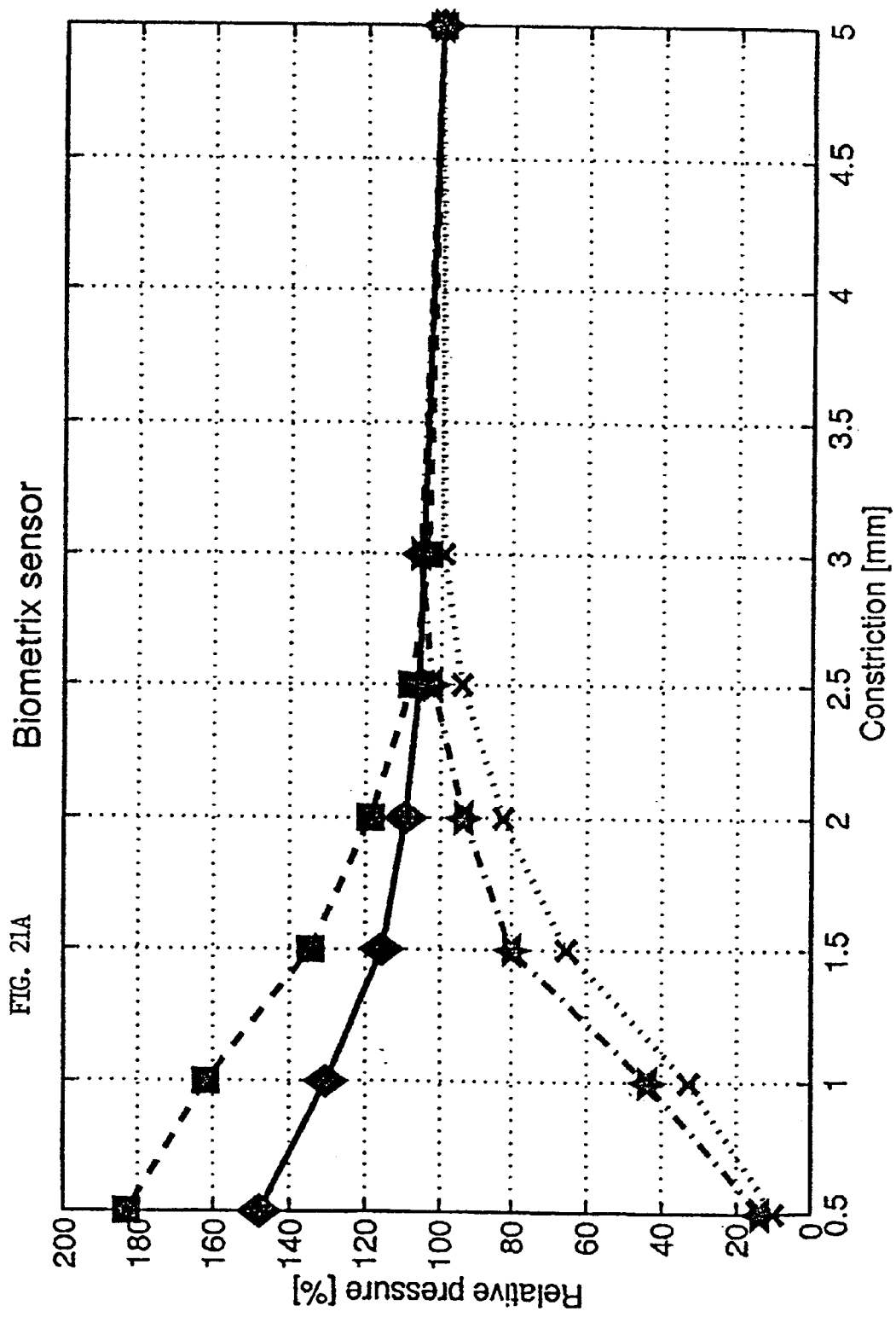
FIGS. 21a–b show pulse pressure in percent relative to the open case for midway constrictions and both sensor types, the two Biometrix sensors are represented in FIG. 21a, and the two PVDF sensors are represented in FIG. 21b. Solid—first sensor, 60 msec mark, dash—first sensor, 100 msec mark, dash-dot—second sensor, 60 msec mark, dot—second sensor, 100 msec mark.
Figure 21B:
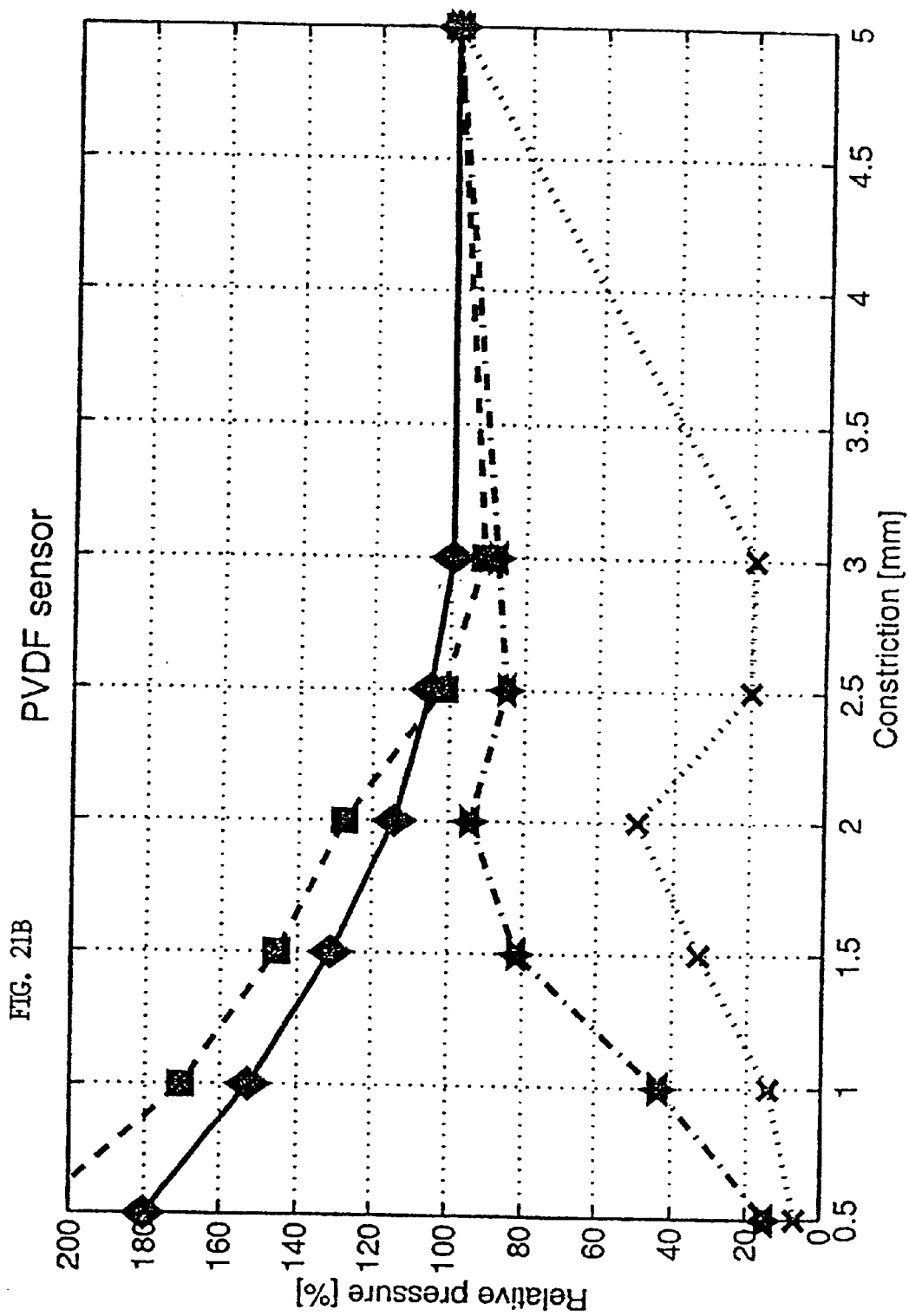

Finally, the results for the midway case are examined. In FIGS. 21a–b and Tables 5 and 6 the relative pressures at the 60 and 100 msec time marks are displayed for the two sensors in each respective sensor family—the two Biometrix sensors in the top graph, and the two PVDF sensors in the bottom graph. It is evident that the pressure increases in the first sensor and decreases in the second as the constriction closes. This is apparent for both the Biometrix sensors and the PVDF sensors. This implies that a combined criterion, e.g., one that takes the difference or the ratio between the first and second sensors, would be particularly sensitive to midway constrictions. Here the detection threshold would be expected to be lower than for the proximal or distal cases, lying at around 30–40% constriction.

TABLE 5

Relative pressure (%), proximal constriction, Biometrix sensor

| Sensor | Delay | 5 mm | 3 mm | 2.5 mm | 2 mm | 1.5 mm | 1 mm | 0.5 mm |
|---|---|---|---|---|---|---|---|---|
| 1 | 60 msec | 100 | 105 | 106 | 109 | 116 | 130 | 148 |
| 1 | 100 msec | 100 | 103 | 108 | 119 | 135 | 162 | 183 |
| 2 | 60 msec | 100 | 106 | 102 | 94 | 80 | 44 | 14 |
| 2 | 100 msec | 100 | 99 | 94 | 83 | 65 | 33 | 10 |

TABLE 6

Relative pressure (%), proximal constriction, PVDF sensor

| Sensor | Delay | 5 mm | 3 mm | 2.5 mm | 2 mm | 1.5 mm | 1 mm | 0.5 mm |
|---|---|---|---|---|---|---|---|---|
| 1 | 60 msec | 100 | 100 | 105 | 114 | 131 | 153 | 180 |
| 1 | 100 msec | 100 | 91 | 102 | 128 | 146 | 170 | 209 |
| 2 | 60 msec | 100 | 88 | 85 | 95 | 82 | 43 | 15 |
| 2 | 100 msec | 100 | 19 | 20 | 50 | 33 | 14 | 7 |

A second quantity one can look at is the velocity. FIGS. 22a–c plot $V_{f_0}(t)$, measured using the Biometrix sensors at the 150 msec mark, for the entire range of constrictions and constriction positions. The results are also tabulated in table 7.

TABLE 7

Velocity at the 100 msec mark relative to the open case, in percents

| Position | 5 mm | 3 mm | 2.5 mm | 2 mm | 1.5 mm | 1 mm | 0.5 mm |
|---|---|---|---|---|---|---|---|
| proximal | 100 | 95 | 89 | 75 | 54 | 25 | 6 |
| midway | 100 | 135 | 205 | 358 | 592 | 1021 | 1337 |
| distal | 100 | 94 | 89 | 80 | 68 | 26 | 3 |

First, consider the results for proximal and distal constrictions. It is immediately noticed that the results are very similar for the two constriction positions. In fact, the two curves are so similar as to be identical within the measurement accuracy. This is just what one expects for a genuine velocity measurement. The threshold for detection lies at around the 50–60% obstruction, again depending on the quality of the calibration. It is also interesting to note that most of the drop in the velocity occurs in a fairly narrow regime of 60–80% obstruction. This explains why obstructions in blood vessels start to display clinical symptoms only when they reach this regime.

Finally, consider $V_{f_0}(t)$ in the midway case. Here the resulting curve is totally different, increasing rather than decreasing as the obstruction closes. Here the system is more sensitive than in the previous cases, and one sees that $V_{f_0}(t)$ increases by some 40% even in the case of a 3 mm (40%) constriction. The detection threshold in this case is at most 40%, and may be even lower. Thus the sensitivity of $V_{f_0}(t)$ as a diagnostic parameter is at its height for midway constrictions.

Figure 23:
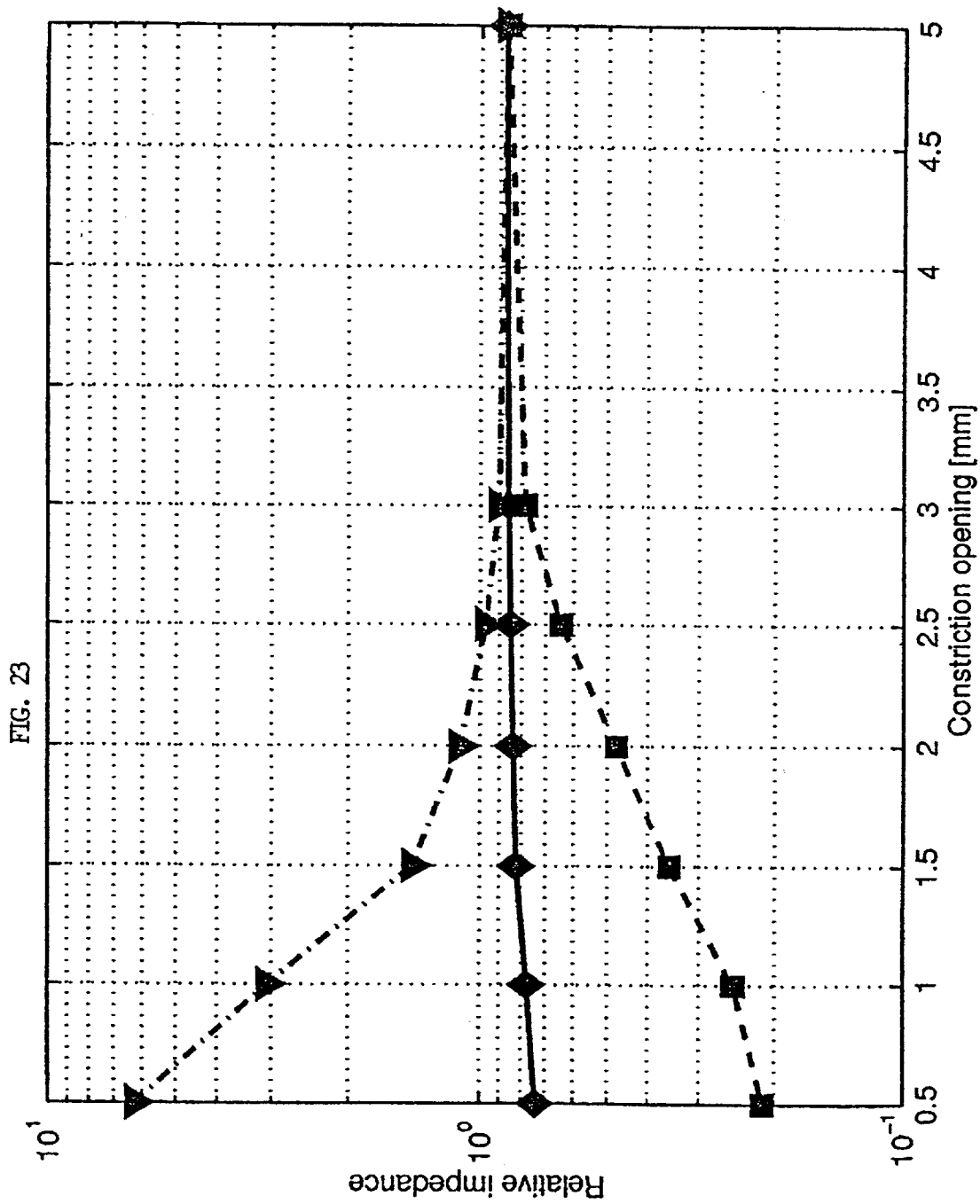
FIG. 23 shows the relative impedance of the 100 msec mark. Solid—proximal constriction, dash—distal constriction, dash-dot—midway constriction.

Next, the relative impedance $\zeta(t)$ is examined. FIG. 23 plots its value at the 100 msec mark, as previously it was observed that $\zeta(t)$ is stabilized at that point. The resulting values are plotted in the Figure, and tabulated in Tables 8 and 9.

TABLE 8

Impedance at the 100 msec mark relative to the characteristic impedance

| Position | 5 mm | 3 mm | 2.5 mm | 2 mm | 1.5 mm | 1 mm | 0.5 mm |
|---|---|---|---|---|---|---|---|
| proximal | 0.87 | 0.86 | 0.85 | 0.84 | 0.82 | 0.78 | 0.74 |
| midway | 0.86 | 0.78 | 0.64 | 0.48 | 0.35 | 0.25 | 0.21 |
| distal | 0.87 | 0.91 | 0.97 | 1.11 | 1.42 | 3.07 | 6.23 |

TABLE 9

Impedance at the 100 msec mark relative to the open case, in percent

| Position | 5 mm | 3 mm | 2.5 mm | 2 mm | 1.5 mm | 1 mm | 0.5 mm |
|---|---|---|---|---|---|---|---|
| proximal | 0 | −1 | −2 | −4 | −5 | −11 | −15 |
| midway | 0 | −9 | −25 | −45 | −59 | −71 | −75 |
| distal | 0 | +4 | +12 | +28 | +64 | +254 | +618 |

One sees that for the proximal case, there is little dependence of the impedance on constriction opening. In contrast, for the distal case the impedance increases with closing constriction. It has already changed by 12% for a 50% obstruction and by 28% for a 60% obstruction. Recalling that $\zeta(t)$ is independent of pulse height, and (almost) independent of pulse shape, this means that a 50% distal obstruction is most probably detectable even without calibrating the blood pressure.

For the midway constriction case, $\zeta(t)$ decreases as the constriction closes. Here the sensitivity is even better –40% obstruction results in a 9% decline, and a 50% obstruction in a 25% decline. Thus, in the midway case a 50% obstruction should be easily detectable, and possibly even a 40% obstruction threshold is feasible.

Finally, let us re-examine closely the results for the distal constriction case. It was argued above that the pressure and the velocity at the sensor location x and for a constriction at y>x are given by the generic form:

$$P(x, t) = f(x - ct) + Rf(2y - x - c);$$

$$v(x, t) = \frac{1}{\rho c}[f(x - ct) - Rf(2y - x - ct)]$$

where $f(x)$ is the functional description of the pulse shape. From the above equation one can extract:

$$f(x-ct)=\tfrac{1}{2}[P(x,t)+\rho cv(x,t)], Rf(2y-x-ct)=\tfrac{1}{2}[P(x,t)-\rho cv(x,t)]$$

Additionally, recall that, defining D=y−x one can write $$f(2y - x - ct) = f(x - c(t - \delta t)), \delta t = \frac{2D}{c}$$

Thus $Rf(2y-x-ct)$ is just a scaled and time-shifted copy of $f(x-ct)$.

By comparing the two one can obtain both the reflection coefficient R and the distance to the constriction D.

Figure 24:
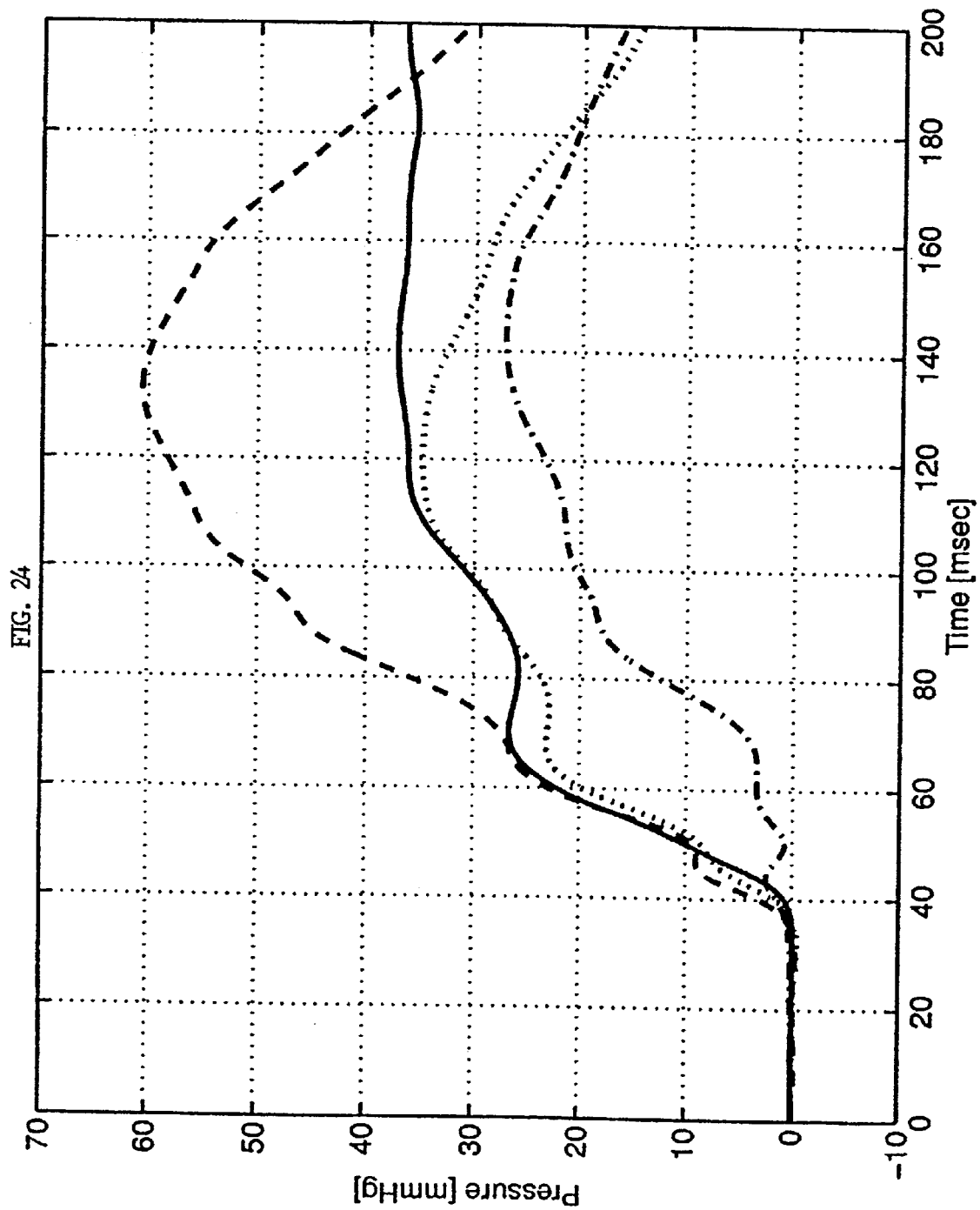
FIG. 24 shows the evaluation of incident and reflected pulses for a 1 mm constriction. Solid—pulse measured with no constriction, dash—pulse measured with constriction, dot—reconstruction of the incident pulse, dash-dot—reconstruction of the reflected pulse.

This idea is tested in FIG. 24 which plots the original pulse, obtained by direct measurement in the absence of a constriction, and the pressure pulse measured in the presence of a 1 mm (80%) constriction. In addition, for the same constriction it plots both the incident pulse $f(x-ct)$ and the reflected pulse $Rf(2y-x-ct)$, as evaluated using the equations given above from the measurements performed for a 1 mm distal constriction.

Clearly there are some inaccuracies in the evaluation, resulting from the fact that the distance between the two sensors is not smaller than the distance to the constriction itself. Nevertheless, one sees that, using solely the data obtained in the presence of the constriction, one is able to reconstruct the first 120 msec or so of the original, unobstructed pulse. Additionally, one separates out the reflected wave, and observes that it is a scaled by ~0.55 and shifted by 25 msec version of the original pulse. One obtains:

$R \approx 0.55, D = \tfrac{1}{2}c \cdot \delta t \approx 20$ cm which was indeed roughly the distance between the sensor pair and the distal constriction. One sees that, in the distal constriction case, it is possible to reliably obtain not only the degree of obstruction, but also its position.

In this study several measurable parameters of pulsatile flow were examined in elastic tubing. The pulsatile flow was generated by means of a computer-controlled electric valve, and the resulting instantaneous pressure at two nearby points in the tube were measured. This measurement was repeated while introducing a variety of constrictions at three different locations—upstream from the sensors (proximal location), in between the sensors (midway location), and downstream from the sensors (distal location). Two types of sensors were used in the experiment—commercial (Biometrix) sensors, and custom-made PVDF sensors. From the pair of pressure measurements, in addition to the pressure, values for the instantaneous flow velocity and the acoustic impedance of the tube/constriction system were derived. For the distal case, the incident and reflected waves themselves were also reconstructed, enabling one to obtain both the degree of obstruction and its distance from the sensors.

The results obtained in the experiment demonstrate that constrictions give rise to significant and characteristic changes in all the measured parameters. Proximal constrictions lower both the pressure and the velocity, keeping the impedance unchanged. Distal constrictions increase he pressure and lower the velocity, thus increasing the impedance. Midway constrictions increase the pressure and the apparent velocity (which however does not correspond to a physical velocity for such constrictions), and in total lower the impedance.

One can therefore devise several normalized parameters that can serve as diagnostic tools to identify constrictions—the relative pressure, velocity, and/or impedance at a certain point in the pulse cycle, and the incident/reflected wave delay. Relative pressure and velocity parameters require knowledge of the overall pulse height, which should come from some external calibration technique, e.g., by externally measuring the blood pressure. The impedance, in contrast, is normalized by definition and is independent of the blood pressure, but does not indicate proximal constrictions. The results obtainable from these parameters is summarized below in Table 10.

TABLE 10

Summary of the constriction detection threshold and the properties of several constriction detection parameters, assuming a 15–20% change is readily detectable

|  | Proximal | Midway | Distal | Calib. | Notes |
| --- | --- | --- | --- | --- | --- |
| Pressure | 50–60% | 50–60% | 60% | Yes | Requires 2 measurements in order to identify midway constrictions. |
| Velocity | 50–60% | 50% | 50–60% | Yes | Requires a pressure measurement to differentiate proximal and distal constrictions. |
| Impedance | N/A | 40–50% | 50% | No | Is independent of overall pressure. Can't detect proximal constrictions. |
| Reflection Delay | N/A | N/A | 70% | No | Yields the distance to the obstruction for distal cases. |

All methods can detect proximal and distal constrictions from around 50–60% of the diameter, in a fairly conservative estimate. The sensitivity to midway constrictions is higher, and they may be reliably detected from around 40% obstruction. In addition, the impedance serves as a convenient and sensitive indicator for midway and distal constrictions.

The behavior of the PVDF sensors relative to the commercial Biometrix sensors were also examined. The PVDF sensors follow the Biometrix results for the first 70–100 msec. Following this time there is a divergence. This divergence has tentatively been linked to an electrostatic phenomenon caused by charge carriers being generated and carried by the flow. This effect has been shown to depend on the way in which portions of the vessels are electrically grounded, should disappear for flow inside non-insulating tubes, such as blood vessels.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

What is claimed is:

1. A system for quantifying pulsatile flow in a pipe, the system comprising:
    (a) at least two pressure sensors;
    (b) a mechanism for attaching said at least two pressure sensors onto inner walls of the pipe in a spaced configuration;
    (c) a processing module for receiving pressure records from each of said at least two pressure sensors and for quantifying the pulsatile flow in the pipe; and
    (d) a non-invasively activatable acoustic transducer element for communicating data from within the pipe to a receptive acoustic transducer outside thereof.

2. The system of claim 1, wherein said non-invasively activatable acoustic transducer element includes:
    (i) a cell member having a cavity;
    (ii) a substantially flexible piezoelectric layer attached to said cell member, said piezoelectric layer having an external surface and an internal surface, said piezoelectric layer featuring such dimensions so as to enable fluctuations thereof at its resonance frequency upon impinging of an external acoustic wave; and
    (iii) a first electrode attached to said external surface and a second electrode attached to said internal surface.

3. The system of claim 1, wherein said mechanism for attaching said at least two pressure sensors onto said inner walls of the pipe in said spaced configuration is a platform which serves for holding said at least two pressure sensors and is itself insertable into the pipe.

4. The system of claim 1, wherein the pipe is selected from the group consisting of a portion of a plumbing installation and a blood vessel.

5. The system of claim 3, wherein said platform is a stent insertable into a blood vessel.

6. A system for detecting a location of an obstruction in a pipe characterized in pulsatile flow, the system comprising:
    (a) at least two pressure sensors;
    (b) a mechanism for attaching said at least two pressure sensors onto inner walls of the pipe in a spaced configuration;
    (c) a processing module for receiving pressure records from each of said at least two pressure sensors and for detecting the location of the obstruction in the pipe; and
    (d) a non-invasively activatable acoustic transducer element for communicating data from within the pipe to a receptive acoustic transducer outside thereof.

7. The system of claim 6, wherein said non-invasively activatable acoustic transducer element includes:
    (i) a cell member having a cavity;
    a substantially flexible piezoelectric layer attached to said cell member, said piezoelectric layer having an external surface and an internal surface, said piezoelectric layer featuring such dimensions so as to enable fluctuations thereof at its resonance frequency upon impinging of an external acoustic wave; and
    (iii) a first electrode attached to said external surface and a second electrode attached to said internal surface.

8. The system of claim 6, wherein said mechanism for attaching said at least two pressure sensors onto said inner walls of the pipe in said spaced configuration is a platform which serves for holding said at least two pressure sensors and is itself insertable into the pipe.

9. The system of claim 6, wherein the pipe is selected from the group consisting of a portion of a plumbing installation and a blood vessel.

10. The system of claim 8, wherein said platform is a stent insertable into a blood vessel.

11. A system for quantifying a degree of an obstruction in a pipe characterized in pulsatile flow, the system comprising:
    (a) at least two pressure sensors;
    (b) a mechanism for attaching said at least two pressure sensors onto inner walls of the pipe in a spaced configuration;
    (c) a processing module for receiving pressure records from each of said at least two pressure sensors and for quantifying the degree of the obstruction in the pipe; and
    (d) a non-invasively activatable acoustic transducer element for communicating data from within the pipe to a receptive acoustic transducer outside thereof.

12. The system of claim 11, wherein said non-invasively activatable acoustic transducer element includes:
    (i) a cell member having a cavity;
    (ii) a substantially flexible piezoelectric layer attached to said cell member, said piezoelectric layer having an external surface and an internal surface, said piezoelectric layer featuring such dimensions so as to enable fluctuations thereof at its resonance frequency upon impinging of an external acoustic wave; and
    (iii) a first electrode attached to said external surface and a second electrode attached to said internal surface.

13. The system of claim 11, wherein said mechanism for attaching said at least two pressure sensors onto said inner walls of the pipe in said spaced configuration is a platform which serves for holding said at least two pressure sensors and is itself insertable into the pipe.

14. The system of claim 11, wherein the pipe is selected from the group consisting of a portion of a plumbing installation and a blood vessel.

15. The system of claim 13, wherein said platform is a stent insertable into a blood vessel.

16. A system for quantifying flow, detecting a location of an obstruction and quantifying a degree of the obstruction in a pipe characterized in pulsatile flow, the system comprising:
    (a) at least two pressure sensors;
    (b) a mechanism for attaching said at least two pressure sensors onto inner walls of the pipe in a spaced configuration;
    (c) a processing module for receiving pressure records from each of said at least two pressure sensors and for quantifying the pulsatile flow in the pipe, for detecting the location of the obstruction in the pipe and for quantifying the degree of the obstruction in the pipe; and (d) a non-invasively activatable acoustic transducer element for communicating data from within the pipe to a receptive acoustic transducer outside thereof.

17. The system of claim 16, wherein said non-invasivly activatable acoustic transducer element includes:

(i) a cell member having a cavity;

(ii) a substantially flexible piezoelectric layer attached to said cell member, said piezoelectric layer having an external surface and an internal surface, said piezoelectric layer featuring such dimensions so as to enable fluctuations thereof at its resonance frequency upon impinging of an external acoustic wave; and (iii) a first electrode attached to said external surface and a second electrode attached to said internal surface.

18. The system of claim 16, wherein said mechanism for attaching said at least two pressure sensors onto said inner walls of the pipe in said spaced configuration is a platform which serves for holding said at least two pressure sensors and is itself insertable into the pipe.

19. The system of claim 16, wherein the pipe is selected from the group consisting of a portion of a plumbing installation and a blood vessel.

20. The system of claim 18, wherein said platform is a stent insertable into a blood vessel.

21. A system for quantifying flow in a pipe characterized in pulsatile flow, the system comprising:

(a) at least two pressure sensors;

(b) a mechanism for attaching said at least two pressure sensors onto inner walls of the pipe in a spaced configuration;

(c) a processing module for receiving instantaneous pressure records from said at least two pressure sensors and for calculating an acoustic wave propagation velocity from said instantaneous pressure records to thereby determine at least one of pressure gradient, flow velocity and acoustic impedance across said at least two pressure sensors thus quantifying the pulsatile flow in the pipe.

22. The system of claim 21, wherein said pressure gradient, flow velocity and acoustic impedance across said at least two pressure sensors determined by said processing module is used by said processing module to detect a location of an obstruction in the pipe relative to said at least two pressure sensors.

23. The system of claim 22, wherein said pressure gradient, flow velocity and acoustic impedance across said at least two pressure sensors determined by said processing module is used by said processing module to quantify a degree of said obstruction.

24. The system of claim 21, wherein said mechanism for attaching said at least two pressure sensors onto said inner walls of the pipe in said spaced configuration is a platform which serves for holding said at least two pressure sensors and is itself insertable into the pipe.

25. The system of claim 21, wherein the pipe is selected from the group consisting of a portion of a plumbing installation and a blood vessel.

26. The system of claim 21, wherein said platform is a stent insertable into a blood vessel.

27. The system of claim 21, further comprising:

(d) a non-invasively activatable acoustic transducer element for communicating data from within the pipe to a receptive acoustic transducer outside thereof.

28. The system of claim 27, wherein said non-invasivly activatable acoustic transducer element includes:

(i) a cell member having a cavity;

(ii) a substantially flexible piezoelectric layer attached to said cell member, said piezoelectric layer having an external surface and an internal surface, said piezoelectric layer featuring such dimensions so as to enable fluctuations thereof at its resonance frequency upon impinging of an external acoustic wave; and (iii) a first electrode attached to said external surface and a second electrode attached to said internal surface.

* * * * *